United States Patent
Zou et al.

(10) Patent No.: US 8,993,034 B2
(45) Date of Patent: Mar. 31, 2015

(54) OIL COMPRISING DIACYLGLYCEROL ACYLTRANSFERASE 2 GENES AND PROTEINS ENCODED THEREBY FROM ALGAE

(71) Applicants: National Research Council of Canada, Ottawa (CA); Dow AgroSciences, LLC, Indianapolis, IN (US)

(72) Inventors: Jitao Zou, Saskatoon (CA); Jingyu Xu, Saskatoon (CA); Zhifu Zheng, Zionsville, IN (US)

(73) Assignees: Dow AgroSciences LLC, Indianapolis, IN (US); National Research Council Canada, Ottawa, Ontario (CA)

( * ) Notice: Subject to any disclaimer, the term of this patent is extended or adjusted under 35 U.S.C. 154(b) by 0 days.

(21) Appl. No.: 14/188,505

(22) Filed: Feb. 24, 2014

(65) Prior Publication Data

US 2014/0330003 A1 Nov. 6, 2014

Related U.S. Application Data

(62) Division of application No. 12/735,132, filed as application No. PCT/US2008/013811 on Dec. 16, 2008, now Pat. No. 8,658,855.

(60) Provisional application No. 61/008,752, filed on Dec. 21, 2007.

(51) Int. Cl.
| | |
|---|---|
| *A23D 9/00* | (2006.01) |
| *C12P 7/64* | (2006.01) |
| *C12N 5/14* | (2006.01) |
| *C12N 9/10* | (2006.01) |
| *A01H 5/00* | (2006.01) |
| *C12N 15/82* | (2006.01) |

(52) U.S. Cl.
CPC .......... *C12N 9/1029* (2013.01); *C12N 15/8247* (2013.01); *C12Y 203/0102* (2013.01)
USPC ........... 426/601; 800/281; 800/306; 435/134; 435/193

(58) Field of Classification Search
None
See application file for complete search history.

(56) References Cited

U.S. PATENT DOCUMENTS

| | | |
|---|---|---|
| 7,105,723 B2 | 9/2006 | Haertel et al. |
| 2004/0133944 A1 | 7/2004 | Hake et al. |
| 2005/0130284 A1 | 6/2005 | Milcamps et al. |
| 2005/0287652 A1 | 12/2005 | Damude et al. |
| 2006/0094088 A1 | 5/2006 | Picataggio et al. |

FOREIGN PATENT DOCUMENTS

WO 2009085169 A2 12/2009

OTHER PUBLICATIONS

Armbrust et al., The genome of the diatom *Thalassiosira pseudonana*: Ecology, evolution and metabolism, Science, Oct. 1, 2004, vol. 306, pp. 79-85.
Richardson et al., Database GenBank/DDBJ/EMBLGeneSeq, Accession No. FC532806.1, 2007, URL <http://www.ncbi.nlm.nih.gov/nucest/FC532806.1>.
Database UniProt [Online] XP002627492, Database accession No. A81XB2, printed May 11, 2010.
Dubois et al., "Fatty acid profiles of 80 vegetable oils with regard to their nutritional potential," 2007 Eur. J. Lipid Sci. Technol., vol. 109: p. 710-732.
Guo et al., "Protein tolerance to random amino acid change," 2004, PNAS, vol. 101, pp. 9205-9210.
Lardizabal, et al., DGAT2 Is a New Diacylglycerol Acyltransferase Gene Family, J. Biol. Chem., 2001, vol. 276, pp. 38862-38869.
Office Action in Japanese Patent Application No. 2010-539472, dated Aug. 19, 2013, 11 pages.
PCT International Search Report and Written Opinion for PCT/US2008/13811, dated May 12, 2009, 9 pages.
Supplementary European Search Report, EP 08 86 8776, dated Mar. 10, 2011, 7 pages.
Tonon et al., Long chain polyunsaturated fatty acid production and partitioning to triacylglycerols in four microalgae, Phytochemistry. 2002, vol. 61, pp. 15-24.

*Primary Examiner* — Brent T Page
*Assistant Examiner* — Matthew Keogh
(74) *Attorney, Agent, or Firm* — TraskBritt, P.C.

(57) ABSTRACT

The present disclosure relates to the isolation, purification, and characterization of a diacylglycerol acyltransferase 2 (DGAT2), and genes encoding DGAT2, from algae. DGAT2 can incorporate very long-chain polyunsaturated fatty acids into triacylglycerol more efficiently than DGAT1. The disclosure concerns methods of regulating seed oil content, fatty acid synthesis and fatty acid composition using the DGAT2 gene and to tissues and plants transformed with the gene. The disclosure also relates to transgenic plants, plant tissues and plant seeds having a genome containing an introduced DNA sequence of the disclosure, and a method of producing such plants and plant seeds.

12 Claims, 9 Drawing Sheets

FIG. 1A

```
TpDGA2-Pro           M    T    T    K    K    R    P    K    P    R    H    K    H    L
TpDGA2-DNA      1    atg  aca  aca  aag  aag  cgt  cca  cta  ccc  cgt  cat  ctg  cac  ctt
                     P    P    G    V    E    V    L    V    S    P    P    P    Y    E
               43    cca  cct  gga  gta  gaa  gta  ctc  gtc  tct  cca  cca  ccc  tac  gaa
                     V    C    T    L    V    D    R    L    L    V    Y    A    S    S
               85    gta  tgc  acg  ctc  gtc  gac  aga  ttg  ttg  gtc  tac  gcc  tcg  tcg
                     L    I    V    V    G    S    P    V    W    F    Y    G    G    I
              127    ttg  att  gtc  gtt  gga  tct  ccc  gtt  tgg  ttc  tac  gga  ggc  atc
                     I    Y    F    Y    R    K    W    K    L    Y    R    S    K    A
              169    att  tat  ttt  tac  agg  aag  tgg  aag  aag  tat  cgt  tct  ctt  gct
                     A    A    T    F    A    A    R    H    E    S    G    G    G    G
              211    gct  gct  act  gag  gct  gcg  aga  cat  gag  agt  ggt  ggc  ggt  ggt
                     A    S    S    T    V    R    C    R    G    T    R    Q    R    T
              253    gca  tcg  tca  acg  gtt  cgt  tgc  aga  ggt  aca  cgt  caa  cgt  aca
                     S    S    D    D    G    N    Y    T    S    S    T    G    E    S
              295    tcg  tct  gat  gac  ggc  aac  tac  aca  tcg  tca  act  ggc  gaa  agc
                     S    Q    E    M    N    E    Q    E    T    Q    T    Q    S    H
              337    tcg  caa  gaa  atg  aac  gaa  caa  gag  aca  caa  aca  caa  tca  cat
                     R    Q    Q    T    E    Q    Y    N    N    Y    K    R    L    A
              379    cga  caa  caa  aca  gag  caa  tac  aac  aac  tac  aaa  cga  tta  gca
                     T    R    Y    G    V    A    K    A    A    I    I    K    I    S
              421    aca  aga  tac  gga  gta  gca  ctc  gct  gca  atc  att  ctc  ata  tcc
                     I    W    G    P    H    R    D    K    R    V    G    E    W    L
              463    atc  tgg  ggg  cct  cat  cgt  gac  aag  cgt  gta  gga  gaa  tgg  ctc
                     G    V    K    K    W    R    L    W    D    A    W    L    N    Y
              505    ggt  gtc  aag  aag  tgg  aga  ttg  tgg  gat  gca  tgg  ttg  aac  tat
                     V    G    F    T    V    L    K    D    N    G    D    D    D    H
              547    gtt  gga  ttc  act  gta  cta  aag  gac  aat  gga  gat  gat  gac  cac
                     T    I    I    E    T    N    P    H    S    A    I    P    N    Q
              589    aca  ata  ata  caa  acg  aat  cca  cac  tca  gca  ata  ccc  aat  caa
                     E    E    F    D    I    H    T    S    P    S    I    F    A    F
              631    gaa  gag  ttt  gac  ata  cac  aca  tct  cca  tca  atc  ttc  gca  ttc
                     V    P    H    G    I    F    P    F    G    L    A    F    S    C
              673    gta  ccc  cac  ggc  atc  ttt  cct  ttc  gga  ctc  gcc  ttt  tca  tgt
                     L    P    E    R    G    H    E    Q    T    W    G    L    F    R
              715    cta  ccc  gaa  cga  gga  cac  gaa  caa  aca  tgg  ggt  ctc  ttc  cga
                     P    V    V    A    T    A    T    K    L    F    P    L    V    R
              757    cca  gtc  gtt  gca  aca  gcc  acc  aaa  ctc  ttt  ccg  ctg  gta  cga
                     T    F    I    S    W    M    N    G    V    D    A    S    D    S
              799    acc  ttc  att  tct  tgg  atg  aac  gga  gtg  gat  gct  tcg  cgt  tcg
                     A    V    S    R    A    L    A    P    P    Y    T    S    D    H
              841    gcg  gtg  tct  cgt  gct  ctt  gct  cct  ccg  tat  acc  agt  gat  cat
                     P    G    R    V    G    V    S    P    G    G    I    A    E    M
              883    ccg  gga  aga  gtg  gga  gtt  tcg  ccc  ggt  ggt  att  gcc  gag  atg
                     F    E    T    Y    P    K    P    G    F    H    P    N    D    E
              925    ttt  gag  acg  tat  cca  aag  ccg  ggg  ttt  cat  cct  aat  gac  gag
                     A    A    L    K    D    R    N    G    L    F    K    L    A
              967    gca  gca  ttg  tta  aaa  gat  cgg  aat  gga  ttg  ttc  aag  ctt  gcg
                     M    K    H    K    L    P    I    V    P    V    Y    C    F    G
             1009    atg  aaa  cac  aag  ctg  ccg  att  gtt  ccg  gtg  tac  tgc  ttt  gga
                     A    T    K    M    L    R    R    V    Q    L    P    A    F    V
             1051    gct  aca  aag  atg  ttg  aga  cga  gtg  caa  tta  cct  gcg  ttt  gtg
                     E    T    L    S    R    M    L    K    I    S    L    C    L    F
             1093    gag  acg  ttg  agc  aga  atg  ctc  aag  atc  agt  ctt  tgt  tta  ttc
```

FIG. 1B

```
           F    G    K    L    G    L    P    I    P    F    R    Q    R    L
    1135   ttt  gga  aag  ctt  ggg  ttg  cct  att  cct  ttc  cga  cag  cgg  ctg
           M    Y    V    M    G    K    T    L    F    P    P    L    P    R
    1177   atg  tat  gtc  atg  ggc  aag  acg  ttg  ttt  cct  cct  ctg  ccg  aga
           D    G    V    N    T    S    M    M    E    G    G    E    E    F
    1219   gat  ggc  gtg  aac  act  tct  atg  atg  gaa  gga  gga  gaa  gaa  ttt
           D    G    R    V    Q    E    M    H    D    A    F    C    N    E
    1261   gat  gaa  cga  gtg  caa  gag  atg  cat  gat  gca  ttc  tgc  aat  gag
           I    T    R    I    F    E    R    N    K    D    H    Y    G    W
    1303   ata  act  cgc  atc  ttc  gag  cga  aac  aaa  gac  cac  tac  ggt  tgg
           G    N    K    N    L    R    L    V
    1345   ggt  aac  aaa  aac  ttg  aga  ctc  gta  tga  gag  tgt  gag  tga  tat 1387   tca  tat  gca  act  ctt  aac  tta  aag  cca  cag  acc  aca  cag  gca 1429   caa  a
```

FIG. 2A

```
TpDGA2        1    MTTKKRPKPRHKHLPPGVEVLVSPPPYEVCTLVDRLLVYA

TpDGA2       41    SSLIVVGSPVWFYGGIIYFYRKWKLYRSKAAATFAARHES

TpDGA2       81    GGGGASSTVRCRGTRQRTSSDDGNYTSSTGESSQEMNEQE

TpDGA2      121    TQTQSHRQQTEQYNNYKRLATRYGVAKAAIIKISIWGPHR
37182187      1                                             PKK

TpDGA2      161    DKRVGEWLGVKKWRLWDAWLNYVGFTVLKDNGDDD---HT
37182187      4    GGRRSQW--VRNWAVWRHFANYFPVTLIKE-FDLDPKGNY
50541689      1      RRSQW--VRNWAVWRYFRDYFPIQLVKT-------HN
74623358      1             VRKLPLWKHFANYFPVTLIKE-FDLDPKGNY

TpDGA2      201    IIETNPHSAIPNQEEFDIHTSPS-IFAFVPHGIFPFG---
37182187     44    LLTTRNY----------------IFGYHPHGIMGLG---
50541689     41    LLTSRNY----------------IFGYHPHGIMGLG---
74623358     41    IMSYHPHGII-----------S-MAAFANFATEATG---
74623359      1              KEADLDPSKNYIFGYHPHGIISMGSF-
86279638      1                        VFGYEPHSVFPIGVMI
62825813      1                        VFGYEPHSVFPLG---

TpDGA2      241    LAFSCLPERGHE--QTWGLFRPVVATATKL-F--PLVRTF
37182187     84    -AFCNFSTEATEVSKKFPGIRPYLATLAGN-FRMPVLREY
50541689     81    -AFCNFSTEATEVSKKFPGIRPYLATLAGN-FRMPVLREY
74623358     81    FS--------E--QYPGIVPSLLTLASNFRL--PLYRDF
74623359     41    CTFST-NATGFD--DLFPGIRPSLLTLTSN-FNIPLYRDY
86279638     41    LSLGLIPLPN---------IKFLASSAVFY-T--PFLRHI
62825813     41    V--SVLSDHFAV--LPLPKMKVLASNAVFR-T--PVLRHI

TpDGA2      281    ISWMNGVDASDSAVSRALAPPYTSDHPGR-VGVSPGGIAE
37182187    124    LMSGGICPVSRDTIDYLLSKNGSGN---A-IIIVVGGAAE
50541689    121    LMSGGICPVNRDTIDYLLSKNGSGN---A-IIIVVGGAAE
74623358    121    M-----MSLGMCSVSRHSCEAILRSGPGRSIVIVTGGASE
74623359     81    LMACGLCSVSKTSCQNIL----TKGGPGRSIAIVVGGASE
86279638     81    WSWCGLTPATRKNFVSLLSSGYSCI-------LVPGGVQE
62825813     81    WTWCGLTSATKKNFTALLASGYSCI-------VIPGGVQE

TpDGA2      321    MFETYPKPGFHPNDEAALKDRNGLFKIAMKHKLPIVPVY
37182187    164    SLSSMP------GKNAVTLRNRKGFVKLALRHGADLVPIY
50541689    161    SLSSMP------GKNAVTLRNRKGFVKLALRHGADLVPTY
74623358    161    SLSA------RPGTNDLTLKKRLGFIRLAIRNGASLVPIF
74623359    121    SLNA------RPGVMDLVLKRRFGFIKIAVQTGASLVPTI
86279638    121    TF--YMKQ----DSEIAFLKARRGFIRIAMQTGTPLVPVF
62825813    121    TF--YMKHG---SEIAFLKARRGFVRVAMEMGKPLVPVF
```

FIG. 2B

```
TpDGA2     361  CFGATKMLR--RVQ------LPA------FVETLSRMLKI
37182187   204  SFGENEVYK--QVI------FEEGSWGRWVQKKFQKYIGF
50541689   201  SFGENEVYK--QVI------FEEGSWGRWVQKKFQKYIGF
74623358   201  SFGENDIYE--QYDNKKGSLIWR------YQKWFQKITGF
74623359   161  SFGENELYE--QIESNENSKLHR------WQKKIQHALGF
86279638   161  CFGQMHTFKWWKPD------GEL------FMK-IARAIKF
62825813   161  CFGQSNVYKWWKPD------GEL------FMK-IARAIKF

TpDGA2     401  SLCL-----FFGK-------LGLPIPFRQRLMYVMGKTLF
37182187   244  APCI-----FHGRGLFSSDTWGL-VPYSKPITTVVGEPIT
50541689   241  APCI-----FHGRGL---------VPYSKPITTVVGEPI-
74523358   241  TVPLAHARGIFNY-------NAGGIPFRHPIVTVVGKPIA
74623359   201  TMPL-----FHGRGVFNYD-FGL-LPHRHPIYTIVGKPI-
86279638   201  TPTI-----FWGV-------LGTPLPFKNPMHVVGRPI-
62825813   201  SPIV-----FWGV-------LGSHLPLQRPMHVVVGKPI-

TpDGA2     441  PPLPRDGVNTSMMEGGEEFDGRVQEMHDAFCNEITRIFER
37182187   284  IP---------KLEHPTQQD--IDLYHTMYMEALVKLFDK
50541689   281  -TIPR-------LERPTQQD--IDYLHAMYVQALVKLFDQ
74623358   281  VPLLAEGET-------EPSEEQMHQVQAQYIESLQAIYDK
74623359   241  -PVPS-------IKYGQTKDEIIRELHDSYMHAVQDLYDR
86279638   241  ------EVKQNPQPTAEE----VAEVQREFIASLKNLFER
62825813   241  ---------EVKQNPQPTVEEVSEVQGQFVAALKDLFER

TpDGA2     481  NKDHYGWGNKNLRLV
37182187   324  HKTKFG
50541689   321  HKTKFG
74623358   321  YKDIY
74623359   281  YKDIYHKTKFG
86279638   281  HKARVGYSDLKLEI
62825813   281  HKARVGYADLTLEIL
```

FIG. 3A

```
  1  MTTKKRPKPRHKHLPPGVEVLVSPPPYEVCTLVDRLLVYA
 41  SSLIVVGSPVWFYGGIIYFYRKWKLYRSKAAATFAARHES
 81  GGGGASSTVRCRGTRQRTSSDDGNYTSSTGESSQEMNEQE
121  TQTQSHRQQTEQYNNYKRLATRYGVAKAAIIKISIWGPHR
161  DKRVGEWLGVRKWRLWDAWLNYVGFTVLKDNGDDDHTIIE
201  TNPHSAIPNQEEFDIHTSPSIFAFVPHGIFPFGLAFSCLP
241  ERGHEQTWGLFRPVVATATKLFPLVRTFISWMNGVDASDS
281  AVSRALAPPYTSDHPGRVGVSPGGIAEMFETYPKPGFHPN
321  DEAALLKDRNGLFKLAMKHKLPIVPVYCFGATKMLRRVQL
361  PAFVETLSRMLKISLCLFFGKLGLPIPFRQRLMYVMGKTL
401  FPPLPRDGVNTSMMEGGEEFDGRVQEMHDAFCNEITRIFE
441  RNKDHYGWGNKNLRLV
```

FIG. 3B

```
169   G    V    R    K    W    R    L    W    D    A    W    L    N    Y
505  ggt  gtc  agg  aag  tgg  aga  ttg  tgg  gat  gca  tgg  ttg  aac  tat
```

FIG. 4A

```
  1  MTTKKRPKPRHKHLPPGVEVLVSPPPYEVCTLVDRLLVYA
 41  SSLIVVGSPVWFYGGIIYFYRKWKLYRSKAAATFAARHES
 81  GGGGASSTVRCRGTRQRTSSDDGNYTSSTGESSQEMNEQE
121  TQTQSHRQQTEQYNNYKRLATRYGVAKAAIIKISIWGPHR
161  DKRVGEWLGVKKWRLWDAWLNYVGFTVLKDNGDDDHTIIE
201  TNPHSAIPNQEEFDIHTSPSIFAYVPHGIFPFGLAFSCLP
241  ERGHEQTWGLFRPVVATATKLFPLVRTFISWMNGVDASDS
281  AVSRALAPPYTSDHPGRVGVSPGGIAEMFETYPKPGFHPN
321  DEAALLKDRNGLFKLAMKHKLPIVPVYCFGATKMLRRVQL
361  PAFVETLSRMLKISLCLFFGKLGLPIPFRQRLMYVMGKTL
401  FPPLPRDGVNTSMMEGGEEFDGRVQEMHDAFCNEITRIFE
441  RNKDHYGWGNKNLRLV
```

FIG. 4B

```
211   E    E    F    D    I    H    T    S    P    S    I    F    A    Y
631  gaa  gag  ttt  gac  ata  cac  aca  tct  cca  tca  atc  ttc  gca  tac
```

FIG. 5A

```
  1  MTTKKRPKPRHKHLPPGVEVLVSPPPYEVCTLVDRLLVYA
 41  SSLIVVGSPVWFYGGIIYFYRKWKLYRSKAAATFAARHES
 81  GGGGASSTVRCRGTRQRTSSDDGNYTSSTGESSQEMNEQE
121  TQTQSHRQQTEQYNNYKRLATRYGVAKAAIIKISIWGPHR
161  DKRVGEWLGVKKWRLWDAWLNYVGFTVLKDNGDDDHTIIE
201  TNPHSAIPNQEEFDIHTSPSIFAFVPHGIFPFGLAFSCLP
241  ERGHEQTWGLFRPVVATATKLFPLVRTFISWMNGVDASDS
281  AVSRALAPPYTSDHPGRIGVSPGGIAEMFETYPKPGFHPN
321  DEAALLKDRNGLFKLAMKHKLPIVPVYCFGATKMLRRVQL
361  PAFVETLSRMLKISLCLFFGKLGLPIPFRQRLMYVMGKTL
401  FPPLPRDGVNTSMMEGGEEFDGRVQEMHDAFCNEITRIFE
441  RNKDHYGWGNKNLRLV
```

FIG. 5B

```
295   P    G    R    I   G    V    S    P    G    G    I    A    E    M
883   ccg  gga  aga  atc gga  gtt  tcg  ccc  ggt  ggt  att  gcc  gag  atg
```

FIG. 6A

```
  1  MTTKKRPKPRHKHLPPGVEVLVSPPPYEVCTLVDRLLVYA
 41  SSLIVVGSPVWFYGGIIYFYRKWKLYRSKAAATFAARHES
 81  GGGGASSTVRCRGTRQRTSSDDGNYTSSTGESSQEMNEQE
121  TQTQSHRQQTEQYNNYKRLATRYGVAKAAIIKISIWGPHR
161  DKRVGEWLGVKKWRLWDAWLNYVGFTVLKDNGDDDHTIIE
201  TNPHSAIPNQEEFDIHTSPSIFAFVPHGIFPFGLAFSCLP
241  ERGHEQTWGLFRPVVATATKLFPLVRTFISWMNGVDASDS
281  AVSRALAPPYTSDHPGRVGVSPGGIAEMFETYPKPGFHPN
321  DEAALLKDRNGLFKLAMKHKLPLVPVYCFGATKMLRRVQL
361  PAFVETLSRMLKISLCLFFGKLGLPIPFRQRLMYVMGKTL
401  FPPLPRDGVNTSMMEGGEEFDGRVQEMHDAFCNEITRIFE
441  RNKDHYGWGNKNLRLV
```

FIG. 6B

```
337    M    K    H    K    L    P    L   V    P    V    Y    C    F    G
1009   atg  aaa  cac  aag  ctg  ccg  ctt gtt  ccg  gtg  tac  tgc  ttt  gga
```

FIG. 7A

```
  1  MTTKKRPKPRHKHLPPGVEVLVSPPPYEVCTLVDRLLVYA
 41  SSLIVVGSPVWFYGGIIYFYRKWKLYRSKAAATFAARHES
 81  GGGGASSTVRCRGTRQRTSSDDGNYTSSTGESSQEMNEQE
121  TQTQSHRQQTEQYNNYKRLATRYGVAKAAIIKISIWGPHR
161  DKRVGEWLGVKKWRLWDAWLNYVGFTVLKDNGDDDHTIIE
201  TNPHSAIPNQEEFDIHTSPSIFAFVPHGIFPFGLAFSCLP
241  ERGHEQTWGLFRPVVATATKLFPLVRTFISWMNGVDASDS
281  AVSRALAPPYTSDHPGRVGVSPGGIAEMFETYPKPGFHPN
321  DEAALLKDRNGLFKLAMKHKLPIVPVYCFGATKMLRRVQL
361  PAFVKTLSRMLKISLCLFFGKLGLPIPFRQRLMYVMGKTL
401  FPPLPRDGVNTSMMEGGEEFDGRVQEMHDAFCNEITRIFE
441  RNKDHYGWGNKNLRLV
```

FIG. 7B

```
 365    K    T    L    S    R    M    L    K    I    S    L    C    L    F
1093    aag  acg  ttg  agc  aga  atg  ctc  aag  atc  agt  ctt  tgt  tta  ttc
```

FIG. 8A

```
  1  MTTKKRPKPRHKHLPPGVEVLVSPPPYEVCTLVDRLLVYA
 41  SSLIVVGSPVWFYGGIIYFYRKWKLYRSKAAATFAARHES
 81  GGGGASSTVRCRGTRQRTSSDDGNYTSSTGESSQEMNEQE
121  TQTQSHRQQTEQYNNYKRLATRYGVAKAAIIKISIWGPHR
161  DKRVGEWLGVKKWRLWDAWLNYVGFTVLKDNGDDDHTIIE
201  TNPHSAIPNQEEFDIHTSPSIFAFVPHGIFPFGLAFSCLP
241  ERGHEQTWGLFRPVVATATKLFPLVRTFISWMNGVDASDS
281  AVSRALAPPYTSDHPGRVGVSPGGIAEMFETYPKPGFHPN
321  DEAALLKDRNGLFKLAMKHKLPIVPVYCFGATKMLRRVQL
361  PAFVETLSRMLKISLCLFFGKLGLPIPFRQRLMYVMGKTI
401  FPPLPRDGVNTSMMEGGEEFDGRVQEMHDAFCNEITRIFE
441  RNKDHYGWGNKNLRLV
```

FIG. 8B

```
 393    M    Y    V    M    G    K    T    I    F    P    P    L    P    R
1177    atg  tat  gtc  atg  ggc  aag  acg  atc  ttt  cct  cct  ctg  ccg  aga
```

OIL COMPRISING DIACYLGLYCEROL ACYLTRANSFERASE 2 GENES AND PROTEINS ENCODED THEREBY FROM ALGAE

CROSS-REFERENCE TO RELATED APPLICATIONS

This application is a divisional of U.S. patent application Ser. No. 12/735,132, filed Nov. 4, 2010, pending, which application is a national phase entry under 35 U.S.C. §371 of International Patent Application PCT/US2008/013811, filed Dec. 16, 2008, designating the United States of America and published in English as International Patent Publication WO 2009/085169 A2 on Jul. 9, 2009, which claims the benefit under Article 8 of the Patent Cooperation Treaty and under 35 U.S.C. §119(e) to U.S. Provisional Patent Application Ser. No. 61/008,752 filed Dec. 21, 2007, for "DIACYLGLYCEROL ACYLTRANSFERASE 2 GENES AND PROTEINS ENCODED THEREBY FROM ALGAE," the disclosure of each of which is hereby incorporated herein in its entirety by this reference.

TECHNICAL FIELD

This disclosure relates generally to biotechnology and, more particularly, to genes useful for the genetic manipulation of plant characteristics. In certain embodiments, the disclosure relates to isolated and/or purified polypeptides and nucleic acids encoding diacylglycerol acyltransferase 2 (DGAT2) and methods of their use.

BACKGROUND

Oil seed crops are a significant agricultural commodity. Plant seed oils are major sources of essential polyunsaturated fatty acids for human diets and renewable feedstocks for chemical industries. The enzymes of the fatty acid synthase complex in the plastids of developing seeds are responsible for the biosynthesis of fatty acids that are channeled into the cytosolic acyl CoA pool to sustain triacylglycerol accumulation. Triacylglycerol (TAG) biosynthesis is located in the endoplasmic reticulum with glycerol 3 phosphate and fatty acyl CoAs as the primary substrates. There are three acyltransferases involved in the plant storage lipid bioassembly, namely, the glycerol 3 phosphate acyltransferase (GPAT, EC 2.3.1.15), the lyso phosphatidic acid acyltransferase (LPAT, EC 2.3.1.51) and the diacylglycerol acyltransferase (DGAT, EC 2.3.1.20). These three acyltransferases catalyze the stepwise acylation of the glycerol backbone with the final step being the acylation of sn-1,2-diacylglycerol (DAG) by DGAT into the formation of TAGs, a biochemical process generally known as the Kennedy pathway. DGAT-mediated acylation of the glycerol backbone to produce TAG has been suggested as the rate-limiting step in plant lipids accumulation. Thus, DGAT is a target in the genetic modification of plant lipid biosynthesis.

DISCLOSURE

Disclosed herein is a genus of polypeptides having at least 90% sequence identity to *T. pseudonana* diacylglycerol acyltransferase 2 (DGAT). These polypeptides may be used to alter the levels of polyunsaturated fatty acids in plants. Also disclosed are polypeptides comprising the catalytic diacylglycerol transferase domain of *Thalassiosira pseudonana* DGAT2, and polypeptides having at least 90% sequence identity to the catalytic diacylglycerol transferase domain of DGAT2. Further described are polynucleotide sequences that encode polypeptides having at least 90% sequence identity to *T. pseudonana* DGAT2, and polynucleotides encoding polypeptides with at least 90% identity to the diacylglycerol transferase domain of *T. pseudonana* DGAT2.

Also disclosed herein is an isolated and purified diacylglycerol acyltransferase 2 (DGAT) gene and cDNA sequences from *T. pseudonana*. Also disclosed is the full-length DGAT2 cDNA sequence from *T. pseudonana*, and cDNA sequences with at least 80% sequence identity to the DGAT2 cDNA. In some embodiments, these cDNA sequences may be contained within a vector. These polynucleotides may be used to modify the natural formation of triacylglycerols in plants in order to increase the yield of commercial plant oils, or to modify their composition to achieve specific commercial improvements of plants and plant products.

Also disclosed are other isolated and purified genes and cDNA sequences of the DGAT2 family from *T. pseudonana*, and from other species of algae, including *Chlamydomonas reinhardtii*, *Ostreococcus lucimarinus*, *Ostreococcus tauri*, and *Phaeodactylum tricornutum*. These polynucleotides may also be used to modify the natural formation of triacylglycerols in plants in order to increase the yield of commercial plant oils, or to modify their composition to achieve specific commercial improvements of plants and plant products.

A transgenic plant containing a nucleic acid construct is also disclosed. A method of transforming a cell or a plant is described; the method comprising introducing the isolated, purified or recombinant nucleic acid into the cell or plant. A process for producing a genetically transformed plant seed comprises introducing the nucleic acid into the plant seed. In some embodiments, these methods may be used for modifying plants to change their seed oil content.

Stated most generally, some examples disclose the isolation, purification and characterization of a DGAT2 gene from algae, and the utility of DGAT2 in the production of very long-chain polyunsaturated fatty acids. The foregoing will become more apparent from the following detailed description of several embodiments, which proceeds with reference to the accompanying figures.

BRIEF DESCRIPTION OF DRAWINGS

FIGS. 1A-1B depict the deduced amino acid sequence (SEQ ID NO:1) corresponding to the full-length DGAT2 cDNA sequence of *T. pseudonana* DGAT2 (SEQ ID NO:2).

FIGS. 2A-2B depict a sequence alignment between SEQ ID NO:1 (TpDGA2) and gi:37182187, gi:50541689, gi:74623358, gi:74623359, gi:86279638, and gi:62825813, which are all type 2 diacylglycerol acyltransferases. Amino acids common to four or more of the sequences are indicated in bold. The amino acid sequence comprising the catalytic diacylglycerol transferase domain of these type 2 diacylglycerol acyltransferases consists of residues: 236-365 (TpDGA2), 79-208 (gi:37182187), 76-205 (gi:50541689), 76-205 (gi:74623358), 34-165 (gi:74623359), 33-165 (gi:86279638), and 36-165 (gi:62825813).

FIG. 3A depicts one example of a polypeptide sequence homologous to SEQ ID NO:1 (SEQ ID NO:3).

FIG. 3B depicts a portion of a polynucleotide sequence with at least 90% homology to SEQ ID NO:2 and encoding a portion of the polypeptide of SEQ ID NO:3 (SEQ ID NO:4).

FIG. 4A depicts another example of a polypeptide sequence homologous to SEQ ID NO:1 (SEQ ID NO:5).

FIG. 4B depicts a portion of a polynucleotide sequence with at least 90% homology to SEQ ID NO:2 and encoding a portion of the polypeptide of SEQ ID NO:5 (SEQ ID NO:6).

FIG. 5A depicts another example of a polypeptide sequence homologous to SEQ ID NO:1 (SEQ ID NO:7).

FIG. 5B depicts a portion of a polynucleotide sequence with at least 90% homology to SEQ ID NO:2 and encoding a portion of the polypeptide of SEQ ID NO:7 (SEQ ID NO:8).

FIG. 6A depicts another example of a polypeptide sequence homologous to SEQ ID NO:1 (SEQ ID NO:9).

FIG. 6B depicts a portion of a polynucleotide sequence with at least 90% homology to SEQ ID NO:2 and encoding a portion of the polypeptide of SEQ ID NO:9 (SEQ ID NO:10).

FIG. 7A depicts another example of a polypeptide sequence homologous to SEQ ID NO:1 (SEQ ID NO:11).

FIG. 7B depicts a portion of a polynucleotide sequence with at least 90% homology to SEQ ID NO:2 and encoding a portion of the polypeptide of SEQ ID NO:11 (SEQ ID NO:12).

FIG. 8A depicts another example of a polypeptide sequence homologous to SEQ ID NO:1 (SEQ ID NO:13).

FIG. 8B depicts a portion of a polynucleotide sequence with at least 90% homology to SEQ ID NO:2 and encoding a portion of the polypeptide of SEQ ID NO:13 (SEQ ID NO:14).

DETAILED DESCRIPTION

I. Overview of Several Embodiments

Disclosed herein is the isolated and purified type 2 diacylglycerol acyltransferase (DGAT) of T. pseudonana. The surprising ability of this polypeptide to modify the synthesis of very long-chain polyunsaturated fatty acids (VLCPUFA) in other organisms, and cells from other organisms, is used to transform plants and plant seeds to yield transgenic plants and plant seeds with desirable fatty acid compositions. Included in this disclosure are polypeptides with DGAT2 activity having an amino acid sequence of at least 90% sequence identity to that of T. pseudonana DGAT2. In certain embodiments, these polypeptide sequences comprise, for example, SEQ ID NO:1, SEQ ID NO:3, SEQ ID NO:5, SEQ ID NO:7, SEQ ID NO:9, SEQ ID NO:11, or SEQ ID NO:13. Also disclosed are polypeptides comprising sequences with at least 90% sequence identity to the catalytic diacylglycerol acyltransferase domain of T. pseudonana DGAT2. In certain embodiments, these polypeptide sequences comprise, for example, SEQ ID NO:15, SEQ ID NO:17, or SEQ ID NO:19. The catalytic diacylglycerol acyltransferase domain of T. pseudonana DGAT2 is depicted in FIG. 2; it consists of amino acid residues 236-365 in the complete disclosed polypeptide sequence of T. pseudonana DGAT2.

Figure 10:
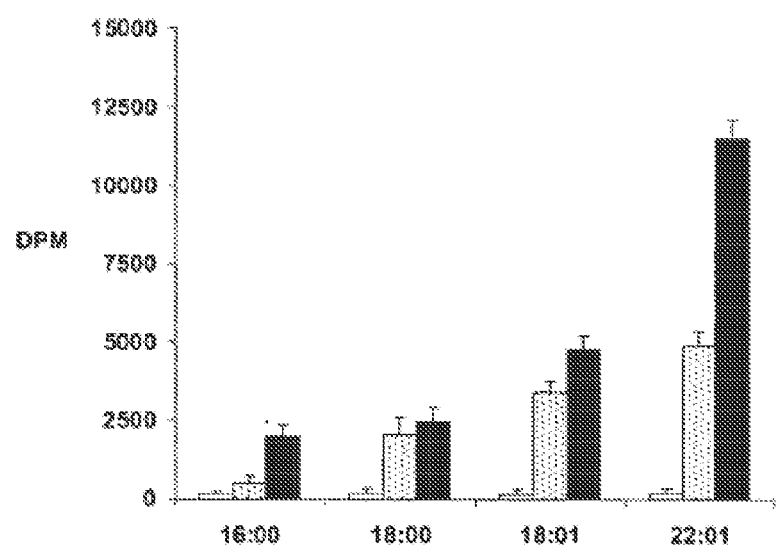
FIG. 10 shows DGAT activity in yeast mutant H1246 MAT α transformed with empty plasmid (pYES2.1 Con; empty bars), with the T. pseudonana DGAT2 cDNA (pYES:DGAT; stippled bars) and with the A. thaliana DGAT1 cDNA (solid black bars). The microsomal membrane fractions prepared from lysates of the induced yeast cells were assayed for DGAT activity using different $^{14}$C-labeled acyl-CoAs as acyl donors, and unlabeled sn-1,2 diolein as acceptor. The relative DGAT activity here was expressed as DPM (the amount of $^{14}$C-labeled substrates incorporated into TAGs). The results illustrate the substrate preference and relative activity of TpDGAT2 and AtDGAT1.
Figure 11:
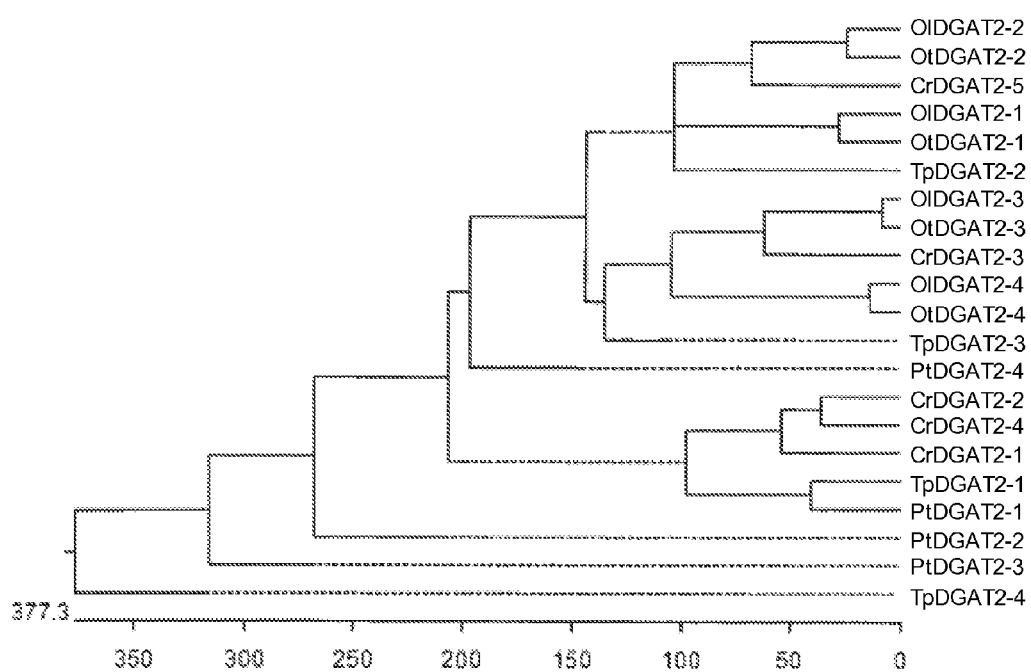
FIG. 11 depicts a homology comparison of the amino acid sequences of the TpDGAT2 (TpDGAT2-1) with its family members from T. pseudonana or from other algae species (Cr—Chlamydomonas reinhardtii, Ol-Ostreococcus lucimarinus, Ot—Ostreococcus tauri, or Pt—Phaeodactylum tricornutum). TpDGAT2 (TpDGAT2-1) shares 24%, 25%, and 17% sequence identity with its family members TpDGAT2-2, TpDGAT2-3, and TpDGAT2-4, respectively. Among different algae species TpDGAT2 (TpDGAT2-1) exhibits high sequence similarity with PtDGAT2-1 (48% sequence identity), and relatively high similarity with CrDGAT2-1, CrDGAT2-2, and CrDGAT2-4 (20%, 23%, and 24%, respectively).

The polypeptide of SEQ ID NO:15 comprises the diacylglycerol acyltransferase domain of T. pseudonana DGAT2. Some embodiments relate to isolated or purified polypeptides comprising sequences with at least about 90%, 91%, 92%, 93%, 94%, 95%, 96%, 97%, 98%, 99%, 99.5%, 99.6%, or 99.7% sequence identity to the isolated or purified polypeptide of SEQ ID NO:15, for example, SEQ ID NO:1. In particular embodiments, these polypeptides have diacylglycerol acyltransferase activity. Diacylglycerol acyltransferase activity can easily be determined by one skilled in the art by, for example, in vitro enzyme assay. This method is described in detail in Example 4, and typical results of this assay are shown in FIG. 10. As will be appreciated by persons skilled in the art, the disclosure also relates to substantially homologous DNA sequences from plants and algae encoding proteins comprising deduced amino acid sequences of 90% or greater identity to SEQ ID NO:15.

Other isolated or purified polypeptides from algae that are members of the DGAT2 family comprise amino acid sequences that are at least 90% identical to, for example, SEQ ID NO:25 (TpDGAT2-2), SEQ ID NO:27 (TpDGAT2-3), SEQ ID NO:29 (TpDGAT2-4), SEQ ID NO:31 (CrDGAT2-1), SEQ ID NO:33 (CrDGAT2-2), SEQ ID NO:35 (CrDGAT2-3), SEQ ID NO:37 (CrDGAT2-4), SEQ ID NO:39 (CrDGAT2-5), SEQ ID NO:41 (OlDGAT2-1), SEQ ID NO:43 (OlDGAT2-2), SEQ ID NO:45 (OlDGAT2-3), SEQ ID NO:47 (OlDGAT2-4), SEQ ID NO:49 (OtDGAT2-1), SEQ ID NO:51 (OtDGAT2-2), SEQ ID NO:53 (OtDGAT2-3), SEQ ID NO:55 (OtDGAT2-4), SEQ ID NO:57 (PtDGAT2-1), SEQ ID NO:59 (PtDGAT2-2), SEQ ID NO:61 (PtDGAT2-3), or SEQ ID NO:63 (PtDGAT2-4).

Some embodiments relate to isolated or purified nucleic acids (polynucleotides) that encode the polypeptides described above. The sequences of these polynucleotides may comprise, for example, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:26 (TpDGAT2-2), SEQ ID NO:28 (TpDGAT2-3), SEQ ID NO:30 (TpDGAT2-4), SEQ ID NO:32 (CrDGAT2-1), SEQ ID NO:34 (CrDGAT2-2), SEQ ID NO:36 (CrDGAT2-3), SEQ ID NO:38 (CrDGAT2-4), SEQ ID NO:40 (CrDGAT2-5), SEQ ID NO:42 (OlDGAT2-1), SEQ ID NO:44 (OlDGAT2-2), SEQ ID NO:46 (OlDGAT2-3), SEQ ID NO:48 (OlDGAT2-4), SEQ ID NO:50 (OtDGAT2-1), SEQ ID NO:52 (OtDGAT2-2), SEQ ID NO:54 (OtDGAT2-3), SEQ ID NO:56 (OtDGAT2-4), SEQ ID NO:58 (PtDGAT2-1), SEQ ID NO:60 (PtDGAT2-2), SEQ ID NO:62 (PtDGAT2-3), or SEQ ID NO:64 (PtDGAT2-4). In some embodiments, the polynucleotide sequences have a percentage identity with the bases of a disclosed nucleotide sequence of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% that encode a disclosed polypeptide. Several examples of such polynucleotides are SEQ ID NOS:21-24. As will be appreciated by the skilled practitioner, slight changes in nucleic acid sequence do not necessarily alter the amino acid sequence of the encoded polypeptide. It will be appreciated by persons skilled in the art that changes in the identities of nucleotides in a specific gene sequence that change the amino acid sequence of the encoded polypeptide may result in reduced or enhanced effectiveness of the genes and that, in some applications (i.e., antisense, co-suppression, or RNAi), partial sequences often work as effectively as full-length versions. The ways in which the gene sequence can be varied or shortened are well known to persons skilled in the art, as are ways of testing the effectiveness of the altered genes. In certain embodiments, effectiveness may easily be tested by, for example, conventional gas chromatography. All such variations of the genes are, therefore, included as part hereof.

Some embodiments relate to a vector containing an isolated or purified polynucleotide having at least 80% homology to SEQ ID NO:2, for example, SEQ ID NO:15, SEQ ID NO:16, SEQ ID NO:17, SEQ ID NO:18, SEQ ID NO:20, or SEQ ID NOS:21-24. Accordingly, there is provided a method for preparing a vector including a sequence selected from a group consisting of, for example, SEQ ID NO:2, SEQ ID NO:15, SEQ ID NO:16, SEQ ID NO:17, SEQ ID NO:18, SEQ ID NO:20, or SEQ ID NOS:21-24, or a part thereof, for introduction of the sequence or partial sequence in an antisense orientation, or the complement thereof, into a plant cell.

Certain embodiments relate to a vector containing polynucleotides having at least 80% homology to members of the DGAT2 family in algae. These vectors may comprise polynucleotide sequences of, for example, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ED NO:60, SEQ ID NO:62, or SEQ ID NO:64.

In some embodiments, the isolated and purified polynucleotides, and vectors comprising these isolated and purified polynucleotides, may be used to create transgenic plants that produce polypeptides with DGAT2 activity. Therefore, one embodiment relates to transgenic plants and plant seeds including an isolated or purified polynucleotide having at least 80% homology to SEQ ID NO:2, for example, a deoxyribonucleic acid molecule with the sequence of SEQ ID NO:2, SEQ ID NO:15, SEQ ID NO:16, SEQ ID NO:17, SEQ ID NO:18, SEQ ID NO:20, or SEQ ID NOS:21-24. Other embodiments relate to transgenic plants and plant seeds including an isolated or purified polynucleotide having at least 80% homology to another member of the DGAT2 family in algae, for example, a deoxyribonucleic acid molecule with the sequence of SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48; SEQ ID NO:50, SEQ ID NO:52, SEQ ID NO:54, SEQ ID NO:56, SEQ ID NO:58, SEQ ID NO:60, SEQ ID NO:62, or SEQ ID NO:64. Plants of these embodiments may have altered levels of polyunsaturated fatty acids in seeds as compared to levels in a plant lacking the nucleic acid construct. The fatty acids in the plant may be more than about 70% polyunsaturated fatty acids.

One embodiment comprises a method of producing such plants and plant seeds. The method comprises creating a nucleic acid construct comprising a polynucleotide encoding a polypeptide having at least 90% sequence identity to a polypeptide selected from the group consisting of SEQ ID NOS:1, 3, 5, 7, 9, 11, 13, 15, 17, and 19, or a polypeptide having at least 90% sequence identity to a polypeptide of the DGAT2 family in algae; for example, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, or SEQ ID NO:63; and introducing the construct into a plant. The method of this embodiment may be accomplished by any means known to one of ordinary skill in the art, by way of non-limiting example, *Agrobacterium*-mediated transformation. In specific embodiments, the method further comprises introducing a polynucleotide encoding a polypeptide with *Brassica* pyruvate dehydrogenase kinase activity, a polynucleotide encoding a polypeptide with diacylglycerol acetyltransferase activity, and/or a polynucleotide encoding a polypeptide with glycerol-3-phosphate dehydrogenase activity into the plant. This method may be practiced wherein the plant is selected from the group consisting of *Arabidopsis thaliana, Borago* spp., Canola, *Ricinus* spp., *Theobroma* spp., *Zea* spp., *Gossypium* spp, *Crambe* spp., *Cuphea* spp., *Linum* spp., *Lesquerella* spp., *Limnanthes* spp., Linola, *Tropaeolum* spp., *Oenothera* spp., *Olea* spp., *Elaeis* spp., *Arachis* spp., rapeseed, *Carthamus* spp., *Glycine* spp., *Soja* spp., *Helianthus* spp., *Nicotiana* spp., *Vernonia* spp., *Triticum* spp., *Hordeum* spp., *Oryza* spp., *Avena* spp., *Sorghum* spp., *Secale* spp., Brassicaceae, and other members of the plant family Gramineae.

In some embodiments, the method further comprises harvesting a seed from the plant including the introduced nucleic acid construct, and extracting oil from the harvested seed. Therefore, other embodiments include a plant produced by the method, and oil extracted from the plant produced by the method.

Some of the manipulations and deliverables that are possible using the DGAT2 gene or a part thereof, include, but are not limited to, the following: seeds with increased or decreased oil content, seeds containing oils with an enhanced very long-chain polyunsaturated fatty acid content, and plants exhibiting an enhanced or altered capacity to accumulate very long-chain polyunsaturated fatty acids.

II. Abbreviations

CaMV cauliflower mosaic virus
Cdna complementary DNA
CERV carnation etched ring virus
CrDGAT2 *Chlamydomonas reinhardtii* type 2 diacylglycerol transferase
DAG sn-1,2-diacylglycerol
DGAT diacylglycerol acyltransferase
DGAT2 type 2 diacylglycerol transferase
DHA docosahexaenoic acid
DNA deoxyribonucleic acid
EPA eicosapentaenoic acid
GPAT glycerol 3 phosphate acyltransferase
LPAT lyso phosphatidic acid acyltransferase OlDGAT2 *Ostreococcus lucimarinus* type 2 diacylglycerol transferase OtDGAT2 *Ostreococcus tauri* type 2 diacylglycerol transferase PCR polymerase chain reaction PtDGAT2 *Phaeodactylum tricornutum* type 2 diacylglycerol transferase RNA ribonucleic acid RNAi RNA interference RT-PCR reverse transcription PCR T35S CaMV 35S terminator TAG triacylglycerol TLC thin layer chromatography Tmas mannopine synthase terminator Tnos nopaline synthase terminator TpDGAT2 *T. pseudonana* type 2 diacylglycerol transferase TrbcS ribulose bisphosphate carboxylase small subunit termination region VLCPUFA very long-chain polyunsaturated fatty acids

III. Terms

In order to facilitate review of the various embodiments of the disclosure, the following explanations of specific terms are provided:

Complementary nucleotide sequence: "Complementary nucleotide sequence" of a sequence is understood as meaning any DNA whose nucleotides are complementary to those of sequences of the disclosure, and whose orientation is reversed (antiparallel sequence).

Degree or percentage of sequence homology: The term "degree or percentage of sequence homology" refers to degree or percentage of sequence identity between two sequences after optimal alignment. Percentage of sequence identity (or degree of identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

Homologous isolated and/or purified sequence: "Homologous isolated and/or purified sequence" is understood to mean an isolated and/or purified sequence having a percentage identity with the bases of a nucleotide sequence, or the amino acids of a polypeptide sequence, of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%. This percentage is purely statistical, and it is possible to distribute the differences between the two nucleotide sequences at random and over the whole of their length. Sequence identity can be determined, for example, by computer programs designed to perform single and multiple sequence alignments. It will be appreciated that this disclosure embraces the degeneracy of codon usage as would be understood by one of ordinary skill in the art. Furthermore, it will be understood by one skilled in the art that conservative substitutions may be made in the amino acid sequence of a polypeptide without disrupting the structure or function of the polypeptide. Conservative substitutions are accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins.

Isolated: As will be appreciated by one of skill in the art, "isolated" refers to polypeptides that have been "isolated" from their native environment.

Nucleotide, polynucleotide, or nucleic acid sequence: "Nucleotide, polynucleotide, or nucleic acid sequence" will be understood as meaning both a double-stranded or single-stranded DNA in the monomeric and dimeric (so-called in tandem) forms and the transcription products of the DNAs.

Sequence identity: Two amino acids or nucleotide sequences are said to be "dentical" if the sequence of amino acids or nucleotidic residues in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, *Ad. App. Math* 2:482 (1981), by the homology alignment algorithm of Neddleman and Wunsch, *J. Mol. Biol.* 48:443 (1970), by the search for similarity method of Pearson and Lipman, *Proc. Natl. Acad. Sci. U.S.A.* 85:2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

The definition of sequence identity given above is the definition that would be used by one of skill in the art. The definition by itself does not need the help of any algorithm, the algorithms being helpful only to achieve the optimal alignments of sequences, rather than the calculation of sequence identity.

From the definition given above, it follows that there is a well-defined and only one value for the sequence identity between two compared sequences, which value corresponds to the value obtained for the best or optimal alignment.

In the BLAST N or BLAST P "BLAST 2 sequence," software that is available in the web site blast(DOT)ncbi(DOT)nlm(DOT)nih(DOT)gov/Blast(DOT)cgi, and habitually used by the inventors and, in general, by the skilled man for comparing and determining the identity between two sequences, gap cost that depends on the sequence length to be compared is directly selected by the software (i.e., 11.2 for substitution matrix BLOSUM-62 for length>85).

Stringent hybridization: Hybridization under conditions of stringency with a nucleotide sequence is understood as meaning a hybridization under conditions of temperature and ionic strength chosen in such a way that they allow the maintenance of the hybridization between two fragments of complementary DNA. Homologs of the DGAT2 genes described herein obtained from other organisms, for example, plants, may be obtained by screening appropriate libraries that include the homologs, wherein the screening is performed with the nucleotide sequence of the specific DGAT2 genes disclosed herein, or portions or probes thereof, or identified by sequence homology search using sequence alignment search programs such as BLAST and FASTA.

IV. Modification of Fatty Acid Levels by DGAT2 from Algae

A. Overview

Recent studies on DGAT2 from tung tree and castor bean suggest that in plants containing unusual fatty acids, DGAT2 may play an important role in channeling unusual fatty acids into seed storage oils. While DGAT2 may be a potential target in the genetic modification of plant lipid biosynthesis in oilseeds, the recently characterized enzymes contributed to the utilization of conjugated fatty acid eleostearic acid (tung tree DGAT2) and ricinolenic acid (castor bean DGAT2), respectively. Neither enzyme (tung tree DGAT2 or castor bean DGAT2) is involved in the incorporation of commercially desirable long-chain omega-3 polyunsaturated fatty acids, eicosapentaenoic acid (EPA), and docosahexaenoic acid (DHA) in triacylglycerol (TAG).

The marine centric diatom algae *T. pseudonana* is able to produce and accumulate long-chain omega-3 polyunsaturated fatty acids EPA and DHA in TAG and is a good source of high-level very long-chain polyunsaturated fatty acid (VLCPUFA) accumulated oils. For this reason, the *T. pseudonana* diacylglycerol acyltransferase 2 (TpDGAT2) gene was investigated and characterized. Surprisingly, it was discovered that TpDGAT2, unlike DGAT2 from tung tree or castor bean, can efficiently incorporate very long-chain polyunsaturated fatty acids into TAG. Using the TpDGAT2 gene to search polynucleotide sequences from *T. pseudonana* and related species of algae, other members of the DGAT2 family in algae were identified. Thus, algal DGAT2 genes were determined to be useful in transgenic tools and for the modification of TAG composition and accumulation in seeds.

B. Polypeptides Homologous to *T. pseudonana* DGAT2 with Type 2 Diacylglycerol Transferase Activity Proteins that are homologous to full-length *T. pseudonana* DGAT2 can be found by searching protein databases, such as the NCBI protein database, with search engines, such as BLAST. They may also be identified by rational design. The process of rational design may comprise identifying conservative amino acid substitutions within the desired polypeptide sequence length, and making those substitutions in the encoded protein.

Searching the NCBI protein database with the full-length amino acid sequence of *T. pseudonana* DGAT2, BLASTP reveals polypeptides with significant sequence homology to TpDGAT2, several of which are shown aligned with TpDGAT2 in FIG. 2. The conserved type 2 diacylglycerol transferase domain is aligned in FIG. 2, and consists of amino acid residues 236-365 in TpDGAT2 and the corresponding residues from the other DGAT2 polypeptides depicted. The conserved type 2 diacylglycerol transferase domain is described within NCBI's conserved domain database, ncbi(DOT)nlm (DOT)nih(DOT)gov/Structure/cdd/wrpsb(DOT)cgi. Polypeptide sequences that are homologous to this conserved domain impart the type 2 diacylglycerol activity of TpDGAT2 to proteins wherein it is contained.

It is understood by those of ordinary skill in the art that polypeptides with homologous sequences may be designed to exhibit the same structure and function as their homologs. The skilled artisan is enabled to design homologous polypeptides to those specifically described in the examples of this disclosure by the sequence alignment of FIG. 2. Such homologous polypeptides may be those that contain conservative substitutions to polypeptides of the present disclosure, for example, the polypeptides of SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. Simple experimental assays that determine which homologous proteins exhibit substantially similar type 2 diacylglycerol transferase activity to TpDGAT2 are known to those skilled in the art. Such assays are not unduly time consuming, expensive, or technically difficult. For example, conventional gas chromatography may be used to detect TAG produced by TpDGAT2. Several of these assays are described in the detailed examples below.

C. Use of Nucleic Acid Molecules to Transform with DGAT2 Activity

It must be understood that disclosed embodiments do not include the genomic nucleotide sequences taken in their natural environment; that is to say, in the natural genome of *T. pseudonana*, *Chlamydomonas reinhardtii*, *Ostreococcus lucimarinus*, *Ostreococcus tauri*, or *Phaeodactylum tricornutum*. Some embodiments concern sequences that it has been possible to isolate, purify or partially purify, starting from separation methods such as, for example, ion-exchange chromatography, by exclusion based on molecular size, or by affinity, or, alternatively, fractionation techniques based on solubility in different solvents, or starting from methods of genetic engineering such as amplification, cloning, and subcloning, it being possible for the sequences to be carried by vectors.

Further included are nucleic acid molecules that hybridize to the above-disclosed sequences. Hybridization conditions may be stringent in that hybridization will occur if there is at least a 90%, 95% or 97% identity with the nucleic acid molecule that encodes the disclosed DGAT2 molecules. The stringent conditions may include those used for known Southern hybridizations such as, for example, incubation overnight at 420° C. in a solution having 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, followed by washing the hybridization support in 0.1×SSC at about 65° C. Other known hybridization conditions are well known and are described in Sambrook, et al., *Molecular Cloning: A Laboratory Manual*, Third Edition, Cold Spring Harbor, N.Y. (2001).

DNA isolation and cloning is well established. Similarly, DNA encoding an isolated enzyme may be inserted into a vector and transformed into yeast cells by conventional techniques. However, because no DGAT2 gene that can efficiently use VLCPUFA has been cloned, it has not been possible to address the possibility of genetic modifications by modulating DGAT2 activity. It was confirmed that DGAT2 is involved with TAG synthesis and utilizes VLCPUFA more efficiently than DGAT.

Nucleic acid molecules that code for DGAT2, for example, sequences having at least 80% identity to SEQ ID NO:2, SEQ ID NO:16, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, or SEQ ID NO:61, may be transformed into an organism, for example, a plant. Such homologous sequences are exemplified by SEQ ID NOS:21-24. As known in the art, there are a number of ways by which genes and gene constructs can be introduced into organisms, for example, plants, and a combination of transformation and tissue culture techniques have been successfully integrated into effective strategies for creating transgenic organisms, for example, crop plants. These methods have been described elsewhere (Potrykus, 1991; Vasil, 1994; Walden and Wingender, 1995; Songstad, et al., 1995), and are well known to persons skilled in the art. For example, one skilled in the art will certainly be aware that, in addition to *Agrobacterium*-mediated transformation of *Arabidopsis* by vacuum infiltration (Bechtold et al., 1993) or wound inoculation (Katavic, et al., 1994), it is equally possible to transform other plant and crop species, using *Agrobacterium* Ti-plasmid-mediated transformation (e.g., hypocotyl (DeBlock, et al., 1989) or cotyledonary petiole (Moloney, et al., 1989) wound infection), particle bombardment/biolistic methods (Sanford, et al., 1987; Nehra, et al., 1994; Becker, et al., 1994) or polyethylene glycol-assisted, protoplast transformation (Rhodes, et al., 1988; Shimamoto, et al., 1989) methods.

There are many examples of successful modifications to plant metabolism that have been achieved by genetic engineering to transfer new genes or to alter the expression of existing genes in plants. It is now routinely possible to introduce genes into many plant species of agronomic significance to improve crop performance (e.g., seed oil or tuber starch content/composition; meal improvement; herbicide, disease or insect resistance; heavy metal tolerance, etc.) (MacKenzie and Jain, 1997; Budziszewski, et al., 1996; Somerville, 1993; Kishore and Somerville, 1993).

As will also be apparent to persons skilled in the art, and as described elsewhere (Meyer, 1995; Dada, et al., 1997), it is possible to utilize plant, promoters to direct any intended up- or down-regulation of transgene expression using constitutive promoters (e.g., those based on CaMV35S), or by using promoters that can target gene expression to particular cells, tissues (e.g., napin promoter for expression of transgenes in developing seed cotyledons), organs (e.g., roots), to a particular developmental stage, or in response to a particular external stimulus (e.g., heat shock).

Promoters for use herein may be inducible, constitutive, or tissue-specific or have various combinations of such characteristics. Useful promoters include, but are not limited to, constitutive promoters, e.g., carnation etched ring virus (CERV), cauliflower mosaic virus (CaMV) 35S promoter, or more particularly the double enhanced cauliflower mosaic virus promoter, comprising two CaMV 35S promoters in tandem (referred to as a "Double 35S" promoter).

It may be desirable to use a tissue-specific or developmentally regulated promoter instead of a constitutive promoter in certain circumstances. A tissue-specific promoter allows for overexpression in certain tissues without affecting expression in other tissues. By way of illustration, a promoter used in overexpression of enzymes in seed tissue is an ACP promoter as described in PCT International Publication WO 92/18634, published Oct. 29, 1992.

The promoter and termination regulatory regions may be functional in the host plant cell and may be heterologous (that is, not naturally occurring) or homologous (derived from the plant host species) to the plant cell and the gene. Suitable promoters which may be used are described above.

The termination regulatory region may be derived from the 3' region of the gene from which the promoter was obtained or from another gene. Suitable termination regions that may be used are well known in the art and include *Agrobacterium tumefaciens* nopaline synthase terminator (Tnos), *A. tumefaciens* mannopine synthase terminator (Tmas) and the CaMV 35S terminator (T35S), the pea ribulose bisphosphate carboxylase small subunit termination region (TrbcS), or the Tnos termination region. Such gene constructs may suitably be screened for activity by transformation into a host plant via *Agrobacterium* and screening for increased isoprenoid levels.

Suitably, the nucleotide sequences for the genes may be extracted from the GenBank® (a registered trademark of the U.S. Department of Health and Human Services) nucleotide database and searched for restriction enzymes that do not cut. These restriction sites may be added to the genes by conventional methods such as incorporating these sites in PCR primers or by sub-cloning.

Preferably, a DNA construct for use herein is comprised within a vector, most suitably an expression vector adapted for expression in an appropriate host (plant) cell. It will be appreciated that any vector that is capable of producing a plant comprising the introduced DNA sequence will be sufficient.

Suitable vectors are well known to those skilled in the art and are described in general technical references such as Pouwels, et al., *Cloning Vectors. A Laboratory Manual*, Elsevier, Amsterdam (1986). Particularly suitable vectors include the Ti plasmid vectors.

Transformation techniques for introducing the DNA constructs into host cells are well known in the art and include such methods as micro-injection, using polyethylene glycol, electroporation, high velocity ballistic penetration, or *Agrobacterium*-mediated transformation. After transformation of the plant cells or plant, those plant cells or plants into which the desired DNA has been incorporated may be selected by such methods as antibiotic resistance, herbicide resistance, tolerance to amino-acid analogues, or using phenotypic markers.

Various assays may be used to determine whether the plant cell shows an increase in gene expression, for example, Northern blotting or quantitative reverse transcriptase PCR (RT-PCR). Whole transgenic plants may be regenerated from the transformed cell by conventional methods. Such transgenic plants having improved isoprenoid levels may be propagated and self-pollinated to produce homozygous lines. Such plants produce seeds containing the genes for the introduced trait and can be grown to produce plants that will produce the selected phenotype.

Particularly preferred plants for modification according to the present disclosure include *Arabidopsis thaliana*, borage (*Borago* spp.), Canola, castor (*Ricinus communis*) (*Ricinus* spp.), cocoa bean (*Theobroma cacao*) (*Theobroma* spp.), corn (*Zea mays*) (*Zea* spp.), cotton (*Gossypium* spp.), *Crambe* spp., *Cuphea* spp., flax (*Linum* spp.), *Lesquerella* spp. and *Limnanthes* spp., Linola, nasturtium (*Tropaeolum* spp.), *Oenothera* spp., olive (*Olea* spp.), palm (*Elaeis* spp.), peanut (*Arachis* spp.), rapeseed, safflower (*Carthamus* spp.), soybean (*Glycine* spp. and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), rye (*Secale* spp.) or other members of the plant family Gramineae.

Some embodiments are used to modify the yield or composition of oilseed produced from oilseed crops. Oilseed crops are plant species that are capable of generating edible or industrially useful oils in commercially significant yields, and include many of the plant species listed above. Such oilseed crops are well known to persons skilled in the art.

In one example, plants transformed with a nucleotide sequence that codes for a DGAT2 are grown. Seeds of the transgenic plants are harvested and fatty acids of the seeds are extracted. The extracted fatty acids are used for subsequent incorporation into a composition, for example, a pharmaceutical composition, a nutraceutical composition or a food composition.

In certain embodiments, other methods of enhancing or altering oil production may also be used with the plant to be transformed (e.g., incorporating, for expression in the plant, a nucleic acid sequence selected from the group comprising a nucleic acid sequence encoding a peptide having, for example, *Brassica* pyruvate dehydrogenase kinase activity (see, e.g., U.S. Pat. No. 7,214,859 to Marilla, et al. (May 8, 2007), U.S. Pat. No. 6,500,670 to Zou, et al. (December 2002), and U.S. Pat. No. 6,256,636 to Randall, et al. (July 2001), a nucleic acid sequence encoding a peptide having diacylglycerol acyltransferase activity (see, e.g., U.S. Pat. No. 7,015,373 and U.S. Pat. No. 6,500,670 to Zou, et al. (December 2002), and a nucleic acid sequence encoding a peptide having glycerol-3-phosphate dehydrogenase activity (see, e.g., U.S. Pat. No. 7,112,724 and combinations thereof).

Embodiments are susceptible to various modifications and alternative forms in addition to those specific examples described in detail herein. Thus, embodiments are not limited to the particular forms disclosed. Rather, the scope of the disclosure encompasses all modifications, equivalents, and alternatives falling within the following appended claims.

EXAMPLES

Example 1

DNA Manipulation

Standard methods and procedures were used for DNA preparation, plasmid propagation and isolation (Sambrook, et al., 1989). Sequencing was conducted on an Applied Biosystems Model 373A DNA Sequencing System using the Taq DYEDEOXY™ Terminator Cycle Sequencing Kit (Applied Biosystems, Inc.). The nucleotide and the deduced amino acid sequences were compared with sequences available in databanks using the BLAST program (Altschul et al., 1990). The DGAT2 clones were identified on the basis of homology with other fatty acid diacylglycerol acyltransferase genes in the NCBI nucleotide and protein databases as known in the art.

Example 2

In Vivo Triacylglycerol (TAG) Formed in Yeast Transformants by Expressing TpDGAT2

The DGAT2 gene was inserted into the pYES2.1 (Invitrogen). The construct was confirmed by sequencing and pYES2.1/TpDGAT2 was used to transform *Saccharomyces cerevisiae* strain H1246 MAT-α. This mutant strain is a quadruple mutant (DGAT-, PDAT-, ASAT-, ASAT2-). Plasmid DNA was isolated from putative transformants and the presence of the pYES2.1/TpDGAT2 was confirmed by Southern analysis. H1246 MAT-α transformants containing vector only (pYES2.1) were used as controls. H1246 MAT-α transformed with *Arabidopsis thaliana* DGAT1 served as a positive control.

Single colonies were cultured overnight in 20 mL of SD medium (synthetic Dextrose medium with glucose and without uracil, as described by Ausubel, et al., 1995, Vol. 2, p. 13.1.3) on a rotary shaker (270 rpm) at 28° C. Cells were pelleted from the overnight culture and resuspended in 50 mL of medium for induction of expression (SD medium containing galactose and without uracil). Cells were reincubated at 28° C., with shaking at 270 rpm, and harvested after four to six hours. GAL-induced yeast transformants were harvested by centrifugation at 5000 rpm for 5 minutes and resuspended in 100 mM Hepes NaOH, pH 7.4, containing 1 mM EDTA and 1 mM DTT.

Figure 9:
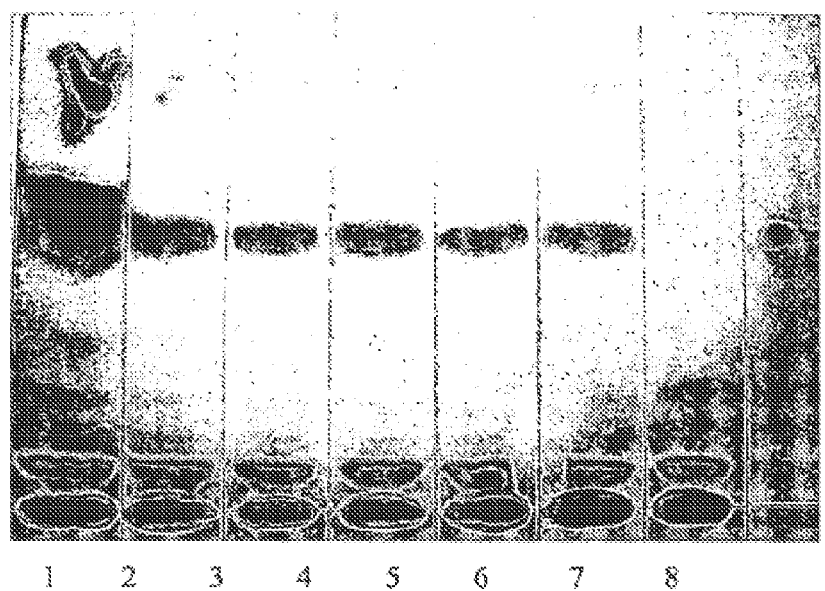
FIG. 9 depicts thin layer chromatography (TLC) analysis of TAG produced by expressing TpDGAT2 and AtDGAT1 in yeast mutant H1246 MAT α (DGAT, PDAT, ASAT1⁻, ASAT2⁻, which is deficient in TAG formation). Lane 1 represents the expression of AtDGAT1; Lanes 2-6 represent the expression of TpDGAT2. Clear TAG (triacylglycerol) bands were observed in lanes 2-6. Lane 8 represents an empty vector (pYES2.1) control, and there is no TAG (triacylglycerol) band in this lane. The lane on the right of lane 8 was loaded with a TAG standard, which can be used as a TAG marker.

Referring to FIG. 9, no TAG was produced in the empty vector, negative control (lane 8) while the positive control (lane 1) showed a TAG band. Each of the DGAT2-containing vectors (lanes 2-6) showed a TAG band, which confirmed that DGAT2 has the capacity to synthesize TAG. The lane on the right of lane 8 was loaded with a TAG standard, which was used as a TAG marker.

Example 3

Substrate Preference of TpDGAT2

Cell lysates were prepared using acid-washed glass beads as described by Ausubel, et al. (1995). Protein in yeast lysates was measured using the Bradford (1976) assay, protein levels in each lysate were normalized, and aliquots (250 μg protein) were assayed for DGAT2 activity.

DGAT assays were conducted at pH 7.4, with shaking at 100 revolutions/minute in a water bath at 30° C. for 10 minutes. Assay mixtures (0.5 ml final volume) contained 100 μg lysate protein, 90 mM HEPES-NaOH, 200 μM sn-1,2 diolein, and 18 μM $^{14}$C Acyl-CoAs (specific activity 2 nCi/nmol) as the acyl donor. The $^{14}$C-labeled TAGs were isolated by TLC on silica gel G plates developed in hexane:diethyl ether:acetic acid (70:30:1 v/v/v/), the radiolabeled TAG bands visualized on a Bioscan AR-2000 radio-TLC scanner using Win-Scan 2D® software (Bioscan Inc., Washington, D.C., USA) and the bands scraped and quantified as described by Taylor et al. (1991).

Example 4

Fatty Acid Composition of TpDGAT2 Transformants

*S. cerevisiae* strain H1246 MAT-α was transformed with *A. thaliana*/pYES2.1 or *T. pseudonana*/pYES2.1. Transformants were grown for three days at 28° C. and induced by galactose. The transformants were either treated with nothing (control), 50 μM DHA or 150 μM DHA. The fatty acid profile of three transformants containing AtDGAT1/pYES2.1 and three transformants containing TpDGAT2/pYES2.1 are shown in Table 1, based on conventional gas chromatography analysis.

Fatty acids are identified as 16:0, 16:1, 18:0, 18:1 (oleic acid), and 22:6 (DHA); and the composition of each is presented as a percentage of the total fatty acids. Expression of DHA increased from zero in the control strain to 6.01% in the 150 μM TpDGAT2/pYES2.1 and was more than double that of 150 μM AtDGAT/pYES2.1 (Table 1). These results further confirm that TpDGAT2 utilizes DHA fatty acids more efficiently than DGAT1.

In terms of fatty acid composition, the mutant lines containing DGAT2 cDNA showed a decrease in the total saturates, and increases in the unsaturates as shown in Table 1. Such changes are all toward a "healthier" oil profile and can be applied directly to canola, other oilseeds in the Brassicaceae and other edible oil crops to produce similar oil composition improvements.

TABLE 1

Fatty Acid Composition of TAG Expressed by DGAT2 and DGAT1 in Yeast Mutant H1246 MAT - α.

| Treatment | % 16:0 | % 16:1 | % 18:0 | % 18:1 | % 22:6 | % Sats | % Unsats |
|---|---|---|---|---|---|---|---|
| AtDGAT/ pYES2.1 - no feeding | 13.93 | 35.71 | 17.84 | 32.51 | 0.00 | 31.78 | 68.22 |
| AtDGAT/ pYES2.1 - 50 μM DHA | 19.68 | 27.54 | 16.51 | 34.82 | 1.46 | 36.18 | 62.36 |

TABLE 1-continued

Fatty Acid Composition of TAG Expressed by DGAT2
and DGAT1 in Yeast Mutant H1246 MAT - α.

| Treatment | % 16:0 | % 16:1 | % 18:0 | % 18:1 | % 22:6 | Fatty acid composition % Sats | % Unsats |
|---|---|---|---|---|---|---|---|
| AtDGAT/ pYES2.1 - 150 μM DHA | 19.24 | 27.83 | 15.21 | 35.08 | 2.63 | 34.45 | 62.91 |
| TpDGAT2/ pYES2.1 - no feeding | 10.03 | 30.23 | 13.83 | 45.90 | 0.00 | 23.87 | 76.13 |
| TpDGAT2/ pYES2.1 - 50 μM DHA | 6.43 | 35.39 | 8.49 | 45.07 | 4.62 | 14.92 | 80.47 |
| TpDGAT2/ pYES2.1 - 150 μM DHA | 5.77 | 31.73 | 11.57 | 44.93 | 6.01 | 17.34 | 76.66 |

Example 5

Over-Expression of the DGAT2 cDNA in Wild Type
*A. thaliana*

The full-length DGAT2 cDNA is used as a template for PCR amplification. A fragment is excised by restriction endonuclease digestion and ligated into the corresponding sites of a vector. The construct integrity is confirmed by sequencing.

The vector is introduced into *A. tumefaciens*, used to transform wild type *A. thaliana*, and is progeny analyzed.

Example 6

Construction of DGAT2 cDNA Plant Transformation
Vector for Seed-Specific Expression The full-length DGAT2 cDNA is used as a template for PCR amplification with primers to provide new restriction sites on each end of the sequence. The PCR profile is as follows: 94° C. 1 minute; 30 cycles of 94° C. 30 seconds, 55° C. 30 seconds, 72° C. 1 minute; and 72° C. 5 minutes. The PCR product is then ligated into the PCR 2.1 vector (Invitrogen). A fragment is excised and ligated into the corresponding sites of a vector. The construct integrity is confirmed by sequencing.

Example 7

Transformation of *Agrobacterium* with Plant DGAT2
Vector Constructs

Electrocompetent *Agrobacterium* cells, GV3101 (pMP90) strain, are prepared as follows: An *Agrobacterium* culture is grown 24 to 48 hours in 2YT, and when the absorbance at 600 nm has reached 0.5 to 0.7, the cells are chilled on ice and pelleted by centrifugation (5,000×g, 10 minutes in a GSA rotor at 4° C.). The pellet is washed in 1, 0.5, and 0.02 volumes of cold 10% sterile glycerol and resuspended in 0.01 volume of cold 10% glycerol. The electrocompetent cells are then frozen in liquid $N_2$ and stored at −70° C. The *Agrobacterium* cells are transformed by electroporation with 20-50 ng of transforming DNA according to the manufacturer's instructions, plated on a selective medium (LB with 50 μg/mL kanamycin) and incubated overnight at 28° C. Single transformed cells are grown overnight (28° C., 225 r.p.m.) in 5 mL LB with 50 μg/mL Kanamycin and 25 μg/mL Gentamycin. DNA extraction and purification are performed. The fidelity of the construct is re-checked by DNA sequencing before plant transformation.

Example 8

Transformation of *Arabidopsis thaliana*

Seeds of *A. thaliana* are grown at 22° C. under fluorescent illumination (120 μE·m$^{-2}$ S$^{-1}$) in a 16 hour light/8 hour dark regime. Four to six plants are raised in a 10 cm$^2$ pot in moistened TERRA-LITE REDI-EARTH (W. R. Grace & Co. Canada Ltd., Ajax, ON, Canada). To prevent the soil mix in the pot from falling into the inoculation media, soil is mounded as a platform with seeds sown on top, and the whole pot covered by a nylon window screen and secured by a rubber band. Plants are vacuum infiltrated in an *Agrobacterium* suspension when the first flowers start opening.

To grow *Agrobacterium*, a 5 mL suspension in LB medium containing 50 μg/mL kanamycin and 25 μg/mL gentamycin is cultured overnight at 28° C. The day before infiltration, this "seed culture" is divided into four flasks containing 250 mL of LB medium supplemented with 50 μg/mL kanamycin and 25 μg/mL gentamycin. These cultures are grown overnight at 28° C. The next morning after the absorbance at 600 nm is checked (approximately=1.0), the cells are harvested by centrifugation (5,000×g, 10 minutes in a GSA rotor at room temperature) and resuspended in the infiltration medium (sucrose 5%; Silwet-77 0.005% in water) to obtain an optical density at 600 nm of 0.8.

The *Agrobacterium* suspension is poured into a beaker and the potted plants inverted into the beaker so that the flowers and bolts are submerged. The beaker is placed into a large Bell jar and a vacuum is drawn using a vacuum pump, until bubbles form on the stem surfaces and the solution starts to bubble slightly, and then the vacuum is released rapidly. The necessary time and pressure will vary from one lab setup to the next, but good infiltration is visibly apparent as uniformly darkened, water soaked tissue. Pots are removed from the beaker, laid on their side in a plastic tray and covered with a plastic dome to maintain humidity. The following day, the plants are uncovered, set upright and allowed to grow for approximately four weeks in a growth chamber under continuous light conditions as described by Katavic, et al. (1995). When the siliques are mature and dry, seeds are harvested and are selected for positive transformants.

Example 9

Transformation of *Brassica napus*

Transformation is essentially carried out as described by Moloney, et al., 1989, *Plant Cell Reports* 8:238-242.

*A. tumifaciens* strain GV3101/pMP90 (C. Koncz and J. Schell, 1986, *Mol. Gen. Genet.* 204:383-396) is used for transformation studies. A stationary phase bacterial culture in LB broth (Difco, USA) (100 ml) is harvested by centrifugation and re-suspended in 10 ml fresh LB broth with 1% DMSO (dimethyl sulfoxide) (Sigma, USA) as a cryoprotectant. Aliquots of 200 μl are stored at −20° C. until used for transformation, wherein a bacterial aliquot is added to 2 ml Brain Heart Infusion Broth (Difco, USA) containing 2% sucrose, 50 μM acetosyringone, pH 5.6 and incubated overnight at 28° C. Bacterial cell density is approximately 1×10$^9$ cells per ml.

Cotyledonary explants are exposed to *Agrobacterium* containing the plant transformation vector according to the method of Moloney, et al. (1989), *Plant Cell Rep.* 8:238-242. The cut surface of the petiole of the explants is briefly submerged into the bacterial culture. The explants are inserted into co-cultivation medium such that the cut surface is in contact with the medium. Ten explants are placed in each 100×15 mm Petri plate. Co-cultivation plates are sealed with STRETCH'N SEAL™ plastic wrap. Plates are incubated for three days in a growth cabinet with temperature and photoperiod conditions, as above, with respect to the seed germination step. The explants are then transferred to selection medium.

After 3 to 4 weeks in the selection medium, regenerating green shoots (putative transformants) are excised and transferred to fresh selection medium for continued growth. When shoots attain a length of 1.5-2.0 cm, they are transferred to rooting medium. Putative transgenic shoots are screened for expression of the gus gene essentially as described by R. A. Jefferson (1987), *Plant Mol. Biol. Rep.* 5:387-405. The presence of blue staining is regarded as evidence of transformation.

Confirmation of transformation is established by selection on kanamycin, Southern blots, PCR (Polymerase Chain Reaction) and progeny analysis.

Example 10

Selection of Putative Transformants (Transgenic Plants) and Analysis of Transgenic Plants For each construct, seeds are harvested in bulk. Seeds are surface sterilized by submerging them in a solution containing 20% bleach and 0.01% TRITON® X-100 for 20 minutes, followed by three rinses with sterile water. Sterilized seeds are plated by re-suspending them in sterile 0.1% phytagar at room temperature (about 1 mL phytagar for every 500-1000 seeds), and applying a volume containing 2,000-4,000 seeds onto 150×15 mm kanamycin selection plate. Plates are incubated for two days in the cold without light, and grown for seven to ten days in a controlled environment (22° C. under fluorescent illumination (120 μE·m$^{-2}$ s$^{-1}$) in a 16-hour light/8-hour dark regime). The selection media contains ½ MSG medium, 0.8% phytagar, 3% sucrose, 50 mg/mL kanamycin and 50 mg/mL Timentin. Petri dishes and lids are sealed with a MICROPORE™ surgical tape (3M Canada, London, ON, Canada). After seven to ten days, drug-resistant plants that have green leaves and well-established roots within the medium are identified as transformants and at the three- to five-leaf stage, selected transformants are transplanted into flats filled with heavily moistened soil mix. Transformants are grown to maturity and mature seeds ($T_2$ generation as defined in Katavic, et al. (1994)) are harvested from individual plants, and further analyzed.

Genomic DNA is isolated from individual $T_1$ plants. PCR amplification is performed to confirm the presence of the cDNA or the gene, respectively, in the $T_1$ transformants. Southern analysis is performed to select the transformants containing a single copy of the inserted fragment. DNA samples are digested with restriction enzymes, resolved by electrophoresis on a 1% agarose gel, and Southern blotting is performed using a nylon filter (Hybond-N+, Amersham). The DGAT2 cDNA fragment, labeled with α-[$^{32}$P] dCTP (NEN/DuPont) is used as a probe. Hybridization is performed at 60° C. The filter is then exposed to Kodak X-OMAT-AR

REFERENCES

Ausubel F. M., R. Brent, R. E. Kingston, D. D. Moore, J. G. Seidman, J. A. Smith, and K. Stuhl, eds (1995). *Current Protocols in Molecular Biology*, Vols. 1, 2, and 3. Wiley, New York.

Bechtold N., J. Ellis, and G. Pelletier (1993). In planta *Agrobacterium*-mediated gene transfer by infiltration of adult *Arabidopsis thaliana* plants. C. R. Acad. Sci. Paris, *Sciences de la vie/Life Sciences* 316:1194-1199.

Becker D., R. Brettschneider and H. Lorz (1994). Fertile transgenic wheat from microprojectile bombardment of scutellar tissue. *Plant J.* 5:299-307.

Bradford M. M. (1976). A rapid and sensitive method for the quantification of microgram quantities of protein utilizing the principle of protein-dye binding. *Anal. Biochem.* 72:248-254.

Budziszewski G. J., K. P. C. Croft, and D. F. Hildebrand (1996). Uses of biotechnology in modifying plant lipids. *Lipids* 31:557-569.

Datla R., J. W. Anderson, and G. Selvaraj (1997). Plant promoters for transgene expression. *Biotechnology Annual Review* 3:269-296.

DeBlock M., D. DeBrouwer, and P. Tenning (1989). Transformation of *Brassica napus* and *Brassica oleracea* using *Agrobacterium tumefaciens* and the expression of the bar and neo genes in the transgenic plants. *Plant Physiol.* 91:694-701.

Jefferson R. A. (1987). Assaying chimeric genes in plants: The GUS gene fusion system. *Plant Mol. Biol. Rep.* 5:387-405.

Katavic V., G. W. Haughn, D. Reed, M. Martin, and L. Kunst (1994). In planta transformation of *Arabidopsis thaliana*. *Mol. Gen. Genet.* 245:363-370.

Katavic V., D. W. Reed, D. C. Taylor, E. M. Giblin, D. L. Barton, J.-T. Zou, S. L. MacKenzie, P. S. Covello, and L. Kunst (1995). Alteration of fatty acid composition by an EMS-induced mutation in *Arabidopsis thaliana* affecting diacylglycerol acyltransferase activity. *Plant Physiol.* 108:399-409.

Kishore G. M. and C. R. Somerville (1993). Genetic engineering of commercially useful biosynthetic pathways in transgenic plants. *Current Opinion in Biotechnology* 4:152-158.

Koncz C. and J. Schell (1986). The promoter of $T_L$-DNA gene 5 controls the tissue-specific expression of chimaeric genes carried by a novel type of *Agrobacterium* binary vector. *Mol. Gen. Genet.* 204:383-396.

MacKenzie S. L. and R. K. Jain (1997). Improvement of oils crops via biotechnology. *Recent Res. Dev. In Oil Chem.* 1:149-158.

Meyer P. (1995). Understanding and controlling transgene expression. *Trends in Biotechnology* 13:332-337.

Moloney M. M., J. M. Walker, and K. K. Sharma (1989). High-efficiency transformation of *Brassica napus* using *Agrobacterium* vectors. *Plant Cell Rep.* 8:238-242.

Nehra N. S., R. N. Chibbar, N. Leung, K. Caswell, C. Mallard, L. Steinhauer; M. Baga, and K. K. Kartha (1994). Self-fertile transgenic wheat plants regenerated from isolated scutellar tissues following microprojectile bombardment with two distinct gene constructs. *Plant J.* 5:285-297.

Potrykus I. (1991). Gene transfer to plants: Assessment of published approaches and results. *Annu. Rev. Plant Physiol. Plant Mol. Biol.* 42:205-225.

Rhodes C. A., D. A. Pierce, I. J. Mettler, D. Mascarenhas, and J. J. Detmer (1988). Genetically transformed maize plants from protoplasts. *Science* 240:204-207.

Sambrook J., E. F. Fritsch, and T. Maniatis (1989). *In Molecular Cloning, A Laboratory Manual,* 2nd edition. Cold Spring Harbor Laboratory Press.

Sanford J. C., T. M. Klein, E. D. Wolf, and N. Allen (1987). Delivery of substances into cells and tissues using a particle bombardment process. *J. Part. Sci. Technol.* 5:27-37.

Shimamoto K., R. Terada, T. Izawa, and H. Fujimoto (1989). Fertile transgenic rice plants regenerated from transformed protoplasts. *Nature* 338:274-276.

Somerville C. R. (1993). Future prospects for genetic modification of the composition of edible oils from higher plants. *Am. J. Clin. Nutr.* 58 (2 Suppl.): 270S-275S.

Songstad D. D., D. A. Somers, and R. J. Griesbach (1995). Advances in alternative DNA delivery techniques. *Plant Cell, Tissue and Organ Culture* 40:1-15.

Southern E. M. (1975). Detection of specific sequences among DNA fragments separated by gel electrophoresis. *J. Mol. Biol.* 98:503-517.

Taylor D. C., N. Weber, D. L. Barton, E. W. Underhill, L. R. Hogge, R. J. Weselake, and M. K. Pomeroy (1991). Triacylglycerol bioassembly in microspore-derived embryos of *Brassica napus* L. cv. Reston. *Plant Physiol.* 97:65-79.

Vasil I. K. (1994). Molecular improvement of cereals. *Plant Mol. Biol.* 25:925-937.

Walden R. and R. Wingender (1995). Gene-transfer and plant regeneration techniques. *Trends in Biotechnology* 13:324-331.

Zou J-T., V. Katavic, E. M. Giblin, D. L. Barton, S. L. MacKenzie, W. A. Keller, X. Hu, and D. C. Taylor (1997). Modification of seed oil content and acyl composition in the Brassicaceae by expression of a yeast sn-2 acyltransferase gene. *The Plant Cell* 9:909-923.

---

What is claimed is:

1. Oil from a transgenic oilseed plant, wherein the oil comprises a polynucleotide encoding a polypeptide comprising a peptide having at least 90% sequence identity to SEQ ID NO:15, wherein the encoded polypeptide has diacylglycerol acyltransferase activity.

2. The oil of claim 1, wherein the transgenic oilseed plant is produced by introducing into the plant a nucleic acid molecule comprising a heterologous promoter operably linked to the polynucleotide.

3. The oil of claim 1, wherein the polypeptide has at least 90% sequence identity to SEQ ID NO:1.

4. The oil of claim 1, wherein the polypeptide has the amino acid sequence of SEQ ID NO:1.

5. The oil of claim 1, wherein the transgenic oilseed plant is selected from the group consisting of *Arabidopsis thaliana*, *Borago* spp., Canola, *Ricinus* spp., *Theobroma* spp., *Zea* spp., *Gossypium* spp, *Crambe* spp., *Cuphea* spp., *Linum* spp., *Lesquerella* spp., *Limnanthes* spp., Linola, *Tropaeolum* spp., *Oenothera* spp., *Olea* spp., *Elaeis* spp., *Arachis* spp., rapeseed, *Carthamus* spp., *Glycine* spp., *Soja* spp., *Helianthus* spp., *Nicotiana* spp., *Vernonia* spp., *Triticum* spp., *Hordeum* spp., *Oryza* spp., *Avena* spp., *Sorghum* spp., *Secale* spp., Brassicaceae, and other members of the plant family Gramineae.

6. The oil of claim 1, wherein the oil comprises an amount of docosahexaenoic acid (DHA) that is greater than the amount of DHA in oil from an oilseed plant of the same species that does not comprise a polynucleotide encoding a polypeptide comprising a peptide having at least 90% sequence identity to SEQ ID NO:15.

7. The oil of claim 6, wherein the transgenic oilseed plant is selected from the group consisting of *Arabidopsis thaliana*, *Borago* spp., Canola, *Ricinus* spp., *Theobroma* spp., *Zea* spp., *Gossypium* spp, *Crambe* spp., *Cuphea* spp., *Linum* spp., *Lesquerella* spp., *Limnanthes* spp., Linola, *Tropaeolum* spp., *Oenothera* spp., *Olea* spp., *Elaeis* spp., *Arachis* spp., rapeseed, *Carthamus* spp., *Glycine* spp., *Soja* spp., *Helianthus* spp., *Nicotiana* spp., *Vernonia* spp., *Triticum* spp., *Hordeum* spp., *Oryza* spp., *Avena* spp., *Sorghum* spp., *Secale* spp., Brassicaceae, and other members of the plant family Gramineae.

8. A composition comprising the oil of claim 1, wherein the composition is a pharmaceutical composition, a nutraceutical composition, or a food composition.

9. Oil extracted from a plant comprising a nucleic acid molecule comprising a heterologous promoter operably linked to a polynucleotide encoding a polypeptide comprising a peptide having at least 90% sequence identity to SEQ ID NO:15, wherein the encoded polypeptide has diacylglycerol acyltransferase activity, and wherein the oil comprises the polynucleotide encoding the polypeptide.

10. The oil of claim 9, wherein the oil comprises an amount of docosahexaenoic acid (DHA) that is greater than the amount of DHA in oil from a plant of the same species that does not comprise a polynucleotide encoding a polypeptide comprising a peptide having at least 90% sequence identity to SEQ ID NO:15.

11. The oil of claim 9, wherein the transgenic oilseed plant is selected from the group consisting of *Arabidopsis thaliana*, *Borago* spp., Canola, *Ricinus* spp., *Theobroma* spp., *Zea* spp., *Gossypium* spp, *Crambe* spp., *Cuphea* spp., *Linum* spp., *Lesquerella* spp., *Limnanthes* spp., Linola, *Tropaeolum* spp., *Oenothera* spp., *Olea* spp., *Elaeis* spp., *Arachis* spp., rapeseed, *Carthamus* spp., *Glycine* spp., *Soja* spp., *Helianthus* spp., *Nicotiana* spp., *Vernonia* spp., *Triticum* spp., *Hordeum* spp., *Oryza* spp., *Avena* spp., *Sorghum* spp., *Secale* spp., Brassicaceae, and other members of the plant family Gramineae.

12. A composition comprising the oil of claim 9, wherein the composition is a pharmaceutical composition, a nutraceutical composition, or a food composition.

* * * * *

SEQUENCE LISTING

```
<160> NUMBER OF SEQ ID NOS: 64

<210> SEQ ID NO 1
<211> LENGTH: 456
<212> TYPE: PRT
<213> ORGANISM: T. pseudonana

<400> SEQUENCE: 1

Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
            20                  25                  30

Val Asp Arg Leu Leu Val Tyr Ala Ser Ser Leu Ile Val Val Gly Ser
        35                  40                  45

Pro Val Trp Phe Tyr Gly Gly Ile Ile Tyr Phe Tyr Arg Lys Trp Lys
    50                  55                  60

Leu Tyr Arg Ser Lys Ala Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
            100                 105                 110

Ser Gln Glu Met Asn Glu Gln Glu Thr Gln Thr Gln Ser His Arg Gln
        115                 120                 125

Gln Thr Glu Gln Tyr Asn Asn Tyr Lys Arg Leu Ala Thr Arg Tyr Gly
    130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Lys Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
        195                 200                 205

Asn Gln Glu Glu Phe Asp Ile His Thr Ser Pro Ser Ile Phe Ala Phe
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
                245                 250                 255
```

```
Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
        275                 280                 285

Pro Tyr Thr Ser Asp His Pro Gly Arg Val Gly Val Ser Pro Gly Gly
        290                 295                 300

Ile Ala Glu Met Phe Glu Thr Tyr Pro Lys Pro Gly Phe His Pro Asn
305                 310                 315                 320

Asp Glu Ala Ala Leu Leu Lys Asp Arg Asn Gly Leu Phe Lys Leu Ala
                325                 330                 335

Met Lys His Lys Leu Pro Ile Val Pro Val Tyr Cys Phe Gly Ala Thr
            340                 345                 350

Lys Met Leu Arg Arg Val Gln Leu Pro Ala Phe Val Glu Thr Leu Ser
        355                 360                 365

Arg Met Leu Lys Ile Ser Leu Cys Leu Phe Phe Gly Lys Leu Gly Leu
        370                 375                 380

Pro Ile Pro Phe Arg Gln Arg Leu Met Tyr Val Met Gly Lys Thr Leu
385                 390                 395                 400

Phe Pro Pro Leu Pro Arg Asp Gly Val Asn Thr Ser Met Met Glu Gly
                405                 410                 415

Gly Glu Glu Phe Asp Gly Arg Val Gln Glu Met His Asp Ala Phe Cys
            420                 425                 430

Asn Glu Ile Thr Arg Ile Phe Glu Arg Asn Lys Asp His Tyr Gly Trp
        435                 440                 445

Gly Asn Lys Asn Leu Arg Leu Val
        450                 455

<210> SEQ ID NO 2
<211> LENGTH: 1432
<212> TYPE: DNA
<213> ORGANISM: T. pseudonana

<400> SEQUENCE: 2
atgacaacaa agaagcgtcc actacccccgt catctgcacc ttccacctgg agtagaagta      60
ctcgtctctc caccacccta cgaagtatgc acgctcgtcg acagattgtt ggtctacgcc     120
tcgtcgttga ttgtcgttgg atctcccgtt tggttctacg gaggcatcat ttattttttac    180 aggaagtgga agaagtatcg ttctcttgct gctgctactg aggctgcgag acatgagagt     240
ggtggcggtg gtgcatcgtc aacggttcgt tgcagaggta cacgtcaacg tacatcgtct     300
gatgacggca actacacatc gtcaactggc gaaagctcgc aagaaatgaa cgaacaagag     360
acacaaacac aatcacatcg acaacaaaca gagcaataca caactacaa cgattagca      420 acaagatacg gagtagcact cgctgcaatc attctcatat ccatctgggg gcctcatcgt     480
gacaagcgtg taggagaatg gctcggtgtc aagaagtgga gattgtggga tgcatggttg     540
aactatgttg gattcactgt actaaaggac aatggagatg atgaccacac aataatacaa     600
acgaatccac actcagcaat acccaatcaa gaagagtttg acatacacac atctccatca     660
atcttcgcat tcgtaccccca cggcatcttt cctttcggac tcgccttttc atgtctaccc     720
gaacgaggac acgaacaaac atggggtctc ttccgaccag tcgttgcaac agccaccaaa     780
ctctttccgc tggtacgaac cttcatttct tggatgaacg gagtggatgc ttcgcgttcg     840
gcggtgtctc gtgctcttgc tcctccgtat accagtgatc atccgggaag agtgggagtt     900
tcgcccggtg gtattgccga gatgtttgag acgtatccaa agccggggtt tcatcctaat     960
```

```
gacgaggcag cattgttaaa agatcggaat ggattgttca agcttgcgat gaaacacaag    1020
ctgccgattg ttccggtgta ctgctttgga gctacaaaga tgttgagacg agtgcaatta    1080
cctgcgtttg tggagacgtt gagcagaatg ctcaagatca gtctttgttt attctttgga    1140
aagcttgggt tgcctattcc tttccgacag cggctgatgt atgtcatggg caagacgttg    1200
tttcctcctc tgccgagaga tggcgtgaac acttctatga tggaaggagg agaagaattt    1260
gatgaacgag tgcaagagat gcatgatgca ttctgcaatg agataactcg catcttcgag    1320
cgaaacaaag accactacgg ttggggtaac aaaaacttga gactcgtatg agagtgtgag    1380
tgatattcat atgcaactct taacttaaag ccacagacca cacaggcaca aa             1432
```

<210> SEQ ID NO 3
<211> LENGTH: 456
<212> TYPE: PRT
<213> ORGANISM: Artificial
<220> FEATURE:
<223> OTHER INFORMATION: K171R mutant

<400> SEQUENCE: 3

```
Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
            20                  25                  30

Val Asp Arg Leu Leu Val Tyr Ala Ser Ser Leu Ile Val Gly Ser
        35                  40                  45

Pro Val Trp Phe Tyr Gly Gly Ile Ile Tyr Phe Tyr Arg Lys Trp Lys
    50                  55                  60

Leu Tyr Arg Ser Lys Ala Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
            100                 105                 110

Ser Gln Glu Met Asn Glu Gln Glu Thr Gln Thr Gln Ser His Arg Gln
        115                 120                 125

Gln Thr Glu Gln Tyr Asn Asn Tyr Lys Arg Leu Ala Thr Arg Tyr Gly
    130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Arg Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
        195                 200                 205

Asn Gln Glu Glu Phe Asp Ile His Thr Ser Pro Ser Ile Phe Ala Phe
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
                245                 250                 255

Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
        275                 280                 285
```

```
Pro Tyr Thr Ser Asp His Pro Gly Arg Val Gly Val Ser Pro Gly Gly
    290                 295                 300
Ile Ala Glu Met Phe Glu Thr Tyr Pro Lys Pro Gly Phe His Pro Asn
305                 310                 315                 320
Asp Glu Ala Ala Leu Leu Lys Asp Arg Asn Gly Leu Phe Lys Leu Ala
                325                 330                 335
Met Lys His Lys Leu Pro Ile Val Pro Val Tyr Cys Phe Gly Ala Thr
                340                 345                 350
Lys Met Leu Arg Arg Val Gln Leu Pro Ala Phe Val Glu Thr Leu Ser
                355                 360                 365
Arg Met Leu Lys Ile Ser Leu Cys Leu Phe Phe Gly Lys Leu Gly Leu
    370                 375                 380
Pro Ile Pro Phe Arg Gln Arg Leu Met Tyr Val Met Gly Lys Thr Leu
385                 390                 395                 400
Phe Pro Pro Leu Pro Arg Asp Gly Val Asn Thr Ser Met Met Glu Gly
                405                 410                 415
Gly Glu Glu Phe Asp Gly Arg Val Gln Glu Met His Asp Ala Phe Cys
                420                 425                 430
Asn Glu Ile Thr Arg Ile Phe Glu Arg Asn Lys Asp His Tyr Gly Trp
                435                 440                 445
Gly Asn Lys Asn Leu Arg Leu Val
    450                 455

<210> SEQ ID NO 4
<211> LENGTH: 1432
<212> TYPE: DNA
<213> ORGANISM: Artificial
<220> FEATURE:
<223> OTHER INFORMATION: K171R mutant

<400> SEQUENCE: 4
atgacaacaa agaagcgtcc actacccegt catctgcacc ttccacctgg agtagaagta      60
ctcgtctctc caccacccta cgaagtatgc acgctcgtcg acagattgtt ggtctacgcc     120
tcgtcgttga ttgtcgttgg atctcccgtt tggttctacg gaggcatcat ttattttac     180 aggaagtgga agaagtatcg ttctcttgct gctgctactg aggctgcgag acatgagagt     240
ggtggcggtg gtgcatcgtc aacggttcgt tgcagaggta cacgtcaacg tacatcgtct     300
gatgacggca actacacatc gtcaactggc gaaagctcgc aagaaatgaa cgaacaagag     360
acacaaacac aatcacatcg acaacaaaca gagcaataca caactacaa acgattagca     420 acaagatacg gagtagcact cgctgcaatc attctcatat ccatctgggg gcctcatcgt     480
gacaagcgtg taggagaatg gctcggtgtc aggaagtgga gattgtggga tgcatggttg     540
aactatgttg gattcactgt actaaaggac aatggagatg atgaccacac aataatacaa     600
acgaatccac actcagcaat acccaatcaa gaagagtttg acatacacac atctccatca     660
atcttcgcat tcgtaccccca cggcatcttt cctttcggac tcgccttttc atgtctaccc     720
gaacgaggac acgaacaaac atggggtctc ttccgaccag tcgttgcaac agccaccaaa     780
ctctttccgc tggtacgaac cttcatttct tggatgaacg gagtggatgc ttcgcgttcg     840
gcggtgtctc gtgctcttgc tcctccgtat accagtgatc atccgggaag agtgggagtt     900
tcgcccggtg gtattgccga gatgtttgag acgtatccaa agccggggtt tcatcctaat     960
gacgaggcag cattgttaaa agatcggaat ggattgttca agcttgcgat gaaacacaag    1020
ctgccgattg ttccggtgta ctgctttgga gctacaaaga tgttgagacg agtgcaatta    1080
```

-continued

```
cctgcgtttg tggagacgtt gagcagaatg ctcaagatca gtctttgttt attctttgga   1140
aagcttgggt tgcctattcc tttccgacag cggctgatgt atgtcatggg caagacgttg   1200
tttcctcctc tgccgagaga tggcgtgaac acttctatga tggaaggagg agaagaattt   1260
gatgaacgag tgcaagagat gcatgatgca ttctgcaatg agataactcg catcttcgag   1320
cgaaacaaag accactacgg ttggggtaac aaaaacttga gactcgtatg agagtgtgag   1380
tgatattcat atgcaactct taacttaaag ccacagacca cacaggcaca aa           1432
```

<210> SEQ ID NO 5
<211> LENGTH: 456
<212> TYPE: PRT
<213> ORGANISM: Artificial
<220> FEATURE:
<223> OTHER INFORMATION: F224Y mutant

<400> SEQUENCE: 5

```
Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
            20                  25                  30

Val Asp Arg Leu Leu Val Tyr Ala Ser Ser Leu Ile Val Val Gly Ser
        35                  40                  45

Pro Val Trp Phe Tyr Gly Gly Ile Ile Tyr Phe Tyr Arg Lys Trp Lys
    50                  55                  60

Leu Tyr Arg Ser Lys Ala Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
            100                 105                 110

Ser Gln Glu Met Asn Glu Gln Glu Thr Gln Thr Gln Ser His Arg Gln
        115                 120                 125

Gln Thr Glu Gln Tyr Asn Asn Tyr Lys Arg Leu Ala Thr Arg Tyr Gly
    130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Lys Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
        195                 200                 205

Asn Gln Glu Glu Phe Asp Ile His Thr Ser Pro Ser Ile Phe Ala Tyr
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
                245                 250                 255

Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
        275                 280                 285

Pro Tyr Thr Ser Asp His Pro Gly Arg Val Gly Val Ser Pro Gly Gly
    290                 295                 300
```

```
Ile Ala Glu Met Phe Glu Thr Tyr Pro Lys Pro Gly Phe His Pro Asn
305                 310                 315                 320

Asp Glu Ala Ala Leu Leu Lys Asp Arg Asn Gly Leu Phe Lys Leu Ala
            325                 330                 335

Met Lys His Lys Leu Pro Ile Val Pro Val Tyr Cys Phe Gly Ala Thr
        340                 345                 350

Lys Met Leu Arg Arg Val Gln Leu Pro Ala Phe Val Glu Thr Leu Ser
    355                 360                 365

Arg Met Leu Lys Ile Ser Leu Cys Leu Phe Phe Gly Lys Leu Gly Leu
370                 375                 380

Pro Ile Pro Phe Arg Gln Arg Leu Met Tyr Val Met Gly Lys Thr Leu
385                 390                 395                 400

Phe Pro Pro Leu Pro Arg Asp Gly Val Asn Thr Ser Met Met Glu Gly
                405                 410                 415

Gly Glu Glu Phe Asp Gly Arg Val Gln Glu Met His Asp Ala Phe Cys
            420                 425                 430

Asn Glu Ile Thr Arg Ile Phe Glu Arg Asn Lys Asp His Tyr Gly Trp
        435                 440                 445

Gly Asn Lys Asn Leu Arg Leu Val
    450                 455

<210> SEQ ID NO 6
<211> LENGTH: 1432
<212> TYPE: DNA
<213> ORGANISM: Artificial
<220> FEATURE:
<223> OTHER INFORMATION: F224Y mutant

<400> SEQUENCE: 6
atgacaacaa agaagcgtcc actacccccgt catctgcacc ttccacctgg agtagaagta      60
ctcgtctctc caccacccta cgaagtatgc acgctcgtcg acagattgtt ggtctacgcc     120
tcgtcgttga ttgtcgttgg atctcccgtt tggttctacg gaggcatcat ttatttttac     180
aggaagtgga agaagtatcg ttctcttgct gctgctactg aggctgcgag acatgagagt     240
ggtggcggtg gtgcatcgtc aacggttcgt tgcagaggta cacgtcaacg tacatcgtct     300
gatgacggca actacacatc gtcaactggc gaaagctcgc aagaaatgaa cgaacaagag     360
acacaaacac aatcacatcg acaacaaaca gagcaataca caactacaa acgattagca     420 acaagatacg gagtagcact cgctgcaatc attctcatat ccatctgggg gcctcatcgt     480
gacaagcgtg taggagaatg gctcggtgtc aagaagtgga gattgtggga tgcatggttg     540
aactatgttg gattcactgt actaaaggac aatggagatg atgaccacac aataatacaa     600
acgaatccac actcagcaat acccaatcaa gaagagtttg acatacacac atctccatca     660
atcttcgcat acgtacccca cggcatcttt cctttcggac tcgccttttc atgtctaccc     720
gaacgaggac acgaacaaac atgggtctc ttccgaccag tcgttgcaac agccaccaaa     780
ctctttccgc tggtacgaac cttcatttct ggatgaacg gagtggatgc ttcgcgttcg     840
gcggtgtctc gtgctcttgc tcctccgtat accagtgatc atccgggaag agtgggagtt     900
tcgcccggtg gtattgccga gatgtttgag acgtatccaa agccggggtt tcatcctaat     960
gacgaggcag cattgttaaa agatcggaat ggattgttca gcttgcgat gaaacacaag    1020 ctgccgattg ttccggtgta ctgctttgga gctacaaaga tgttgagacg agtgcaatta    1080
cctgcgtttg tggagacgtt gagcagaatg ctcaagatca gtctttgttt attctttgga    1140
```

```
aagcttgggt tgcctattcc tttccgacag cggctgatgt atgtcatggg caagacgttg   1200
tttcctcctc tgccgagaga tggcgtgaac acttctatga tggaaggagg agaagaattt   1260
gatgaacgag tgcaagagat gcatgatgca ttctgcaatg agataactcg catcttcgag   1320
cgaaacaaag accactacgg ttggggtaac aaaaacttga gactcgtatg agagtgtgag   1380
tgatattcat atgcaactct taacttaaag ccacagacca cacaggcaca aa            1432
```

<210> SEQ ID NO 7
<211> LENGTH: 456
<212> TYPE: PRT
<213> ORGANISM: Artificial
<220> FEATURE:
<223> OTHER INFORMATION: V298I mutant

<400> SEQUENCE: 7

```
Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
            20                  25                  30

Val Asp Arg Leu Leu Val Tyr Ala Ser Ser Leu Ile Val Val Gly Ser
        35                  40                  45

Pro Val Trp Phe Tyr Gly Gly Ile Ile Tyr Phe Tyr Arg Lys Trp Lys
    50                  55                  60

Leu Tyr Arg Ser Lys Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
            100                 105                 110

Ser Gln Glu Met Asn Glu Gln Thr Gln Thr Gln Ser His Arg Gln
        115                 120                 125

Gln Thr Glu Gln Tyr Asn Asn Tyr Lys Arg Leu Ala Thr Arg Tyr Gly
    130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Lys Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
        195                 200                 205

Asn Gln Glu Glu Phe Asp Ile His Thr Ser Pro Ser Ile Phe Ala Phe
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
                245                 250                 255

Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
        275                 280                 285

Pro Tyr Thr Ser Asp His Pro Gly Arg Ile Gly Val Ser Pro Gly Gly
    290                 295                 300

Ile Ala Glu Met Phe Glu Thr Tyr Pro Lys Pro Gly Phe His Pro Asn
305                 310                 315                 320
```

Asp Glu Ala Ala Leu Leu Lys Asp Arg Asn Gly Leu Phe Lys Leu Ala
            325                 330                 335

Met Lys His Lys Leu Pro Ile Val Pro Val Tyr Cys Phe Gly Ala Thr
        340                 345                 350

Lys Met Leu Arg Arg Val Gln Leu Pro Ala Phe Val Glu Thr Leu Ser
    355                 360                 365

Arg Met Leu Lys Ile Ser Leu Cys Leu Phe Gly Lys Leu Gly Leu
370                 375                 380

Pro Ile Pro Phe Arg Gln Arg Leu Met Tyr Val Met Gly Lys Thr Leu
385                 390                 395                 400

Phe Pro Pro Leu Pro Arg Asp Gly Val Asn Thr Ser Met Met Glu Gly
                405                 410                 415

Gly Glu Glu Phe Asp Gly Arg Val Gln Glu Met His Asp Ala Phe Cys
            420                 425                 430

Asn Glu Ile Thr Arg Ile Phe Glu Arg Asn Lys Asp His Tyr Gly Trp
        435                 440                 445

Gly Asn Lys Asn Leu Arg Leu Val
    450                 455

<210> SEQ ID NO 8
<211> LENGTH: 1432
<212> TYPE: DNA
<213> ORGANISM: Artificial
<220> FEATURE:
<223> OTHER INFORMATION: V298I mutant

<400> SEQUENCE: 8
atgacaacaa agaagcgtcc actacccgt catctgcacc ttccacctgg agtagaagta      60
ctcgtctctc caccccta cgaagtatgc acgctcgtcg acagattgtt ggtctacgcc     120
tcgtcgttga ttgtcgttgg atctcccgtt tggttctacg aggcatcat ttattttttac     180 aggaagtgga gaagtatcg ttctcttgct gctgctactg aggctgcgag acatgagagt     240
ggtggcggtg gtgcatcgtc aacggttcgt tgcagaggta cacgtcaacg tacatcgtct     300
gatgacggca actacacatc gtcaactggc gaaagctcgc aagaaatgaa cgaacaagag     360
acacaaacac aatcacatcg acaacaaaca gagcaataca caactacaa acgattagca     420 acaagatacg gagtagcact cgctgcaatc attctcatat ccatctgggg gcctcatcgt     480
gacaagcgtg taggagaatg gctcggtgtc aagaagtgga gattgtggga tgcatggttg     540
aactatgttg gattcactgt actaaaggac aatggagatg atgaccacac aataatacaa     600
acgaatccac actcagcaat acccaatcaa gaagagtttg acatacacac atctccatca     660
atcttcgcat tcgtaccca cggcatcttt cctttcggac tcgccttttc atgtctaccc     720
gaacgaggac acgaacaaac atggggtctc ttccgaccag tcgttgcaac agccaccaaa     780
ctctttccgc tggtacgaac cttcatttct tggatgaacg agtggatgc ttcgcgttcg     840 gcggtgtctc gtgctcttgc tcctccgtat accagtgatc atccgggaag aatcggagtt     900
tcgcccggtg gtattgccga gatgtttgag acgtatccaa gccggggtt tcatcctaat     960 gacgaggcag cattgttaaa agatcggaat ggattgttca agcttgcgat gaaacacaag    1020
ctgccgattg ttccggtgta ctgctttgga gctacaaaga tgttgagacg agtgcaatta    1080
cctgcgtttg tggagacgtt gagcagaatg ctcaagatca gtctttgttt attctttgga    1140
aagcttgggt tgcctattcc tttccgacag cggctgatgt atgtcatggg caagacgttg    1200
tttcctcctc tgccgagaga tggcgtgaac acttctatga tggaaggagg agaagaattt    1260

-continued

```
gatgaacgag tgcaagagat gcatgatgca ttctgcaatg agataactcg catcttcgag   1320
cgaaacaaag accactacgg ttggggtaac aaaaacttga gactcgtatg agagtgtgag   1380
tgatattcat atgcaactct aacttaaag ccacagacca cacaggcaca aa            1432
```

<210> SEQ ID NO 9
<211> LENGTH: 456
<212> TYPE: PRT
<213> ORGANISM: Artificial
<220> FEATURE:
<223> OTHER INFORMATION: I343L mutant

<400> SEQUENCE: 9

```
Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
            20                  25                  30

Val Asp Arg Leu Leu Val Tyr Ala Ser Ser Leu Ile Val Gly Ser
        35                  40                  45

Pro Val Trp Phe Tyr Gly Gly Ile Ile Tyr Phe Tyr Arg Lys Trp Lys
    50                  55                  60

Leu Tyr Arg Ser Lys Ala Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
            100                 105                 110

Ser Gln Glu Met Asn Glu Gln Glu Thr Gln Thr Gln Ser His Arg Gln
        115                 120                 125

Gln Thr Glu Gln Tyr Asn Asn Tyr Lys Arg Leu Ala Thr Arg Tyr Gly
    130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Lys Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
        195                 200                 205

Asn Gln Glu Glu Phe Asp Ile His Thr Ser Pro Ser Ile Phe Ala Phe
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
                245                 250                 255

Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
        275                 280                 285

Pro Tyr Thr Ser Asp His Pro Gly Arg Val Gly Val Ser Pro Gly Gly
    290                 295                 300

Ile Ala Glu Met Phe Glu Thr Tyr Pro Lys Pro Gly Phe His Pro Asn
305                 310                 315                 320

Asp Glu Ala Ala Leu Leu Lys Asp Arg Asn Gly Leu Phe Lys Leu Ala
                325                 330                 335
```

```
Met Lys His Lys Leu Pro Leu Val Pro Val Tyr Cys Phe Gly Ala Thr
            340                 345                 350

Lys Met Leu Arg Arg Val Gln Leu Pro Ala Phe Val Glu Thr Leu Ser
        355                 360                 365

Arg Met Leu Lys Ile Ser Leu Cys Leu Phe Phe Gly Lys Leu Gly Leu
    370                 375                 380

Pro Ile Pro Phe Arg Gln Arg Leu Met Tyr Val Met Gly Lys Thr Leu
385                 390                 395                 400

Phe Pro Pro Leu Pro Arg Asp Gly Val Asn Thr Ser Met Met Glu Gly
                405                 410                 415

Gly Glu Glu Phe Asp Gly Arg Val Gln Glu Met His Asp Ala Phe Cys
            420                 425                 430

Asn Glu Ile Thr Arg Ile Phe Glu Arg Asn Lys Asp His Tyr Gly Trp
        435                 440                 445

Gly Asn Lys Asn Leu Arg Leu Val
    450                 455

<210> SEQ ID NO 10
<211> LENGTH: 1432
<212> TYPE: DNA
<213> ORGANISM: Artificial
<220> FEATURE:
<223> OTHER INFORMATION: I343L mutant

<400> SEQUENCE: 10
atgacaacaa agaagcgtcc actacccegt catctgcacc ttccacctgg agtagaagta      60
ctcgtctctc caccacccta cgaagtatgc acgctcgtcg acagattgtt ggtctacgcc     120
tcgtcgttga ttgtcgttgg atctcccgtt tggttctacg gaggcatcat ttatttttac     180
aggaagtgga agaagtatcg ttctcttgct gctgctactg aggctgcgag acatgagagt     240
ggtggcggtg gtgcatcgtc aacggttcgt tgcagaggta cacgtcaacg tacatcgtct     300
gatgacggca actacacatc gtcaactggc gaaagctcgc aagaaatgaa cgaacaagag     360
acacaaacac aatcacatcg acaacaaaca gagcaataca caactacaa acgattagca      420 acaagatacg gagtagcact cgctgcaatc attctcatat ccatctgggg gcctcatcgt     480
gacaagcgtg taggagaatg gctcggtgtc aagaagtgga gattgtggga tgcatggttg     540
aactatgttg gattcactgt actaaaggac aatggagatg atgaccacac aataatacaa     600
acgaatccac actcagcaat acccaatcaa gaagagtttg acatacacac atctccatca     660
atcttcgcat tcgtaccca cggcatcttt cctttcggac tcgccttttc atgtctaccc      720
gaacgaggac acgaacaaac atggggtctc ttccgaccag tcgttgcaac agccaccaaa     780
ctctttccgc tggtacgaac cttcatttct tggatgaacg gagtggatgc ttcgcgttcg     840
gcggtgtctc gtgctcttgc tcctccgtat accagtgatc atccgggaag agtgggagtt     900
tcgcccggtg gtattgccga gatgtttgag acgtatccaa agccgggtt tcatcctaat      960 gacgaggcag cattgttaaa agatcggaat ggattgttca agcttgcgat gaaacacaag    1020
ctgccgcttg ttccggtgta ctgctttgga gctacaaaga tgttgagacg agtgcaatta    1080
cctgcgtttg tggagacgtt gagcagaatg ctcaagatca gtctttgttt attctttgga    1140
aagcttgggt tgcctattcc tttccgacag cggctgatgt atgtcatggg caagacgttg    1200
tttcctcctc tgccgagaga tggcgtgaac acttctatga tggaaggagg agaagaatt     1260 gatgaacgag tgcaagagat gcatgatgca ttctgcaatg agataactcg catcttcgag    1320
```
cgaaacaaag accactacgg ttggggtaac aaaaacttga gactcgtatg agagtgtgag    1380
tgatattcat atgcaactct aacttaaag ccacagacca cacaggcaca aa             1432

<210> SEQ ID NO 11
<211> LENGTH: 456
<212> TYPE: PRT
<213> ORGANISM: Artificial
<220> FEATURE:
<223> OTHER INFORMATION: E365K mutant

<400> SEQUENCE: 11

Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
            20                  25                  30

Val Asp Arg Leu Leu Val Tyr Ala Ser Ser Leu Ile Val Val Gly Ser
        35                  40                  45

Pro Val Trp Phe Tyr Gly Gly Ile Ile Tyr Phe Tyr Arg Lys Trp Lys
    50                  55                  60

Leu Tyr Arg Ser Lys Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
            100                 105                 110

Ser Gln Glu Met Asn Glu Gln Glu Thr Gln Thr Gln Ser His Arg Gln
        115                 120                 125

Gln Thr Glu Gln Tyr Asn Asn Tyr Lys Arg Leu Ala Thr Arg Tyr Gly
    130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Lys Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
        195                 200                 205

Asn Gln Glu Glu Phe Asp Ile His Thr Ser Pro Ser Ile Phe Ala Phe
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
                245                 250                 255

Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
        275                 280                 285

Pro Tyr Thr Ser Asp His Pro Gly Arg Val Gly Val Ser Pro Gly Gly
    290                 295                 300

Ile Ala Glu Met Phe Glu Thr Tyr Pro Lys Pro Gly Phe His Pro Asn
305                 310                 315                 320

Asp Glu Ala Ala Leu Leu Lys Asp Arg Asn Gly Leu Phe Lys Leu Ala
                325                 330                 335

Met Lys His Lys Leu Pro Ile Val Pro Val Tyr Cys Phe Gly Ala Thr
            340                 345                 350

```
Lys Met Leu Arg Arg Val Gln Leu Pro Ala Phe Val Lys Thr Leu Ser
            355                 360                 365

Arg Met Leu Lys Ile Ser Leu Cys Leu Phe Phe Gly Lys Leu Gly Leu
        370                 375                 380

Pro Ile Pro Phe Arg Gln Arg Leu Met Tyr Val Met Gly Lys Thr Leu
385                 390                 395                 400

Phe Pro Pro Leu Pro Arg Asp Gly Val Asn Thr Ser Met Met Glu Gly
                405                 410                 415

Gly Glu Glu Phe Asp Gly Arg Val Gln Glu Met His Asp Ala Phe Cys
            420                 425                 430

Asn Glu Ile Thr Arg Ile Phe Glu Arg Asn Lys Asp His Tyr Gly Trp
        435                 440                 445

Gly Asn Lys Asn Leu Arg Leu Val
    450                 455

<210> SEQ ID NO 12
<211> LENGTH: 1432
<212> TYPE: DNA
<213> ORGANISM: Artificial
<220> FEATURE:
<223> OTHER INFORMATION: E365K mutant

<400> SEQUENCE: 12
atgacaacaa agaagcgtcc actacccgt catctgcacc ttccacctgg agtagaagta      60
ctcgtctctc caccacccta cgaagtatgc acgctcgtcg acagattgtt ggtctacgcc    120
tcgtcgttga ttgtcgttgg atctcccgtt tggttctacg gaggcatcat ttatttttac    180
aggaagtgga agaagtatcg ttctcttgct gctgctactg aggctgcgag acatgagagt    240
ggtggcggtg gtgcatcgtc aacggttcgt tgcagaggta cacgtcaacg tacatccgtct   300 gatgacggca actacacatc gtcaactggc gaaagctcgc aagaaatgaa cgaacaagag    360
acacaaacac aatcacatcg acaacaaaca gagcaataca caactacaa acgattagca     420 acaagatacg gagtagcact cgctgcaatc attctcatat ccatctgggg gcctcatcgt    480
gacaagcgtg taggagaatg gctcggtgtc aagaagtgga gattgtggga tgcatggttg    540
aactatgttg gattcactgt actaaaggac aatggagatg atgaccacac aataatacaa    600
acgaatccac actcagcaat acccaatcaa gaagagtttg acatacacac atctccatca    660
atcttcgcat tcgtacccca cggcatcttt cctttcggac tcgccttttc atgtctaccc    720
gaacgaggac acgaacaaac atggggtctc ttccgaccag tcgttgcaac agccaccaaa    780
ctctttccgc tggtacgaac cttcattttct tggatgaacg agtggatgc ttcgcgttcg    840 gcggtgtctc gtgctcttgc tcctccgtat accagtgatc atccgggaag agtgggagtt    900
tcgcccggtg gtattgccga atgtttgag acgtatccaa agccgggggtt tcatcctaat    960 gacgaggcag cattgttaaa agatcggaat ggattgttca agcttgcgat gaaacacaag   1020
ctgccgattg ttccggtgta ctctttgga gctacaaaga tgttgagacg agtgcaatta   1080
cctgcgtttg tgaagacgtt gagcagaatg ctcaagatca gtctttgttt attctttgga  1140
aagcttgggt tgcctattcc tttccgacag cggctgatgt atgtcatggg caagacgttg  1200
tttcctcctc tgccgagaga tggcgtgaac acttctatga tggaaggagg agaagaattt  1260
gatgaacgag tgcaagagat gcatgatgca ttctgcaatg ataactcg catcttcgag   1320 cgaaacaaag accactacgg ttggggtaac aaaaacttga gactcgtatg agagtgtgag  1380
tgatattcat atgcaactct taacttaaag ccacagacca cacaggcaca aa          1432
```

<210> SEQ ID NO 13
<211> LENGTH: 456
<212> TYPE: PRT
<213> ORGANISM: Artificial
<220> FEATURE:
<223> OTHER INFORMATION: L400I mutant

<400> SEQUENCE: 13

```
Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
            20                  25                  30

Val Asp Arg Leu Leu Val Tyr Ala Ser Ser Leu Ile Val Val Gly Ser
            35                  40                  45

Pro Val Trp Phe Tyr Gly Gly Ile Ile Tyr Phe Tyr Arg Lys Trp Lys
    50                  55                  60

Leu Tyr Arg Ser Lys Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
            100                 105                 110

Ser Gln Glu Met Asn Glu Gln Glu Thr Gln Thr Gln Ser His Arg Gln
        115                 120                 125

Gln Thr Glu Gln Tyr Asn Asn Tyr Lys Arg Leu Ala Thr Arg Tyr Gly
    130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Lys Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
        195                 200                 205

Asn Gln Glu Glu Phe Asp Ile His Thr Ser Pro Ser Ile Phe Ala Phe
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
                245                 250                 255

Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
        275                 280                 285

Pro Tyr Thr Ser Asp His Pro Gly Arg Val Gly Val Ser Pro Gly Gly
    290                 295                 300

Ile Ala Glu Met Phe Glu Thr Tyr Pro Lys Pro Gly Phe His Pro Asn
305                 310                 315                 320

Asp Glu Ala Ala Leu Leu Lys Asp Arg Asn Gly Leu Phe Lys Leu Ala
                325                 330                 335

Met Lys His Lys Leu Pro Ile Val Pro Val Tyr Cys Phe Gly Ala Thr
            340                 345                 350

Lys Met Leu Arg Arg Val Gln Leu Pro Ala Phe Val Glu Thr Leu Ser
        355                 360                 365
```

Arg Met Leu Lys Ile Ser Leu Cys Leu Phe Phe Gly Lys Leu Gly Leu
        370                 375                 380

Pro Ile Pro Phe Arg Gln Arg Leu Met Tyr Val Met Gly Lys Thr Ile
385                 390                 395                 400

Phe Pro Pro Leu Pro Arg Asp Gly Val Asn Thr Ser Met Met Glu Gly
                405                 410                 415

Gly Glu Glu Phe Asp Gly Arg Val Gln Glu Met His Asp Ala Phe Cys
            420                 425                 430

Asn Glu Ile Thr Arg Ile Phe Glu Arg Asn Lys Asp His Tyr Gly Trp
        435                 440                 445

Gly Asn Lys Asn Leu Arg Leu Val
        450                 455

<210> SEQ ID NO 14
<211> LENGTH: 1432
<212> TYPE: DNA
<213> ORGANISM: Artificial
<220> FEATURE:
<223> OTHER INFORMATION: L400I mutant

<400> SEQUENCE: 14
atgacaacaa agaagcgtcc actacccgt catctgcacc ttccacctgg agtagaagta       60
ctcgtctctc caccacccta cgaagtatgc acgctcgtcg acagattgtt ggtctacgcc     120
tcgtcgttga ttgtcgttgg atctcccgtt tggttctacg gaggcatcat ttattttac      180
aggaagtgga agaagtatcg ttctcttgct gctgctactg aggctgcgag acatgagagt     240
ggtggcggtg gtgcatcgtc aacggttcgt tgcagaggta cacgtcaacg tacatcgtct     300
gatgacggca actacacatc gtcaactggc gaaagctcgc aagaaatgaa cgaacaagag     360
acacaaacac aatcacatcg acaacaaaca gagcaataca caactacaa acgattagca     420
acaagatacg gagtagcact cgctgcaatc attctcatat ccatctgggg gcctcatcgt     480
gacaagcgtg taggagaatg gctcggtgtc aagaagtgga gattgtggga tgcatggttg     540
aactatgttg gattcactgt actaaaggac aatggagatg atgaccacac aataatacaa     600
acgaatccac actcagcaat acccaatcaa gaagagtttg acatacacac atctccatca     660
atcttcgcat tcgtaccca cggcatcttt cctttcggac tcgcctttc atgtctaccc       720
gaacgaggac acgaacaaac atggggtctc ttccgaccag tcgttgcaac agccaccaaa     780
ctctttccgc tggtacgaac cttcatttct tggatgaacg gagtggatgc ttcgcgttcg     840
gcggtgtctc gtgctcttgc tcctccgtat accagtgatc atccgggaag agtgggagtt     900
tcgcccggtg gtattgccga gatgtttgag acgtatccaa agccggggtt tcatcctaat     960
gacgaggcag cattgttaaa agatcggaat ggattgttca agcttgcgat gaaacacaag    1020
ctgccgattg ttccggtgta ctgctttgga gctacaagaa tgttgagacg agtgcaatta    1080
cctgcgtttg tggagacgtt gagcagaatg ctcaagatca gtctttgttt attctttgga    1140
aagcttgggt tgcctattcc tttccgacag cggctgatgt atgtcatggg caagacgatc    1200
tttcctcctc tgccgagaga tggcgtgaac acttctatga tggaaggagg agaagaattt    1260
gatgaacgag tgcaagagat gcatgatgca ttctgcaatg agataactcg catcttcgag    1320
cgaaacaaag accactacgg ttggggtaac aaaaacttga gactcgtatg agagtgtgag    1380
tgatattcat atgcaactct taacttaaag ccacagacca cacaggcaca aa             1432

<210> SEQ ID NO 15

<211> LENGTH: 124
<212> TYPE: PRT
<213> ORGANISM: Artificial
<220> FEATURE:
<223> OTHER INFORMATION: Catalytic domain

<400> SEQUENCE: 15

```
Ile Phe Pro Phe Gly Leu Ala Phe Ser Cys Leu Pro Glu Arg Gly His
1               5                   10                  15
Glu Gln Thr Trp Gly Leu Phe Arg Pro Val Val Ala Thr Ala Thr Lys
            20                  25                  30
Leu Phe Pro Leu Val Arg Thr Phe Ile Ser Trp Met Asn Gly Val Asp
        35                  40                  45
Ala Ser Asp Ser Ala Val Ser Arg Ala Leu Ala Pro Pro Tyr Thr Ser
    50                  55                  60
Asp His Pro Gly Arg Val Gly Val Ser Pro Gly Gly Ile Ala Glu Met
65                  70                  75                  80
Phe Glu Thr Tyr Pro Lys Pro Gly Phe His Pro Asn Asp Glu Ala Ala
                85                  90                  95
Leu Leu Lys Asp Arg Asn Gly Leu Phe Lys Leu Ala Met Lys His Lys
            100                 105                 110
Leu Pro Ile Val Pro Val Tyr Cys Phe Gly Ala Thr
        115                 120
```

<210> SEQ ID NO 16
<211> LENGTH: 372
<212> TYPE: DNA
<213> ORGANISM: Artificial
<220> FEATURE:
<223> OTHER INFORMATION: Catalytic domain

<400> SEQUENCE: 16

```
atctttcctt tcggactcgc cttttcatgt ctacccgaac gaggacacga acaaacatgg    60
ggtctcttcc gaccagtcgt tgcaacagcc accaaactct ttccgctggt acgaaccttc   120
atttcttgga tgaacggagt ggatgcttcg cgttcggcgg tgtctcgtgc tcttgctcct   180
ccgtatacca gtgatcatcc gggaagagtg ggagtttcgc ccggtggtat tgccgagatg   240
tttgagacgt atccaaagcc ggggtttcat cctaatgacg aggcagcatt gttaaaagat   300
cggaatggat tgttcaagct tgcgatgaaa cacaagctgc cgattgttcc ggtgtactgc   360
tttggagcta ca                                                       372
```

<210> SEQ ID NO 17
<211> LENGTH: 124
<212> TYPE: PRT
<213> ORGANISM: Artificial
<220> FEATURE:
<223> OTHER INFORMATION: V298I mutant catalytic domain

<400> SEQUENCE: 17

```
Ile Phe Pro Phe Gly Leu Ala Phe Ser Cys Leu Pro Glu Arg Gly His
1               5                   10                  15
Glu Gln Thr Trp Gly Leu Phe Arg Pro Val Val Ala Thr Ala Thr Lys
            20                  25                  30
Leu Phe Pro Leu Val Arg Thr Phe Ile Ser Trp Met Asn Gly Val Asp
        35                  40                  45
Ala Ser Asp Ser Ala Val Ser Arg Ala Leu Ala Pro Pro Tyr Thr Ser
    50                  55                  60
Asp His Pro Gly Arg Ile Gly Val Ser Pro Gly Gly Ile Ala Glu Met
```

```
                65                  70                  75                  80
Phe Glu Thr Tyr Pro Lys Pro Gly Phe His Pro Asn Asp Glu Ala Ala
                        85                  90                  95

Leu Leu Lys Asp Arg Asn Gly Leu Phe Lys Leu Ala Met Lys His Lys
                100                 105                 110

Leu Pro Ile Val Pro Val Tyr Cys Phe Gly Ala Thr
            115                 120
```

<210> SEQ ID NO 18
<211> LENGTH: 372
<212> TYPE: DNA
<213> ORGANISM: Artificial
<220> FEATURE:
<223> OTHER INFORMATION: V298I mutant catalytic domain

<400> SEQUENCE: 18

```
atctttcctt tcggactcgc cttttcatgt ctacccgaac gaggacacga acaaacatgg      60
ggtctcttcc gaccagtcgt tgcaacagcc accaaactct ttccgctggt acgaaccttc     120
atttcttgga tgaacggagt ggatgcttcg cgttcggcgg tgtctcgtgc tcttgctcct     180
ccgtatacca gtgatcatcc gggaagaatc ggagtttcgc ccggtggtat tgccgagatg     240
tttgagacgt atccaaagcc ggggtttcat cctaatgacg aggcagcatt gttaaaagat     300
cggaatggat tgttcaagct tgcgatgaaa cacaagctgc cgattgttcc ggtgtactgc     360
tttggagcta ca                                                         372
```

<210> SEQ ID NO 19
<211> LENGTH: 124
<212> TYPE: PRT
<213> ORGANISM: Artificial
<220> FEATURE:
<223> OTHER INFORMATION: I343L mutant catalytic domain

<400> SEQUENCE: 19

```
Ile Phe Pro Phe Gly Leu Ala Phe Ser Cys Leu Pro Glu Arg Gly His
1               5                   10                  15

Glu Gln Thr Trp Gly Leu Phe Arg Pro Val Val Ala Thr Ala Thr Lys
            20                  25                  30

Leu Phe Pro Leu Val Arg Thr Phe Ile Ser Trp Met Asn Gly Val Asp
        35                  40                  45

Ala Ser Asp Ser Ala Val Ser Arg Ala Leu Ala Pro Pro Tyr Thr Ser
    50                  55                  60

Asp His Pro Gly Arg Val Gly Val Ser Pro Gly Ile Ala Glu Met
65                  70                  75                  80

Phe Glu Thr Tyr Pro Lys Pro Gly Phe His Pro Asn Asp Glu Ala Ala
                85                  90                  95

Leu Leu Lys Asp Arg Asn Gly Leu Phe Lys Leu Ala Met Lys His Lys
                100                 105                 110

Leu Pro Leu Val Pro Val Tyr Cys Phe Gly Ala Thr
            115                 120
```

<210> SEQ ID NO 20
<211> LENGTH: 372
<212> TYPE: DNA
<213> ORGANISM: Artificial
<220> FEATURE:
<223> OTHER INFORMATION: I343L mutant catalytic domain

<400> SEQUENCE: 20

```
atctttcctt tcggactcgc cttttcatgt ctacccgaac gaggacacga acaaacatgg    60
ggtctcttcc gaccagtcgt tgcaacagcc accaaactct ttccgctggt acgaaccttc   120
atttcttgga tgaacggagt ggatgcttcg cgttcggcgg tgtctcgtgc tcttgctcct   180 ccgtataccagtgatcatcc gggaagagtg ggagtttcgc ccggtggtat tgccgagatg   240
tttgagacgt atccaaagcc ggggtttcat cctaatgacg aggcagcatt gttaaaagat   300
cggaatggat tgttcaagct tgcgatgaaa cacaagctgc cgcttgttcc ggtgtactgc   360
tttggagcta ca                                                       372
```

\<210\> SEQ ID NO 21
\<211\> LENGTH: 1432
\<212\> TYPE: DNA
\<213\> ORGANISM: Artificial
\<220\> FEATURE:
\<223\> OTHER INFORMATION: 80% nucleotide sequence homology to TpDGA2

\<400\> SEQUENCE: 21

```
atgactacta aaaacgacc tcttccgcga catctccacc tacctccagg tgttgaagtt     60
ctggtgtcac ctcctccgta cgaagtttgc accctggtgg acagattgtt ggtgtacgcg   120
tcctccttga tagtggtagg ttcaccggta tggttctacg gtgggatcat atatttttac   180
aggaaatgga aaaatatcg atcactagca gcagcaacag aggcagccag acatgagagt    240 ggaggggag gagcttcctc taccgtacga tgcagaggaa ctcgacagcg aacttcctca    300
gatgacggga actacacttc ctctacaggg gaaagctccc aggaaatgaa cgaacaggag   360
actcagactc agtctcatcg tcagcagact gagcagtaca caactacaa gcgtttagct    420 actagatacg gtgttgctct ggcagctatc atactgattt cgatctgggg cccacatcga   480
gacaaacgag ttggtgaatg gctgggagtg aaaaaatgga gattgtggga tgcttggttg   540
aactatgtag gtttcacagt tcttaaagac aatggtgatg atgaccacac tattattcag   600
accaatcctc actctgctat tccgaatcag aagagtttg acattcacac ttcaccttct    660
atcttcgctt tcgttccgca cgggatcttt ccattcggtc tggcgttttc ttgtcttccg   720
gaacgtggtc acgaacagac ttggggactg ttccgtcctg tggtagctac tgcgacgaag   780
ctgtttcccc tcgttcgtac gttcatatca tggatgaacg gtgtcgatgc atcccgatcc   840
gccgtctcac gagcactagc accaccctat acgagtgatc atcccggtag agtcggtgta   900
tccccgggag gaatagcgga gatgtttgag acctatccta aacccggctt tcatccaaat   960
gacgaggctc tttgttaaa ggatcgcaat ggtttgttca actagccat gaagcacaaa    1020 ctccccatag taccgtcta ctgctttggt gcaactaaaa tgttgagacg tgtccagtta   1080
ccagcctttg tcgagacctt gagcagaatg ctgaaaatca gtctatgttt attctttggt   1140
aaactaggct tgccaatacc attccgtcaa cgcctcatgt atgtgatggg gaaaaccttg   1200
tttccaccac tccccagaga tggggtcaac acatcaatga tggaaggtgg tgaagaattt   1260
gatgaacgtg tccaggagat gcatgatgct ttctgcaatg agattacacg gatcttcgag   1320
cgtaacaagg accactacgg atggggaaac aagaacttga gactggtttg agagtgtgag   1380
tgatattctt atgctacact aaacttaaaa cctcaaacga ctcaagctca ga           1432
```

\<210\> SEQ ID NO 22
\<211\> LENGTH: 1432
\<212\> TYPE: DNA
\<213\> ORGANISM: Artificial
\<220\> FEATURE:
\<223\> OTHER INFORMATION: 85% nucleotide sequence homology to TpDGA2

```
<400> SEQUENCE: 22
atgacaacta aaaaacgacc tcttccgcgt catctccacc tacctcctgg tgttgaagtt    60
ctcgtgtcac ctccaccgta cgaagtttgc accctcgtgg acagattgtt ggtgtacgcg   120
tcgtccttga tagtggttgg ttcaccggtt tggttctacg gtgggatcat atattttac    180 aggaaatgga aaaaatatcg atctctagca gcagctacag aggcagccag acatgagagt   240 ggtggggag gagcatcctc taccgttcga tgcagaggaa ctcgtcagcg aacttcgtca    300
gatgacggga actacacttc gtctacaggg gaaagctcgc aggaaatgaa cgaacaggag   360
acacagactc agtctcatcg acagcagaca gagcagtaca caactacaa gcgtttagct    420 acaagatacg tgttgctct cgcagctatc atactcattt cgatctgggg ccctcatcga    480
gacaaacgag taggtgaatg gctgggagtc aaaaaatgga gattgtggga tgcttggttg   540
aactatgttg gtttcacagt tctaaaagac aatggtgatg atgaccacac tataattcag   600
accaatccac actctgctat tcccaatcag gaagagtttg acattcacac ttctccttct   660
atcttcgctt tcgtaccgca cgggatcttt ccattcggac tggcgttttc ttgtctaccg   720
gaacgtggac acgaacagac ttggggactg ttccgacctg tggtagcaac tgcgaccaag   780
ctgtttcccc tcgtacgtac gttcatatct tggatgaacg gtgtcgatgc atcgcgatcc   840
gccgtgtcac gagcacttgc caccctat ccagtgatc atcccggtag agtcggagta    900
tccccgggtg aatagcgga gatgtttgag acgtatccta aacccgggtt tcatccaaat   960
gacgaggctg ctttgttaaa cgatcgcaat ggtttgttca aacttgccat gaagcacaaa  1020
ctgcccatag taccggtcta ctgctttggt gcaacaaaaa tgttgagacg tgtgcagtta  1080
ccagcctttg tcgagacgtt gagcagaatg ctgaaaatca gtctatgttt attctttgga  1140
aaactaggct tgcctatacc attccgacaa cgcctcatgt atgtgatggg caaaaccttg  1200
tttccaccgc tccccagaga tggggtgaac acatcaatga tggaaggtgg agaagaattt  1260
gatgaacgtg tccaggagat gcatgatgca ttctgcaatg agattacacg gatcttcgag  1320
cgaaacaagg accactacgg atggggtaac aagaacttga gactggtttg agagtgtgag  1380
tgatattctt atgcaacact aaacttaaaa ccacaaacga cacaagctca ga           1432

<210> SEQ ID NO 23
<211> LENGTH: 1432
<212> TYPE: DNA
<213> ORGANISM: Artificial
<220> FEATURE:
<223> OTHER INFORMATION: 90% nucleotide sequence homology to TpDGA2

<400> SEQUENCE: 23
atgacaacta aaaaacgtcc tcttccgcgt catctgcacc tacctcctgg agtagaagtt    60
ctcgtgtcac caccaccgta cgaagtttgc accctcgtcg acagattgtt ggtgtacgcg   120
tcgtcgttga ttgtggttgg ttcacccgtt tggttctacg gtggcatcat atattttac    180 aggaaatgga aaaaatatcg atctcttgct gcagctacag aggcagcgag acatgagagt   240 ggtggggag gagcatcgtc taccgttcgt tgcagaggta ctcgtcagcg aacatcgtca    300
gatgacggga actacacttc gtcaactggc gaaagctcgc aggaaatgaa cgaacaggag   360
acacagactc agtcacatcg acagcagaca gagcagtaca caactacaa gcgattagct    420 acaagatacg tgtagcact cgcagctatc attctcattt cgatctgggg ccctcatcgt    480
gacaaacgag taggtgaatg gctcggtgtc aaaaaatgga gattgtggga tgcatggttg   540
```

```
aactatgttg gtttcacagt tctaaaagac aatggagatg atgaccacac tataattcag    600
acgaatccac actcagctat acccaatcag aagagtttg acattcacac ttctccatct    660
atcttcgctt tcgtaccgca cggcatcttt ccattcggac tcgcgttttc atgtctaccg    720
gaacgtggac acgaacagac atggggactg ttccgacctg tcgtagcaac agcgaccaag    780
ctctttcccc tcgtacgaac gttcatatct tggatgaacg gtgtggatgc atcgcgttcc    840
gcggtgtcac gagcacttgc tccaccctat accagtgatc atcccggaag agtcggagtt    900
tcccccggtg aatagcgga gatgtttgag acgtatccaa aacccgggtt tcatccaaat    960
gacgaggcag ctttgttaaa cgatcggaat ggtttgttca aacttgcgat gaagcacaaa   1020
ctgccgatag taccggtcta ctgctttgga gctacaaaaa tgttgagacg tgtgcagtta   1080
cctgcctttg tcgagacgtt gagcagaatg ctcaaaatca gtctatgttt attctttgga   1140
aaacttggct tgcctattcc attccgacaa cggctcatgt atgtgatggg caaaacgttg   1200
tttccaccgc tcccgagaga tggggtgaac acttcaatga tggaaggagg agaagaattt   1260
gatgaacgtg tccaggagat gcatgatgca ttctgcaatg agataacacg gatcttcgag   1320
cgaaacaagg accactacgg ttggggtaac aagaacttga gactcgtttg agagtgtgag   1380
tgatattcat atgcaacact taacttaaaa ccacaaacca cacaagcaca ga           1432
```

<210> SEQ ID NO 24
<211> LENGTH: 1432
<212> TYPE: DNA
<213> ORGANISM: Artificial
<220> FEATURE:
<223> OTHER INFORMATION: 95% nucleotide sequence homology to TpDGA2

<400> SEQUENCE: 24

```
atgacaacaa aaaacgtcc actaccgcgt catctgcacc ttccacctgg tgtagaagta     60
ctcgtgtctc caccaccta cgaagtttgc acgctcgtcg acagattgtt ggtctacgcc    120
tcgtccttga ttgtcgttgg atctcccgtt tggttctacg aggcatcat atattttac    180
aggaaatgga aaaatatcg ttctcttgca gcagcaacag aggcagcgag acatgagagt    240
ggtgggggtg gtgcttcgtc tacggttcgt tgcagaggta cacgtcagcg aacatcgtct    300
gatgacggca actacacatc gtcaactggc gaaagctcgc aggaaatgaa cgaacaggag    360
acacagacac agtcacatcg acagcagaca gagcagtaca caactacaa gcgattagca    420
acaagatacg gagtagcact cgcagcaatc attctcatat ccatctgggg ccctcatcgt    480
gacaaacgtg taggagaatg gctcggtgtc aaaaaatgga gattgtggga tgcatggttg    540
aactatgttg gattcactgt actaaaagac aatggagatg atgaccacac aataatacag    600
acgaatccac actcagctat acccaatcag aagagtttg acatacacac atctccatca    660
atcttcgcat tcgtaccgca cggcatcttt cctttcggac tggcctttc atgtctaccg    720
gaacgtggac acgaacagac atgggtctc ttccgaccag tcgtagcaac agccaccaag    780
ctctttccgc tggtacgaac gttcattct tggatgaacg gtgtggatgc atcgcgttcc    840
gcggtgtctc gtgcacttgc acctccctat accagtgatc atcgggaag agtgggagta    900
tcgcccggtg gtatagccga gatgtttgag acgtatccaa aacggggtt tcatcctaat    960
gacgaggcag ctttgttaaa cgatcggaat ggattgttca aacttgcgat gaaccacaaa   1020
ctgccgattg ttccggtcta ctgctttgga gcaacaaaaa tgttgagacg agtgcagtta   1080
cctgcgtttg tggagacgtt gagcagaatg ctcaaaatca gtctttgttt attctttgga   1140
aaacttgggt tgcctattcc tttccgacaa cggctgatgt atgtcatggg caaaacgttg   1200
```

```
tttcctccgc tgccgagaga tggggtgaac acttcaatga tggaaggagg agaagaattt    1260
gatgaacgag tgcaggagat gcatgatgca ttctgcaatg agataactcg catcttcgag    1320
cgaaacaagg accactacgg ttggggtaac aagaacttga gactcgtatg agagtgtgag    1380
tgatattcat atgcaactct taacttaaaa ccacaaacca cacaagcaca ga            1432
```

<210> SEQ ID NO 25
<211> LENGTH: 309
<212> TYPE: PRT
<213> ORGANISM: T. pseudonana

<400> SEQUENCE: 25

```
Leu Ala Val Thr Leu Trp Leu Gly Trp Asn Gly Ile Val Val Cys Ile
1               5                   10                  15

Ala Val Tyr Leu Leu Phe Ile Ala Asn Asn Ile Glu Arg Met Val Ile
            20                  25                  30

Ile Gly Leu Ala Thr Met Ser Leu Ile Leu Pro Ala His Phe Pro Gly
        35                  40                  45

Ala Leu Gly Tyr Lys Ile Gly Asp Trp Ile Met Arg Gln Ala Glu Lys
    50                  55                  60

Tyr Phe Gly Leu Lys Thr Val Ile Glu Asp Glu Asp Leu Ile Arg
65                  70                  75                  80

His Ala Asn Glu Asn Lys Ala Val Ile Phe Ala Phe Asn Pro His Asp
                85                  90                  95

Met Leu Pro Tyr Ala Val Phe Ala Phe Ala Pro Thr Leu Lys Arg Leu
            100                 105                 110

Pro Gly Lys Ile Gly Lys Asp Gly Thr Cys Leu Met Ser Ser Ala Ile
        115                 120                 125

Phe Asn Ile Pro Phe Leu Arg Gln Val Tyr Thr Trp Val Asn Ser Leu
    130                 135                 140

Pro Val Asp Lys Lys Thr Phe Leu Gly Arg Leu Lys Arg Gly Gln Ser
145                 150                 155                 160

Phe Ala Phe Val Pro Gly Gly Val Gln Glu Val Ile Met Leu Asp Pro
                165                 170                 175

Asn Gln Pro Lys Asp Val Val Leu Tyr Leu Lys Asn Arg Lys Gly Phe
            180                 185                 190

Val Lys Leu Ala Leu Ala Thr Gly Ser Pro Ile Val Pro Val Phe Gly
        195                 200                 205

Phe His Leu Asp Gly Ser Tyr Gly Tyr Trp Leu Pro Lys Gly Lys Leu
    210                 215                 220

Val Glu Arg Leu Ser Arg Thr Leu Gly Phe Leu Pro Leu Leu Phe Trp
225                 230                 235                 240

Gly Arg Trp Met Ile Pro Phe Gly Ile Pro His Pro Lys Lys Ile His
                245                 250                 255

Val Val Val Gly Ser Ala Ile Asp Val Pro Asn Glu Gly Glu Asp Val
            260                 265                 270

Ser Gln Glu Ser Ile Glu Lys Tyr His Ala Ile Phe Leu Lys Glu Leu
        275                 280                 285

Glu Ala Leu Phe Glu Arg His Lys Glu Glu Ala Gly Tyr Gly His Arg
    290                 295                 300

Gln Leu Lys Ile Val
305
```

<210> SEQ ID NO 26

<211> LENGTH: 930
<212> TYPE: DNA
<213> ORGANISM: T. pseudonana

<400> SEQUENCE: 26

```
ctggcagtca cattgtggtt ggggtggaat gggatcgtgg tgtgtatcgc agtctacctc      60
ttgttcattg ccaacaatat tgaacgaatg gtgattattg gattggcaac gatgtcgttg     120
atactgcctg ctcactttcc aggagctttg ggctacaaga ttggggattg gattatgcgt     180
caggcagaga agtactttgg attaaagacg gtgattgaag acgaagagga tttgattcgg     240
catgccaatg agaacaaagc agtgatattt gccttcaatc cacatgatat gttgccgtat     300
gcagtatttg cattcgctcc tacattgaag agactaccgg gtaagatcgg aaggatgga     360
acgtgcctca tgtcatcggc aatcttcaac attccttttt tgagacaagt gtatacgtgg     420
gtgaacagcc ttccagtaga caagaaaaca tttctgggga ggctgaagag agggcaaagc     480
tttgcttttg ttcctggggg agtgcaagag gtcattatgc ttgatccgaa ccagccaaaa     540
gatgtggtgc tatatctcaa gaaccgcaaa ggattcgtga agctggcgtt ggcgacaggc     600
tcgcccatcg tgcccgtgtt tggctttcat ctggatggaa gctatggcta ttggctgccg     660
aaagggaaac tggtcgagag actttcacga acattgggct ttcttcctct tctcttttgg     720
gggcgttgga tgatacccttt cggcatacca cccccaaaa agattcacgt tgtcgttgga     780
tcagcaatag atgtaccgaa cgagggagaa gatgtctcac aagagtcaat tgaaaagtac     840
catgccatct ttctgaagga gcttgaagca ttgtttgaga ggcacaagga agaagcggga     900
tacggacatc ggcaattgaa gattgtctaa                                      930
```

<210> SEQ ID NO 27
<211> LENGTH: 158
<212> TYPE: PRT
<213> ORGANISM: T. pseudonana

<400> SEQUENCE: 27

```
Met Glu Asp Tyr Leu Lys Asn Gly Glu Asp Val Ala Leu Pro Pro Gly
1               5                   10                  15

Gly Phe Glu Glu Ala Thr Leu Thr Cys Thr Thr Gln Asp Arg Val Phe
            20                  25                  30

Ile Lys Lys Arg Tyr Gly Phe Val Arg Leu Cys Leu Lys Tyr Gly Val
        35                  40                  45

Ala Ile Arg Pro Val Tyr Val Phe Gly Glu Gly Arg Leu Phe Gly Asn
    50                  55                  60

Val Gln Gly Met Trp Lys Thr Arg Leu Ala Leu Asn Arg Trp Gly Ile
65                  70                  75                  80

Pro Thr Ile Leu Val Trp Gly Ser Trp Phe Phe Pro Leu Leu Pro Lys
                85                  90                  95

Lys Gly Val Asn Leu His Ile Val Val Gly Lys Pro Leu Ile Val Pro
            100                 105                 110

Lys Ile Asp Asn Pro Thr Lys Glu Glu Val Ile Ala Trp His Glu Lys
        115                 120                 125

Tyr Ile Thr Glu Leu Lys Arg Ile Tyr Glu Glu Tyr Lys Glu Val Ala
    130                 135                 140

Tyr Gly Asn Glu Asp Gly Lys Val Ala Lys Leu Glu Val Trp
145                 150                 155
```

<210> SEQ ID NO 28
<211> LENGTH: 477

<212> TYPE: DNA
<213> ORGANISM: T. pseudonana

<400> SEQUENCE: 28

```
atggaagact atctgaaaaa tggagaggat gtggcacttc ctcctggggg atttgaggag    60
gctaccctga cttgtacaac gcaggatagg gtgtttatca agaagcggta tggctttgtg   120
aggctgtgtt tgaagtatgg agtggcgata cgaccagtct atgtgtttgg agagggaaga   180
ttgtttggca acgtacaagg aatgtggaag acaagacttg ccttgaatcg atggggcatt   240
ccgactatat tggtatgggg tagttggttc tttcccttgc ttccgaagaa gggtgtcaac   300
ctacatattg ttgttggaaa gcctttgatt gtgccaaaga ttgacaatcc aacaaaggaa   360
gaggttattg cgtggcatga aaagtatatt accgagttga agaggattta tgaagagtac   420
aaggaggttg cgtacggtaa cgaggacgga aaggttgcaa agcttgaggt ttggtga      477
```

<210> SEQ ID NO 29
<211> LENGTH: 376
<212> TYPE: PRT
<213> ORGANISM: T. pseudonana

<400> SEQUENCE: 29

```
Met Lys Tyr Arg Lys Leu Asn Leu Ala Thr Leu Pro Asp Glu Leu Phe
 1               5                  10                  15

Thr Lys Gln Thr Asp Val Lys Glu Trp Met Ala Leu Thr Thr Thr Ser
             20                  25                  30

Ala Glu Gly Gly Phe Pro Pro Ser Ser Leu Asn Lys Val Leu Pro Val
         35                  40                  45

Lys Arg Asp Ile Glu Ile Glu Arg Ile Ile Gly Thr Ser Tyr Tyr Met
     50                  55                  60

Ile Gly Asn Thr Val Pro Phe Ala Val Pro Leu Leu Ala Ala Ser
 65                  70                  75                  80

Tyr Phe Ser Ala Val Gly Ala Leu Ile Phe Lys Val Tyr Met Val Tyr
                 85                  90                  95

Phe Thr Thr Leu Phe Val Val Phe Thr Tyr Tyr Phe Tyr Pro Lys Tyr
            100                 105                 110

Met Lys Arg Tyr Asn Arg Pro Lys Ser Met Ser Lys Thr Asp Ile Lys
        115                 120                 125

Asp Asn Gln Tyr Leu Tyr Thr Glu Arg His Thr Gln Lys Tyr Leu Ser
    130                 135                 140

Met Gln Phe Val Trp Pro Glu Ser Ile Gln Arg Pro Ala Leu Asn Asp
145                 150                 155                 160

Gln Pro Val Ile Phe Ala Ala Ile Pro His Gly Leu Ser Pro Leu Gly
                165                 170                 175

Ile Thr Ala Tyr Pro Met Trp Ser Lys Leu Phe Asn Asp Lys Leu Cys
            180                 185                 190

His Trp Thr Cys Ala Pro Val Val Leu Lys Leu Pro Leu Ile Ser Ser
        195                 200                 205

Phe Met Lys Ala Ile Gly Tyr Ile Pro Ala Lys Ala Lys Asn Ile Thr
    210                 215                 220

Asp Thr Leu Ile Lys Lys Glu Asn Val Gly Ile Ile Leu Asp Gly
225                 230                 235                 240

Ile Ala Gly Met Phe Gln Ala His Asp Glu Val Ala His Val Lys Arg
                245                 250                 255

Arg Lys Gly Ile Ile Lys Ile Ala Leu Arg Ala Gly Ala Ala Val Val
            260                 265                 270
```

```
Pro Val Tyr Gly Phe Gly His Thr Ser Leu Trp Lys Ile Val Val Asp
            275                 280                 285

Pro Phe Gly Phe Leu Glu Trp Leu Ser Thr Lys Ser Asp Val Ser Val
290                 295                 300

Thr Pro Phe Phe Gly Arg Phe Asn Trp Phe Leu Gly Pro Pro Lys Arg
305                 310                 315                 320

Val Ala Val Cys Val Cys Met Gly Asp Ala Ile Lys Cys Pro Lys Ile
            325                 330                 335

Glu Glu Pro Thr Gln Gln Asp Ile Asp Lys Tyr His Gly Leu Leu Leu
            340                 345                 350

Lys Gly Tyr Asp Gln Leu Phe Glu Gln His Lys Val Ala Tyr Gly Trp
            355                 360                 365

Gly Asp Lys Lys Leu Gln Phe Val
370                 375

<210> SEQ ID NO 30
<211> LENGTH: 1131
<212> TYPE: DNA
<213> ORGANISM: T. pseudonana

<400> SEQUENCE: 30
atgaagtatc gcaaactcaa cctagccacc ctaccagacg aactcttcac caaacagaca      60
gatgtgaaag agtggatggc gcttaccaca acgtcagcgg aaggaggctt tccaccatcg     120
tcattaaaca aagtgttgcc tgtgaagaga gacatcgaga ttgaacgtat catcggcact     180
tcctactata tgattgggaa tacggttcca tttgcagttc cgcttctgtt ggctgcatcg     240
tactttagtg cagttggtgc tctgattttc aaggtgtaca tggtgtactt taccacactg     300
ttcgtagtgt tcacgtatta tttctaccca aagtacatga aacgatacaa tcgtccgaag     360
tccatgtcta agactgacat caaggacaac caatatctgt acacagaacg tcacacccaa     420
aagtatctct ccatgcaatt cgtgtggcca gaatcaatcc aaagaccagc tcttaacgat     480
caaccagtaa tctttgcagc cattccacat ggattaagcc cgttaggaat cacggcatat     540
ccaatgtggt caagttgtt caatgataaa ctttgccatt ggacttgtgc accagtggtg     600
ttgaagttgc ctttgatatc ttcgtttatg aaggctattg gttacattcc agcgaaagca     660
aagaatatca cggacacact gatcaagaag gaagagaatg ttggtatcat tcttgatgga     720
atcgctggaa tgtttcaggc tcatgatgaa gtggcacacg tgaagagaag gaaggggatt     780
atcaagattg cattgagggc cggagccgca gttgtacctg tgtacggttt cggtcatact     840
tcgttgtgga aaatcgtcgt tgatcccttt ggattcttgg aatggctgag tacaaaatcg     900
gatgtctctg tcacccttt cttcgggagg ttcaactggt ttttgggtcc tcgaaacga     960
gttgctgtct gtgtctgcat gggagacgca ataaagtgtc ctaagatcga ggaaccgacg    1020
caacaagaca ttgataagta tcatggactc ttattgaaag gatacgatca actatttgaa    1080
cagcacaaag tagcatacgg atggggtgat aagaaactgc agtttgttta a            1131

<210> SEQ ID NO 31
<211> LENGTH: 346
<212> TYPE: PRT
<213> ORGANISM: Chlamydomonas reinhardtii

<400> SEQUENCE: 31

Met Ala Gly Gly Lys Ser Asn Gly Thr Gly Ala Ala Asp Ala His Val
1               5                   10                  15
```

```
Arg Thr Ser His Leu Thr Leu Lys Ala Gly Glu Asp Pro Pro Asn
             20                  25                  30

Val Arg Ile Tyr Ser Asp Gly Ile Lys Pro Asp Ala Arg Gln Asn Leu
 35                  40                  45

Leu Val Gln Ile Leu Ala Gly Ile Thr Met Ser Ile Tyr Val Gly Phe
 50                  55                  60

Met Asn Tyr Phe Met Leu Leu Val Val Leu Ser Tyr Trp Ser Arg Ile
65                   70                  75                  80

Cys Arg Tyr Val Val Leu Ala Leu Leu Gly Thr Leu Ala Leu Pro Cys
                 85                  90                  95

Lys Pro Val Leu Trp Pro Ala Phe Asn Lys Leu Trp Ile Phe Lys Thr
            100                 105                 110

Trp Arg His Tyr Phe His Tyr Ser Phe Leu Ile Glu Glu Pro Leu Asp
            115                 120                 125

Pro Asn Lys Arg Tyr Ile Phe Val Glu Phe Pro His Gly Ala Phe Pro
            130                 135                 140

Ile Gly Pro Ile Val Ala Gly Thr Leu Met Gln Thr Leu Phe Pro His
145                 150                 155                 160

Met Met Ile Tyr Ser Val Ala Ala Ser Val Val Phe Tyr Ile Pro Phe
                165                 170                 175

Trp Arg His Phe Ile Thr Trp Ile Gly Ser Val Pro Ala Thr Pro Gly
            180                 185                 190

Asn Phe Lys Arg Leu Leu Lys Lys Gly Ser Val Ala Val Val Val Gly
            195                 200                 205

Gly Ile Ala Glu Met Tyr Met Gly Asn Lys Lys Glu Arg Ile Lys
210                 215                 220

Leu Val Gly Arg Arg Gly Phe Ala Arg Ile Ala Leu Glu Glu Gln Val
225                 230                 235                 240

Asp Gly Ile Val Cys Val Tyr Phe Gly Gln Ser Gln Val Leu Asp
                245                 250                 255

Phe Gly Pro Ser Trp Leu Ala Asp Phe Ser Arg Arg Met Arg Thr Ser
            260                 265                 270

Phe Gly Tyr Leu Thr Gly Trp Met Gly Leu Pro Val Pro Arg Pro Ile
            275                 280                 285

Pro Ile Tyr Met Val Asn Gly Lys Pro Ile Pro Val Pro Lys Val Ala
290                 295                 300

Arg Asp Ser Pro Glu Phe Asp Lys Glu Val Asp Lys Leu Leu Asp Ala
305                 310                 315                 320

Thr Ile Thr Glu Leu Gly Glu Met Tyr Asn Arg His Arg Gly Glu Tyr
                325                 330                 335

Gly Trp Gly Asp Arg Pro Leu Ser Ile Glu
            340                 345
```

<210> SEQ ID NO 32
<211> LENGTH: 1041
<212> TYPE: DNA
<213> ORGANISM: Chlamydomonas reinhardtii

<400> SEQUENCE: 32

```
atggcaggtg aaagtcaaa cggcacgggc gcggcggacg cgcacgtgcg tacctcgcac      60
ttgaccctga aagctgggga ggacccgccc ccgaatgttc gcatctacag tgacggcatc     120
aagccggacg cgcggcagaa cctgcttgtt cagatcctgg ccggcatcac gatgtcgatt     180
tatgtaggct tcatgaacta tttcatgctg ctggtggtgc tctcctactg gagccgcatc     240
```

```
tgccgctatg tggtcctggc gctgctaggc acactggcgc tgccctgcaa gcccgtgctg    300
tggcctgcct tcaacaagct gtggatcttc aagacctggc gtcactactt ccactacagt    360
ttcctgattg aggagccgct tgaccccaac aagcgctaca tctttgtcga gttcccgcac    420
ggcgcgttcc ccattggtcc catcgtggcg ggcacgctca tgcagactct gttcccgcac    480
atgatgatct acagcgtggc cgcctccgtc gtgttctaca tccccttctg gcgccatttc    540
atcacgtgga tcggctcggt gcccgcaacg cccggcaact tcaagcggct gctgaagaag    600
ggcagtgtgg cggtggtggt gggcggcatt gccgagatgt acatgggcaa caagaagaag    660
gagcgcatta agctagtggg ccgccgcggc ttcgcacgca tcgcgctgga ggagcaggtg    720
gacggcattg tgtgcgtgta ctacttcggt cagagccaag tgctggactt cgggccctcc    780
tggctggcgg actttagccg ccgcatgcgc accagcttcg gctacctcac gggatggatg    840
gggctgccgg tgccgcggcc catccccatc tacatggtga atgggaagcc catcccggtg    900
cccaaggtgg ctcgtgactc gcccgagttc gacaaggagg tggataagct gcttgacgcc    960
accatcacgg agctgggcga gatgtacaac aggcacagag gcgagtacgg ctggggcgac    1020
cgcccgctgt ccatcgagta g                                              1041

<210> SEQ ID NO 33
<211> LENGTH: 413
<212> TYPE: PRT
<213> ORGANISM: Chlamydomonas reinhardtii

<400> SEQUENCE: 33

Met Thr Pro Arg Asp Pro Pro Val Pro Arg Pro Pro Gly Val Arg
1               5                   10                  15

Gln Tyr Thr Asp Gly Arg Ser Ala Ser Tyr Val Leu Pro Leu Pro Tyr
                20                  25                  30

Arg Leu Leu Ala Gln Leu Thr Leu Gly Leu Tyr Val Gly Phe Pro Tyr
            35                  40                  45

Ile Leu Leu Gly Leu Leu Leu Gly Thr Ala Ala Gly Ser Arg Ala Ala
        50                  55                  60

Ala Ala Ala Leu Ala Leu Thr Leu Gly Ser Leu Leu Val Pro Ala Pro
65                  70                  75                  80

Pro His Ile Arg Gln Gly Met Leu Asp Ser Ala Leu Phe Arg Leu Trp
                85                  90                  95

Arg Ala Tyr Phe Asn Tyr Ser Tyr Ala Tyr Asp Gln Leu Pro Asp Phe
            100                 105                 110

Asn Arg Pro His Ile Phe Val Asn Ser Pro His Gly Ala Phe Pro Leu
        115                 120                 125

Ser Gln Ile Leu Cys Ile Ser Leu Ser Asn Ile Val Trp Pro Gly Phe
    130                 135                 140

Pro Val His Ser Leu Ala Ala Ser Val Leu Trp Tyr Ile Pro Leu Trp
145                 150                 155                 160

Arg His Met Lys Ala Ala Leu Gly Ala Ala Pro Ala Ser Arg Asp Asn
                165                 170                 175

Ala Arg Met Leu Leu Arg His Arg Gly Ser Val Ala Val Leu Ala Gly
            180                 185                 190

Gly Ile Ala Glu Met Tyr Thr Ser Ser Pro Ser Arg Ala Ala Ala Ala
        195                 200                 205

Thr Glu Pro Asp Glu Ala Ala Ala Gly Gly Ala Ile Asp Thr Thr
    210                 215                 220

Glu Ala Ala Gly Ala Thr Gly Ser Ser Ser Thr Thr Thr Ser Pro Pro
```

```
                    225                 230                 235                 240
            Gln Pro Lys Glu Gln Gln Arg Asp Gly Glu Gln Arg Gln Gly Pro Arg
                            245                 250                 255

Lys Gly Leu Lys Gly Leu Leu Lys Gly Pro Lys Asp Asp Pro Asp Pro
                        260                 265                 270

Ala Ala Glu Glu Gln Gly Leu Gly Leu Ala Pro Glu Arg Ile Lys
                    275                 280                 285

Leu Leu Gly Arg Arg Gly Phe Val Arg Leu Ala Val Glu Met Gly Val
                        290                 295                 300

Pro Ile Val Pro Ile Tyr His Met Gly Asn Ser Lys Ile Leu Thr Phe
            305                 310                 315                 320

Gly Pro Gln Ser Leu Gln Gln Leu Ser Arg Arg Leu Arg Met Ala Leu
                            325                 330                 335

Gly Ala Val Phe Gly Val Trp Gly Leu Pro Val Pro Arg Pro Gln Pro
                        340                 345                 350

Leu Met Met Cys Val Gly Ser Pro Ile Pro Val Pro Tyr Val Asp Pro
                            355                 360                 365

Ala Ala Glu Pro Glu Arg Phe Glu Ala Val Val Ala Ala Val His Gly
                        370                 375                 380

Gln Val Val Ala Ala Phe Gln Asp Leu Tyr Asn Arg Tyr Arg Val Gln
            385                 390                 395                 400

Tyr Gly Cys Gly Trp Glu Arg Arg Pro Leu Glu Val Cys
                            405                 410

<210> SEQ ID NO 34
<211> LENGTH: 1241
<212> TYPE: DNA
<213> ORGANISM: Chlamydomonas reinhardtii

<400> SEQUENCE: 34
atgaccccgc gggatccgcc ggtgccgcgg ccgccgccgg gcgtacggca gtacactgac      60
ggccggtcgg cgtcgtacgt actgccgctg ccgtatcgcc tgctggccca gctgactctg     120
ggtttgtacg tgggctttcc ctacatcctg ctggggttgt tgctgggcac ggctgccggc     180
tcgcgcgccg ccgccgccgc cctggctctg acgctgggca gctgctggt gccggcccca     240
ccgcacatcc ggcagggcat gctggactcg cactgttca ggctgtggcg cgcctacttc      300
aactacagct acgcctacga ccaactgccc gacttcaacc gcccacacat ctttgtcaac     360
agcccgcacg cgccttccc gctgtcgcag atcctgtgca tctccctgtc caacatcgtg      420
tggccgggct tccccgtgca cagcctggcg gcctcggtgc tgtggtacat accgctgtgg     480
cgccacatga aggcggcgct ggggccgcg cccgccagcc gggacaacgc gcgcatgctg      540
ctgaggcacc gcgggtcggt ggcggtgctg cgggcggca ttgcggagat gtacacgtca      600
tcgccctccc gcgccgccgc tgccaccgaa ccagatgagg ctgcggctgc gggtggggcg     660
atcgacacga ctgaagccgc cggcgccacc ggctcaagca gcaccaccac tagcccgccg     720
cagccaaagg agcagcagcg cgatggggag cagcgccagg ggccgcgcaa ggggctgaag     780
gggctgctga aaggcccgaa ggacgatccc gatccggcgg cggaggagga gcagggcctc     840
gggttggcac ctgaacgcat caagctgctg gccggcgcg gcttcgtgcg gctggcggtg     900
gagatgggtg tgcccattgt acccatatac cacatgggca acagcaagat cctgaccttc     960
gggccgcagt cactgcagca gctgtcgcgc gcctgcgca tggcgctggg cgccgtgttc    1020
ggcgtgtggg gcctgcctgt gccgcgcccc cagccgctca tgatgtgtgt gggcagcccc    1080
```

```
attcccgtgc cgtacgtgga tccagccgcc gagccggagc gcttcgaggc cgtggtggcg      1140
gcggtgcacg ggcaggtggt ggcggccttt caggatctgt acaacaggta ccgcgtgcag      1200
tacggctgcg gttgggagcg ccggccgctg gaggtgtgct g                         1241
```

<210> SEQ ID NO 35
<211> LENGTH: 320
<212> TYPE: PRT
<213> ORGANISM: Chlamydomonas reinhardtii

<400> SEQUENCE: 35

```
Met Gln Ser Lys Arg Cys Ala Glu Leu Ala Ser Gly Ala Leu Trp Pro
1               5                   10                  15

Met Asp Arg Asp Gln Met Arg Asp Arg Asp Pro Trp Lys Leu Arg Asp
            20                  25                  30

Arg Ala Ile Ser Gln Ala Trp Val Trp Pro Leu Leu Ile Gly Thr Leu
        35                  40                  45

Leu Tyr Val Gln Ser Thr Thr Leu Thr Ile Ala Phe Leu Leu Trp His
    50                  55                  60

Ile Trp Lys Val Met Ala Ser Tyr Phe Pro Gly Ala Arg Leu Ile Lys
65                  70                  75                  80

Thr Ala Asp Leu Asp Pro Ala Gly Arg Tyr Ile Phe Val Ser His Pro
                85                  90                  95

His Gly Val Ile Ala Ile Ser Asp Trp Leu Ala Phe Ala Thr Glu Ala
            100                 105                 110

Leu Gly Phe Ser Lys Leu Phe Pro Gly Leu Asp Leu Arg Cys Ala Thr
        115                 120                 125

Leu Ala Ser Asn Phe Trp Val Pro Gly Leu Arg Glu Tyr Ile Leu Ser
    130                 135                 140

His Gly Met Cys Gly Val Gly Arg Asp Thr Leu Ala Arg Val Leu Thr
145                 150                 155                 160

Gly Lys Pro Gly Arg Ala Val Val Leu Val Val Gly Gly Ala Ser Glu
                165                 170                 175

Ala Leu Leu Ala Ala Glu Gly Thr Tyr Asp Leu Val Leu Arg Asn Arg
            180                 185                 190

Lys Gly Phe Val Arg Leu Ala Leu Gln Thr Gly Ala Ser Leu Val Pro
        195                 200                 205

Val Leu Ser Tyr Gly Glu Thr Asp Thr Phe His Thr Tyr Ile Pro Pro
    210                 215                 220

Pro Cys Ser Arg Ala Ala Ala Val Met Lys Val Leu Lys Gln Val Phe
225                 230                 235                 240

Gly Phe Ser Thr Pro Leu Cys Trp Gly Thr Gly Leu Phe Gly Gly Trp
                245                 250                 255

Gly Met Leu Ala Leu Gln Val Pro Leu Thr Val Val Gly Ala Pro
            260                 265                 270

Ile Gln Val Asp Lys Val Ser Ser Pro Thr Glu Ala Glu Val Ala Ala
        275                 280                 285

Leu His Lys Thr Tyr Thr Glu Ala Leu Gln Lys Leu Trp Asp Asp Thr
    290                 295                 300

Val Asp Lys Tyr Gly Lys Gly Val Lys Arg Pro Leu Ala Ile Val Gln
305                 310                 315                 320
```

<210> SEQ ID NO 36
<211> LENGTH: 963
<212> TYPE: DNA
<213> ORGANISM: Chlamydomonas reinhardtii

<400> SEQUENCE: 36

```
atgcaaagta agcgttgtgc agagctggcc tctggggctc tgtggcccat ggaccgcgac    60
cagatgcgcg accgcgaccc atggaagctg cgcgaccgag ctataagcca agcatgggtg   120
tggcctctgc tcatcggcac attgctttac gtgcagagca ccacgctcac aattgccttc   180
ctgctgtggc atatctggaa ggttatggcc tcttacttcc ccggcgcccg cctgattaag   240
accgccgacc tggatccggc tggccgctat atattcgtga ccacccgca cggcgtcatc    300
gccatttccg actggctggc atttgccaca gaggcgctgg gcttctccaa actgttccca   360
ggcctggacc tgcgctgcgc cacgctggct tcaaacttct gggtgcctgg tttgcgtgag   420
tacatcctat cgcacggcat gtgcggcgtg gggcgagaca ctctggcgcg cgtgctgaca   480
ggaaagccgg ccgtgcggt tgtgttggtg gtgggcggcg cgtctgaggc gctgttggcg    540
gcggagggaa cttatgacct ggtgctgcgc aaccgcaagg gctttgtgcg cctggcgctg   600
cagaccggcg ccagtctggt gccggtgctg tcgtacggtg agacagacac cttccacacc   660
tacatcccgc cgccctgcag ccgggcggcc gcggtcatga aggtgctgaa gcaggtgttt   720
ggcttctcca cgcccctgtg ctggggcacc ggactgttcg ggggctgggg catgctagcg   780
ctgcaggtgc cgctcactgt ggtggtgggg gcacccatac aggtggacaa ggtgtccagt   840
cccacggagg ctgaggtggc ggcgctgcat aagacctaca cggaggcact gcagaagctg   900
tgggatgaca cagtggacaa gtacggcaag ggtgtcaagc ggccgctggc catcgtgcaa   960
tga                                                                963
```

<210> SEQ ID NO 37
<211> LENGTH: 324
<212> TYPE: PRT
<213> ORGANISM: Chlamydomonas reinhardtii

<400> SEQUENCE: 37

```
Met Ala Ile Asp Lys Ala Pro Thr Asn Val Arg Ile Trp Ser Asp Gly
1               5                   10                  15

Val Thr Glu Lys Gly Lys Gln Ser Ile Phe Ser Ser Leu Val Ala Met
            20                  25                  30

Leu Thr Leu Phe Ile Tyr Cys Gly Trp Met His Val Leu Leu Ala Leu
        35                  40                  45

Val Ile Leu Ser Phe Trp Tyr Arg Trp Ala Leu Val Thr Val Leu Leu
    50                  55                  60

Leu Tyr Ser Thr Leu Leu Leu Pro Pro Lys Pro Val Leu Trp Gly Pro
65                  70                  75                  80

Val Cys Arg Ser Trp Ile Phe Gln Thr Trp Arg Glu Tyr Phe Lys Phe
                85                  90                  95

Ser Tyr Val Phe Asp Glu Val Leu Asp Ser Lys Lys Tyr Ile Phe
            100                 105                 110

Ala Glu Phe Pro His Gly Val Phe Pro Met Gly Pro Leu Ile Gly Ala
        115                 120                 125

Thr Glu Cys Gln Ile Met Phe Pro Gly Phe Asp Ile Phe Gly Leu Ala
    130                 135                 140

Ala Asn Val Val Phe Thr Val Pro Phe Trp Arg His Phe Val Ala Trp
145                 150                 155                 160

Leu Gly Ser Val Pro Ala Thr Thr Arg Asp Phe Lys Arg Val Leu Lys
                165                 170                 175

Gln Gly Ser Val Ala Val Ile Val Gly Gly Ile Ala Glu Met Tyr Met
```

|  | 180 |  |  |  | 185 |  |  |  | 190 |  |  |
|---|---|---|---|---|---|---|---|---|---|---|---|
| Gln | Ser | Pro | Thr | Lys | Glu | Gln | Ile | Met | Leu | Lys | Asp | Arg | Lys | Gly | Phe |
|  |  |  | 195 |  |  |  |  | 200 |  |  |  | 205 |  |  |  |

Val Arg Val Ala Val Glu Glu Gly Val Asp Gly Gly Ile Val Pro Val
        210                 215                 220

Tyr His Phe Gly Asn Ser Gln Val Leu Asp Phe Gly Pro Gln Ala Met
225                 230                 235                 240

Ala Ser Val Ser Arg Arg Leu Arg Ala Ala Leu Gly Phe Leu Tyr Gly
                245                 250                 255

Val Ala Tyr Leu Pro Leu Pro Arg Arg Arg Asn Ile Tyr Met Val Cys
            260                 265                 270

Gly Lys Pro Val Pro Val Thr Arg Thr Ala Arg Asp Asp Pro Lys Phe
        275                 280                 285

Glu Glu Val Val Asp Ala Thr His Ala Ala Val Met Ala Ala Leu Gln
        290                 295                 300

Glu Ala Tyr Asp Arg His Lys Thr Glu Tyr Gly Trp Ala Asp Arg Pro
305                 310                 315                 320

Leu Val Ile Ser

<210> SEQ ID NO 38
<211> LENGTH: 975
<212> TYPE: DNA
<213> ORGANISM: Chlamydomonas reinhardtii

<400> SEQUENCE: 38

```
atggcgattg ataaagcacc gacaaatgtg cgaatttgga gcgatggcgt cacggagaag    60
ggcaagcaaa gcatcttctc atcgctggtg gctatgttga cgctcttcat ctactgtggc   120
tggatgcatg tgctgctggc gcttgtgatc ctgtccttct ggtaccgctg ggcgctggtg   180
acggtgctgc tgctgtactc caccctgctg ctgccgccta agccggtgct gtggggaccg   240
gtctgtcgct cctggatctt ccagacctgg cgggagtact tcaagttctc ttacgtgttt   300
gatgaggtgc tggactcgaa gaagaagtac atcttcgcgg agttcccgca cggtgtcttc   360
cccatgggcc cactcattgg cgccacagaa tgccagatca tgtttcccgg ctttgacatc   420
ttcgggctgg cggcgaatgt ggtgttcacg gtccccttct ggcggcattt cgtggcgtgg   480
ctgggctccg tgccgccacc cacacgcgac ttcaagcggg tgctgaagca aggaagcgtg   540
gcggtcatcg tgggaggcat cgcagagatg tacatgcaga gccccacgaa ggagcagatc   600
atgttgaagg accgcaaggg ctttgttcgt gtggcggtgg aggagggcgt ggatggcggc   660
atcgtgccgg tctaccactt tggcaactct caggtgctgg acttcggccc ccaggccatg   720
gccagtgtgt cccgccggct gcgtgcggcc ctgggcttcc tgtacggagt ggcctacctg   780
cccctgccca ggcgccgcaa catttacatg gtgtgcggca gcccgttcc  cgtcacgcgc   840
accgcccgcg acgaccccaa gtttgaggag gtggttgacg ccactcacgc cgctgtgatg   900
gcggccctgc aggaggccta cgaccgccac aagaccgagt acggctgggc cgaccgaccg   960
ctggtcatca gctga                                                    975
```

<210> SEQ ID NO 39
<211> LENGTH: 327
<212> TYPE: PRT
<213> ORGANISM: Chlamydomonas reinhardtii

<400> SEQUENCE: 39

Met Pro Leu Ala Lys Leu Arg Asn Val Val Leu Glu Tyr Ala Ala Ile

```
              1               5                  10                 15
        Ala Ile Tyr Val Ser Ala Ile Tyr Thr Ser Val Val Leu Leu Pro Ser
                            20                  25                 30

Ala Leu Ala Leu Phe Tyr Leu Phe Gly Ala Thr Ser Pro Ser Ala Trp
                            35                  40                 45

Leu Leu Leu Ala Ala Phe Leu Ala Leu Thr Phe Thr Pro Leu Gln Leu
                            50                  55                 60

Thr Thr Gly Ala Leu Ser Glu Arg Phe Val Gln Phe Ser Val Ala Arg
         65                  70                  75                 80

Ala Ala Ala Tyr Phe Pro Thr Arg Val Val Thr Asp Pro Glu Ala
                                85                  90                 95

Phe Arg Thr Asp Arg Gly Tyr Leu Phe Gly Phe Cys Pro His Ser Ala
                           100                 105                110

Leu Pro Ile Ala Leu Pro Ile Ala Phe Ala Thr Thr Ser Pro Leu Leu
                           115                 120                125

Pro Lys Glu Leu Arg Gly Arg Thr His Gly Leu Ala Ser Ser Val Cys
             130                 135                 140

Phe Ser Ala Pro Ile Val Arg Gln Leu Tyr Trp Trp Leu Gly Val Arg
        145                 150                 155                160

Pro Ala Thr Arg Gln Ser Ile Ser Gly Leu Leu Arg Ala Arg Lys Val
                            165                 170                 175

Ala Val Leu Val Pro Gly Gly Val Gln Glu Val Leu Asn Met Glu His
                            180                 185                 190

Gly Lys Glu Val Ala Tyr Leu Ser Ser Arg Thr Gly Phe Val Arg Leu
                            195                 200                 205

Ala Val Gln His Gly Ala Pro Leu Val Pro Val Trp Ala Phe Gly Gln
             210                 215                 220

Thr Arg Ala Tyr Ser Trp Phe Arg Pro Gly Pro Leu Val Pro Thr
        225                 230                 235                240

Trp Leu Val Glu Arg Ile Ser Arg Ala Ala Gly Ala Val Pro Ile Gly
                            245                 250                 255

Met Phe Gly Gln Tyr Gly Thr Pro Met Pro His Arg Glu Pro Leu Thr
                            260                 265                 270

Ile Val Val Gly Arg Pro Ile Pro Val Pro Glu Leu Ala Pro Gly Gln
                            275                 280                 285

Leu Glu Pro Glu Pro Glu Val Leu Ala Ala Leu Leu Lys Arg Phe Thr
             290                 295                 300

Asp Asp Leu Gln Ala Leu Tyr Asp Lys His Lys Ala Gln Phe Gly Lys
        305                 310                 315                320

Gly Glu Glu Leu Val Ile Met
                            325
```

<210> SEQ ID NO 40
<211> LENGTH: 984
<212> TYPE: DNA
<213> ORGANISM: Chlamydomonas reinhardtii

<400> SEQUENCE: 40

```
atgccgctcg caaagctgcg aaacgtggtg ctggagtacg cggccatagc catctacgtc      60
agcgccatct acacctcggt ggtgctgctg ccctcggcgc tcgcgctgtt ctacctgttt     120
ggggccacca gccctcggc ctggctgctg ctagccgcct tcctggccct caccttcacg     180
ccgctgcagc tgaccaccgg tgcgctgtcg gagcggttcg tgcagttcag tgtggcgcgg     240
gcggcggcct acttccccac ccgcgtggtg gtcacggacc cggaggcctt ccgcactgac     300
```

```
cgcggctact tgttcggatt ctgcccgcac tcggctctgc ccatcgcact gcccatcgcc    360
ttcgccacca cctcgccgct gctgcccaag gagctgcgcg ccgcacaca cggcttggcg    420 tcgtccgtgt gcttcagcgc gcccatagtg cggcagctgt actggtggct gggcgtgcgg    480
cccgccacgc ggcagagcat cagcggcctg ttgcgggcgc gcaaggtggc ggtgctggtg    540
ccggggggcg tgcaggaggt gctcaacatg gagcacggca aggaggtggc ctacctctcc    600
agccgcaccg gcttcgtgcg actggccgtg cagcacggcg cgccgctggt gccagtgtgg    660
gcgttcggcc agacgcgcgc gtacagctgg ttccggccgg ggccgccgct cgtgcccacg    720
tggctcgtgg agcgcatctc acgtgccgcc ggcgccgtac ccatcggcat gtttgggcag    780
tacggcacgc ccatgccgca ccgcgagccc ctcaccattg tggtgggtcg ccccatcccg    840
gtgccggagc tggcgccggg ccagctcgag cccgagcccg aggtgctggc ggcgctcctc    900
aagcgcttca cggacgacct gcaggcgctg tacgacaagc acaaggcgca gttcggcaag    960
ggcgaggagc tggtcataat gtag    984
```

```
<210> SEQ ID NO 41
<211> LENGTH: 469
<212> TYPE: PRT
<213> ORGANISM: Ostreococcus lucimarinus

<400> SEQUENCE: 41

Met Arg Ala Pro Ala Asp Ala Ala Ile Asp Trp Arg Ala Pro Ser Ala
1               5                   10                  15

Gly Ala Leu Ala Cys Leu Leu Ala Val Ala Ile Thr Asn Phe Gly Val
            20                  25                  30

Gly Gly Ala Leu Phe Gly Gly Arg Gly Trp Arg Ala Trp Gln Pro Phe
        35                  40                  45

Ala Arg Gly Arg Ser Trp Arg Phe Thr Leu Ala Gln Ala Ile Gly Trp
    50                  55                  60

Thr Leu Ala Ser Ala Ser Leu Ala Cys Val Met Ala Cys Gly Thr Leu
65                  70                  75                  80

Val Trp Arg Asp Ala Arg Asp Ala Arg Asp Gly Thr Arg Glu Arg
                85                  90                  95

Arg Leu Ala Val Ala Ala Leu Ser Trp Thr Ser Leu Gly Leu Ser Val
            100                 105                 110

Ala Ser Glu Ala Ala Val Ala Ala Ser Leu Ala Phe Phe Asp Val Gln
        115                 120                 125

Asp Glu Gly Glu Ala Gly Arg Gly Ala Ala Arg Gly Arg Glu Gly Leu
    130                 135                 140

Asp Phe Arg Asp Val Ala Arg Val Ala Thr Leu Leu Ser Ile Ala His
145                 150                 155                 160

Val Leu His Ala Pro His Ala Val Ile Phe Ala Thr Leu Ala Thr Val
                165                 170                 175

Tyr Ala Leu Gly Ser Ser Gly Ala Leu Ala Ser Ile Val Val Leu Tyr
            180                 185                 190

Ala Ser Thr Tyr Phe Leu Gln Arg Asp Leu Glu Arg Gly Arg Arg Lys
        195                 200                 205

Trp Asp Ala Phe Arg Ala Trp Ser Ser Arg Trp Ile Glu Gly Ala Ala
    210                 215                 220

Lys Ala Trp His Gly Ser Val Arg Met Ile His Asp Gly Ala His Gly
225                 230                 235                 240

Ala Gly Ser Thr Pro Leu Val Phe Ala Tyr His Pro His Ser Leu Ile
```

```
              245                 250                 255
Pro Ala Gly Ala Val Trp Phe His Phe Leu Pro Gln Phe Gly Arg Arg
            260                 265                 270

Phe Glu Asn Val Lys Pro Val Thr Leu Ala Ala Ser Val Leu Phe Lys
            275                 280                 285

Pro Pro Phe Val Arg Glu Leu Ala Ala Trp Leu Gly Val Arg Ser Val
            290                 295                 300

Ser Gln Glu Ile Phe Arg Ser Thr Leu Arg His Glu Arg Ala Val Val
305                 310                 315                 320

Val Cys Pro Gly Gly Gln Gly Glu Met Cys Glu His Val Gly Gly Leu
                325                 330                 335

Lys Glu Glu Thr Ile Thr Leu Cys Thr Lys His Arg Gly Phe Val Arg
            340                 345                 350

Leu Ala Ile Glu Glu Lys Ala Arg Leu Val Pro Val Val Cys Phe Gly
            355                 360                 365

Glu Ser Ser Ser Trp Arg Asn Leu Leu Arg His Pro Gly Arg Tyr Leu
        370                 375                 380

Tyr Arg Arg Phe Arg Val Ala Thr Pro Leu Leu Ala Val Gly Tyr Leu
385                 390                 395                 400

Gly Ile Leu Pro Ile Pro Ala Arg Val Pro Leu Thr Phe Val Val Gly
                405                 410                 415

Asp Pro Met Ser Leu Pro Glu Pro Asp Asp Ala Gly Arg Ala Arg Glu
            420                 425                 430

Ser Asp Val Glu Ile Ala His Ala Ala Tyr Tyr Arg Glu Val Ala Arg
        435                 440                 445

Leu Phe Ala Lys His Lys Gly Ala Ser Gly Phe Pro Asn Leu Asn Leu
    450                 455                 460

Lys Leu Leu His Glu
465

<210> SEQ ID NO 42
<211> LENGTH: 1410
<212> TYPE: DNA
<213> ORGANISM: Ostreococcus lucimarinus

<400> SEQUENCE: 42
atgcgcgcgc cgcggacgc ggcgatcgat tggcgcgcgc cgtccgcggg cgcgctcgcg      60
tgcctgctcg cggtggcgat cacgaacttt ggcgtcggtg gcgcgctgtt cggaggacga     120
ggatggcgcg cgtggcaacc gttcgcgcga ggacgatcgt ggaggttcac gctggcgcaa     180
gcgatcggat ggacgctggc gagcgcgtcg ctggcgtgcg tgatggcgtg cgggacgctg     240
gtgtggcgag acgcgaggga cgcgagggac gacgggacgc gcgagcggcg actggcggtg     300
gcggcgctga gttggacgag cctgggactg agcgtcgcga gcgaggcggc ggtggcggcg     360
tcgctggcgt tcttcgacgt ccaggacgag ggcgaggcgg ggcgaggcgc ggcgagggga     420
agggaaggtt tggattttag agacgtcgcg cgcgtcgcga cgctgttgtc catcgcgcac     480
gtgttgcacg cgccgcacgc ggtgattttc gcgacgctgg cgacggtgta cgcgctcggg     540
tcgtcgggag cgctggcgtc catcgttgtt ctgtacgcga gcacgtattt cttgcagcgc     600
gatctcgagc gcgggcgccg gaagtgggac gcgtttcgag cgtggtcgtc gcgatggata     660
gagggcgcgg cgaaggcgtg gcacgggagc gtgcgcatga ttcacgacgg cgcgcacggc     720
gcgggctcga cgcctctcgt ctttgcctat cacccgcact cgctcattcc ggcgggcgcc     780
gtgtggtttc acttttttacc tcagtttggt cgtcgctttg aaaacgtcaa gcccgtgacg     840
```

```
ttggccgcga gcgttctttt caagccgccg ttcgtgcgag agctcgccgc gtggttgggc    900
gtgcgcagcg tgtcgcaaga aatatttcgt tcgacgcttc gtcacgagcg cgcggtcgtc    960
gtgtgtccgg gcggtcaggg cgagatgtgc gagcacgtcg gcggattgaa ggaggagacc   1020
atcacgctct gcacgaaaca tcgcgggttc gttcgactcg ccatcgaaga aaaagcgcgt   1080
ctcgtgcccg tcgtgtgttt cggcgagagt agcagctggc gcaatctctt gcggcacccc   1140
ggtcgatatt tgtacagacg cttcgcgtc gcgacgccgc ttttagcggt gggctacctc    1200
ggcattctcc cgattccggc ccgagtgccg ctcacgttcg tcgtcggcga cccgatgtcg   1260
cttcccgagc ccgatgacgc gggacgagcg agggagagcg acgttgagat cgctcacgcg   1320
gcgtattacc gcgaggtggc gcgcttgttc gcaaagcaca agggcgcgag cggatttccg   1380
aatttaaact tgaaattgct gcacgagtga                                    1410
```

<210> SEQ ID NO 43
<211> LENGTH: 316
<212> TYPE: PRT
<213> ORGANISM: Ostreococcus lucimarinus

<400> SEQUENCE: 43

```
Met Phe Ala Trp Leu Gly Leu Ile His Val Asp Val Ala Val Thr Ala
1               5                   10                  15

Leu Ala Val Trp Thr Leu Pro Ser Ala Met Ala Val Thr Ala Leu Ala
            20                  25                  30

Thr Leu Val Ala Ala Ala Ile Pro Arg Thr Val Ala Thr Pro Arg
        35                  40                  45

Trp Gly Ala Arg Leu Ala Arg Ala Val Thr Arg Thr Ala Thr Ala Tyr
    50                  55                  60

Phe Pro Thr Arg Leu Glu Phe Glu Asp Glu Ala Tyr Leu Arg Ala
65                  70                  75                  80

Val Arg Asn Glu Glu Ala Cys Val Ile Gly Leu Glu Pro His Gly Val
                85                  90                  95

Leu Pro Leu Ser Val Ile Ser Phe Ala Glu Tyr Phe Met His Asp Glu
            100                 105                 110

Glu Gly Ala Arg Arg Arg Gly Leu Thr Pro Ala Ala Arg Arg Gly Ala
        115                 120                 125

Arg Ala Leu Ala Ser Ala Ala Ile Phe Lys Val Pro Leu Val Lys His
    130                 135                 140

Leu Trp Thr Trp Leu Gly Leu Asp Pro Ile Ser Lys Ala Cys Met Leu
145                 150                 155                 160

Arg Met Leu Arg Ala Gly Lys Thr Ala Val Ile Ile Pro Gly Gly Val
                165                 170                 175

Ala Glu Cys Met Ala Met Glu Arg Gly Val Thr Leu Tyr Leu Arg
            180                 185                 190

Lys Arg Tyr Gly Phe Val Lys Ile Ala Ile Val Thr Gly Ala Lys Leu
        195                 200                 205

Ile Pro Ala Tyr Thr Phe Gly Gln Ser Arg Thr Tyr Gly Tyr Trp Arg
    210                 215                 220

Leu Gly Pro Pro Ile Val Pro Lys Phe Val Ala Asp Trp Ile Gly Lys
225                 230                 235                 240

Thr Phe Ser Phe Ala Pro Ile Ile Phe Trp Gly Lys Phe Cys Thr Pro
                245                 250                 255

Ile Pro Tyr Ala Thr Ala Leu Asn Thr Val Val Gly Lys Pro Ile Glu
            260                 265                 270
```

Val Glu Lys Asn Pro Asp Pro Ser Lys Glu Val Gln Ala Lys Leu
        275                 280                 285

Asp Glu Phe Ile Asp Ala Met Arg Ser Leu Tyr Asp Ser His Lys Ala
    290                 295                 300

Arg Phe Gly Tyr Glu Asp Val Arg Leu Val Ile Cys
305                 310                 315

<210> SEQ ID NO 44
<211> LENGTH: 951
<212> TYPE: DNA
<213> ORGANISM: Ostreococcus lucimarinus

<400> SEQUENCE: 44

| | | | | | |
|---|---|---|---|---|---|
| atgttcgcgt | ggctcggatt | gattcacgtc | gacgtcgcgg | tgacggcgct | ggcggtgtgg | 60 |
| acgctgccga | gcgcgatggc | ggtgacggcg | ctcgcgacgc | tggtcgcggc | ggcggcgatc | 120 |
| ccgcggacgg | tggcgacgcc | gaggtggggc | gcgcggttgg | cgcgcgcggt | gacgaggacg | 180 |
| gcgacggcgt | actttccgac | gcgattggaa | ttcgaagacg | aggaggcgta | tctgcgagcg | 240 |
| gtgaggaacg | aagaggcgtg | cgtgatagga | ctggaaccgc | acggggtgct | gccgctgagc | 300 |
| gtgatatcgt | tcgcggagta | ttttatgcac | gatgaggagg | gggcgcggcg | acgaggattg | 360 |
| acgccggcgg | cgagacgagg | cgcgcgggcg | ctggcgagcg | cggcgatatt | taaagtcccg | 420 |
| ctcgtgaaac | atctgtggac | gtggttgggg | ttggatccga | tctcgaaggc | gtgcatgctg | 480 |
| aggatgctgc | gagcggggaa | gacggcggtg | atcattcccg | gcggcgtcgc | cgagtgcatg | 540 |
| gcgatggaac | gcgcgtgga | gacgttgtat | ttgcgcaagc | gatacggatt | cgtgaagatc | 600 |
| gccatcgtga | ccggagcgaa | actgattccc | gcgtacacgt | tcggacaaag | tcggacgtac | 660 |
| gggtactggc | ggctcgggcc | gccgatcgtg | ccgaaattcg | tggcggattg | gatcgggaag | 720 |
| acgttttcgt | tcgcgccgat | tatttttctgg | gggaaatttt | gcacgcccat | cccgtacgcg | 780 |
| acggcgctca | cacggtcgt | gggcaaaccg | atcgaggttg | aaaaaaaccc | agatccgagc | 840 |
| aaggaagagg | ttcaggcgaa | attggacgag | tttatcgacg | ccatgcgttc | gctgtacgac | 900 |
| agtcacaagg | cgagattcgg | ttacgaagac | gttcgactcg | tgatttgtta | g | 951 |

<210> SEQ ID NO 45
<211> LENGTH: 338
<212> TYPE: PRT
<213> ORGANISM: Ostreococcus lucimarinus

<400> SEQUENCE: 45

Met Ile Tyr Ala Trp Ile Leu Ser Ala Ile Phe Val Tyr Pro Ala Tyr
1               5                   10                  15

Cys Val Phe Gly Pro Ser Met Trp Leu Lys Asn Phe Leu Gly Tyr
            20                  25                  30

Ile Ala Trp Tyr Ala Thr Leu Asp Arg Lys Thr Ala Ser Ser Gly Lys
        35                  40                  45

Arg Phe Ala Arg Trp Ser Arg Arg Leu Pro Phe Trp Arg Ile Leu Ala
    50                  55                  60

Glu Tyr Phe Pro Val Arg Leu His Val Ser Ala Lys Leu Asp Pro Ser
65                  70                  75                  80

Gly Asn Tyr Leu Phe Gly Tyr His Pro His Gly Val Ile Gly Val Gly
                85                  90                  95

Ala Leu Leu Thr Phe Ala Thr Glu Ala Thr Gly Phe Tyr Glu Ala Phe
            100                 105                 110

Pro Gly Leu Asp Leu Arg Leu Leu Thr Leu Ser Met Asn Phe Lys Phe
        115                 120                 125

Pro Phe Thr Arg Glu Val Leu Met Gly Leu Gly Ile Asn Ser Val Thr
    130                 135                 140

Lys Ser Ser Val Glu Thr Asn Leu Thr Arg Ala Pro Gly Ala Ser Val
145                 150                 155                 160

Ala Ile Val Ile Gly Gly Ala Ser Glu Ala Leu Asp Ala Arg Pro Gly
                165                 170                 175

Trp Ala Thr Leu Thr Leu Ala Arg Arg Lys Gly Phe Val Lys Met Ala
            180                 185                 190

Leu Arg Thr Gly Ala Ser Leu Val Pro Val Phe Ala Phe Gly Glu Asn
        195                 200                 205

Asp Ile Phe Glu Gln Val Glu Asn Pro Glu Gly Gly Arg Leu Arg Asn
    210                 215                 220

Phe Gln Met Tyr Ile Lys Gln Leu Ile Gly Ile Thr Pro Pro Ala Phe
225                 230                 235                 240

Tyr Gly Arg Ser Leu Ser Arg Gly Met Trp Arg Arg Ile Phe Gly Arg
                245                 250                 255

Lys Gly Val Leu Pro Lys Arg Glu Pro Ile Glu Val Val Gly Asn
            260                 265                 270

Pro Ile Ala Val Pro Lys Val Val Asp Pro Ser Asn Glu Ile Ile Asp
        275                 280                 285

Lys Tyr His Ala Leu Tyr Thr Glu Ser Leu Lys Glu Leu Tyr Glu Leu
    290                 295                 300

His Arg Arg Gln Phe His Arg Leu Asn Arg Gly Gly Ser Ser Asp Asp
305                 310                 315                 320

Leu Leu Ser Asp Leu Leu Thr Arg Gln Gly Lys Leu Gln Asn Met Gln
                325                 330                 335

Phe Lys

<210> SEQ ID NO 46
<211> LENGTH: 1017
<212> TYPE: DNA
<213> ORGANISM: Ostreococcus lucimarinus

<400> SEQUENCE: 46
atgatatacg cgtggatact gagcgcgata ttcgtatatc ccgcgtattg cgtgttcggg      60
ccgtcgatgt ggttgaagaa tttcttcctg gggtacatcg cgtggtacgc gacgctcgac     120
aggaagacgg cgagctcggg gaagcgtttc gctcgatggt ctcggcggtt accgttttgg     180
aggattttgg cggagtattt tccggtgcga ttacacgtga gcgcgaagtt agatccgagc     240
ggtaattact tgttcggtta tcatccgcac ggcgtcatcg cgtcggcgc gttgttgacg     300 ttcgccaccg aggcgacggg attttacgaa gcatttccgg gactcgattt gcgtcttctc     360
acgctgtcca tgaacttcaa gttcccgttc actcgcgagg tgttgatggg gctcgggatc     420
aatagcgtga ccaagtcgag cgtggagacg aatctgacgc gcgcgccggg ggcgtccgtc     480
gccatagtca tcggcggcgc ctccgaagcg ttggacgcgc gtccgggctg ggccacgctc     540
acgctcgcca gacgcaaggg gttcgtaaag atggctcttc gcacaggagc atcgctcgtg     600
cccgtgttcg cgttcggcga gaatgacatc ttcgaacaag tggaaaatcc cgaaggcgga     660
cgattgagga atttccaaat gtacatcaaa caactcattg gcatcacgcc gcctgctttt     720
tacgggcggt cgctcagtcg aggcatgtgg cgtcgaatct tggtcgcaa aggtgtgctt     780 ccgaagcgtg agccgatcga agtcgtcgtg ggcaatccca tcgccgtgcc caaagtcgtc     840

```
gatccgtcaa acgaaatcat cgacaagtac cacgccctgt acaccgaatc tttgaaagag    900
ctttacgagt acatcgtcg acagtttcat agactcaatc gcgggggtc gtcggatgat     960 cttctgagcg atctcctgac tcggcaagga aaactgcaaa acatgcagtt caagtag     1017
```

<210> SEQ ID NO 47
<211> LENGTH: 350
<212> TYPE: PRT
<213> ORGANISM: Ostreococcus lucimarinus

<400> SEQUENCE: 47

```
Met Gly Ser Asn Ala Gln Arg Gly Ala Leu Trp Arg Glu His Arg Ala
1               5                   10                  15

Val Glu Ala Ala Thr Ile Ala Ala Met Arg Ala Arg Gly Val Arg Asp
                20                  25                  30

Val Pro Trp Ser Ser Ala Lys Arg Met Leu Ala Val Leu Cys Val Ser
            35                  40                  45

Ala Ile Tyr Thr Ser Trp Ile Leu Ser Pro Val Ser Ala Val Ala
50                  55                  60

Val Ile Leu Ile Pro Ser Leu Arg Ala Tyr Val Gly Cys Tyr Leu Phe
65                  70                  75                  80

Ala Ser Tyr Ala Leu Gly Val Arg Val Pro Met Asn Gly Leu Tyr Lys
                85                  90                  95

Phe Phe Cys Gly Leu Glu Cys Gly Glu Asn Gly Trp Glu Leu Val
            100                 105                 110

Val Glu Asp Ala Thr Ala Gly Glu Lys Glu Ile Asp Cys Ser Lys Arg
        115                 120                 125

Ala Tyr Leu Phe Ala Ala His Pro His Gly Leu Phe Ala Ser Gly Cys
    130                 135                 140

Val Gly Asn Ile Val Leu Ser Asp Ala Ala Leu Arg Arg Phe Arg Ala
145                 150                 155                 160

Arg His Val Arg Phe Phe Ile Asn Asn Leu Leu Ile Ser Val Phe Pro
                165                 170                 175

Ile Ile Lys Asp Val Leu Ser Ser Leu Gly Phe Leu Pro Cys Thr Ala
            180                 185                 190

Lys Met Met Arg Arg Val Leu Gly Arg Gly Glu Thr Gly Met Ile Val
        195                 200                 205

Val Gly Gly Val Gln Glu Val Val Leu Thr Gly Asn Val Asp Val Glu
    210                 215                 220

Glu Leu Tyr Leu Lys Asn Cys Phe Gly Phe Val Lys Val Ala Ile Gln
225                 230                 235                 240

Val Gly Thr Pro Leu Val Pro Val Tyr Thr Phe Gly Glu Ser Leu Ala
                245                 250                 255

Thr Gly Pro Asp Trp Val Pro Phe Arg Glu Ile Arg Lys Arg Leu Ser
            260                 265                 270

Tyr Lys Phe Val Phe Pro Phe Arg Ser Leu Gly Ile Val His Arg Trp
        275                 280                 285

Gly Phe Cys Phe Pro Arg Gly Lys Leu Thr Thr Val Val Gly Pro Pro
    290                 295                 300

Ile Glu Val Lys Gln Asn Asp Arg Pro Ser Arg Glu Glu Val Ala Ala
305                 310                 315                 320

Val His Ala Gln Tyr Cys Lys Ser Leu Leu Ala Leu Ile Glu Arg Asn
                325                 330                 335

Lys Ala Ala Ala Gly Tyr Pro Thr Gln Val Thr Arg Leu Val
```

<210> SEQ ID NO 48
<211> LENGTH: 1053
<212> TYPE: DNA
<213> ORGANISM: Ostreococcus lucimarinus

<400> SEQUENCE: 48

```
atgggctcga acgcgcagcg cggtgcgctc tggcgcgaac accgcgccgt ggaggcggcg      60
acgatcgcgg cgatgcgcgc gcgcggcgtg cgcgacgtgc cgtggagctc cgcgaagcgc     120
atgctcgcgg tgctgtgcgt cagcgcgatt tacacgtcgt ggatcctgtc cccggtcgtg     180
tccgcggtgg cggtgatttt gataccgtcg ttgcgagcgt acgtcgggtg ttatctcttc     240
gcgtcgtacg cgctcggggt gcgtgtgccc atgaatgggc tttataaatt cttttgcggg     300
ctcgagtgcg gagaagaaaa tggatgggaa ctcgtcgtcg aggacgcgac ggcgggcgag     360
aaagagattg attgctctaa gcgcgcgtat ttgttcgccg cgcacccgca cgggttattc     420
gcgtctggtt gcgtggggaa tatcgtattg agcgacgcgg cgttgaggcg attccgagcg     480
cggcacgtta gattcttcat caacaacttg ctcataagcg tgtttccgat catcaaagat     540
gtgctgtcgt cgcttgggtt cttaccatgc acagcaaaaa tgatgcgacg ggttttaggg     600
cgtggggaga ctgggatgat tgttgttggc ggcgttcaag aggtggtgct gacgggcaac     660
gtcgacgtcg aagagctata cttgaagaat tgtttcggat tcgtcaaggt agccatccaa     720
gtcggaacgc ccttagtgcc agtatacacg tttggcgagt ctctggctac tggtccggat     780
tgggtgccgt ttcgtgagat acgaaaacgc ctgagctata aatttgtatt tccgttccgc     840
tcgctcggca tcgtccatcg ttggggattc tgctttccgc gaggcaagct cacgacagtg     900
gtgggaccac ctattgaagt taagcagaac gatagaccgt cgcgcgagga agtggctgcg     960
gtgcatgcgc agtattgtaa gtcgcttttg gcactcattg aacgaaacaa agccgccgcg    1020
ggatacccaa cccaggtgac aagattggta tag                                 1053
```

<210> SEQ ID NO 49
<211> LENGTH: 421
<212> TYPE: PRT
<213> ORGANISM: Ostreococcus tauri
<220> FEATURE:
<221> NAME/KEY: misc_feature
<222> LOCATION: (58)..(65)
<223> OTHER INFORMATION: Xaa can be any naturally occurring amino acid

<400> SEQUENCE: 49

```
Met Ala Ala Ala Ala Asp Ala Lys Ala Ile Val Leu Ala Ser Thr Cys
1               5                   10                  15

Val Leu Val Ala Thr Cys Ala Thr His Phe Gly Ala Gly Arg Ala Leu
            20                  25                  30

Trp Ser Asp Arg Gly Trp Arg Ala Trp Gln Pro Met Arg Gly Arg Arg
        35                  40                  45

Ala Phe Val Ala Leu Gln Pro Val Gly Xaa Xaa Xaa Xaa Xaa Xaa Xaa
    50                  55                  60

Xaa Gly Ala Gly Glu Pro Leu Val Gly Val Ser Leu Ala Phe Phe Asp
65                  70                  75                  80

Glu Thr Arg Ala Gly Gly Arg Thr Ser Glu Thr Met Asp Ala Arg Asn
                85                  90                  95

Val Ala Arg Val Val Gln Met Leu Thr Val Leu His Val His Ala
            100                 105                 110
```

```
Pro His Met Ala Val Phe Ala Val Leu Gly Thr Ala Tyr Ala Leu Gly
        115                 120                 125

Arg Trp Arg Thr Leu Ala Ala Val Val Ala Leu Tyr Ala Ser Thr Tyr
130                 135                 140

Val Thr Arg Gln Lys Ser Leu Glu Arg Gly Gln Arg Lys Trp Glu Gln
145                 150                 155                 160

Phe Gln Thr Trp Thr Leu Arg Thr Val Glu Gly Ala Ala Lys Ser Trp
                165                 170                 175

Tyr Gly Ser Val Arg Val Val His Asp Gly Lys Val Ser Glu Ala Ala
                180                 185                 190

His Ser Ser Pro His Val Phe Ala Tyr His Pro His Ser Met Val Pro
        195                 200                 205

Ala Gly Ala Val Trp Phe His Met Leu Pro Asp Phe Ser Ala Arg Phe
210                 215                 220

Arg Gly Ile Gln Pro Val Thr Leu Ala Ala Ser Val Leu Phe Lys Ala
225                 230                 235                 240

Pro Ile Val Arg Glu Leu Ala Ala Trp Leu Gly Val Arg Ala Val Ser
                245                 250                 255

Arg Glu Ile Phe Arg Ser Thr Leu Arg Glu Gln Gly Ala Val Val Val
                260                 265                 270

Cys Pro Gly Gly Gln His Glu Met Gln Glu His Gly Pro Met Glu
        275                 280                 285

Glu Thr Ile Val Leu Cys Thr Lys His Lys Gly Phe Ile Arg Ile Ala
        290                 295                 300

Ile Glu Glu Arg Ala Arg Val Val Pro Val Ile Cys Phe Gly Glu Ser
305                 310                 315                 320

Lys Ser Trp Thr Asn Ile Met Ala Lys Pro Gly Arg Tyr Leu Tyr Arg
                325                 330                 335

Arg Phe Arg Phe Gly Phe Thr Pro Leu Leu Ala Val Gly Tyr Leu Gly
                340                 345                 350

Ile Leu Pro Leu Pro Arg Arg Val Pro Ile Thr Phe Val Ile Gly Glu
            355                 360                 365

Pro Met Val Leu Pro Asp Pro Asp Ala Leu Thr Gly Leu Ala Lys Glu
370                 375                 380

Ser Asp Val Asp Ala Phe His Ala Ser Tyr Tyr Ser Gln Val Glu Arg
385                 390                 395                 400

Leu Phe Asp Glu His Lys Ser Lys Ala Gly Phe Pro Glu Leu Cys Leu
                405                 410                 415

Val Met Lys Asn Asp
            420

<210> SEQ ID NO 50
<211> LENGTH: 1266
<212> TYPE: DNA
<213> ORGANISM: Ostreococcus tauri
<220> FEATURE:
<221> NAME/KEY: misc_feature
<222> LOCATION: (174)..(193)
<223> OTHER INFORMATION: n is a, c, g, or t

<400> SEQUENCE: 50
atggcggcgg cggcggacgc gaaagccatc gtcttggcct cgacgtgcgt cctcgtcgcg    60
acgtgcgcga cgcacttcgg cgcgggccga gcgctgtgga gcgatcgagg atggcgggcg   120
tggcagccga tgcgcggacg gcgcgcgttc gtggcgctgc agccggtggg gtgnnnnnnn   180
nnnnnnnnnn nngggggtgc gggtgagccc ttggtggggg tgtcgctggc gttttttgat   240
```

```
gagacgcgcg cgggcgggcg gacgtcggag acgatggacg cgcgaaacgt cgcgcgcgtg    300
gtgcagatgt tgaccgtctt gcacgtcgtg cacgcgccgc acatggcggt gtttgcggtg    360
ttggggacgg cgtacgcgtt gggtcgatgg cgtacgctcg cggcggtggt cgcgttgtac    420
gcgtcgacgt acgtgacgag acagaagtcg ctcgagcggg gacagagaaa gtgggagcag    480
ttccagacgt ggacgcttcg gacggtggag ggggcggcga atcgtggta cgggagcgtg     540
cgcgtggtgc acgacgggaa ggtttcggaa gcggcgcatt cgtcgccgca cgtcttcgcg    600
taccacccgc actcgatggt tcccgcgggc gccgtgtggt ttcacatgct cccggatttt    660
agcgcccgtt ttcgcgggat tcaacccgtg acgctcgcag cctcggtttt gtttaaggca    720
ccgatcgtcc gggagcttgc ggcgtggctt ggcgttcgtg cggtgagcag agagatttc     780
cgttcgacgc tacagagaca aggcgcggtt gtcgtgtgcc cgggaggaca gcacgagatg    840
caagagcacg gaggtccgat ggaggagacg atcgttttat gcaccaaaca taaaggattc    900
attcgaatag cgatcgagga gcgcgcgcgc gtcgtccccg tgatttgttt cggcgagagc    960
aagagttgga ccaacatcat ggcaaagccg ggccgttatc tctacagacg ctttcgattc   1020
ggtttcaccc cgttactagc cgtgggctac ctcggaattc ttccgctccc gagacgcgta   1080
cccatcacgt tcgtcatcgg cgagccgatg gtacttcctg atccggatgc cttgacggga   1140
ctggcgaagg aatcggatgt cgacgcgttc cacgcgtcgt attacagtca agtggagaga   1200
ctgttcgacg agcacaaatc caaagccggg ttccctgagc tttgcctcgt gatgaaaaac   1260
gattag                                                              1266
```

<210> SEQ ID NO 51
<211> LENGTH: 325
<212> TYPE: PRT
<213> ORGANISM: Ostreococcus tauri

<400> SEQUENCE: 51

```
Met Ser Arg Ser Ile Val Asp His Gly Val Leu Leu Val Trp Leu Gly
1               5                   10                  15
Leu Phe His Ala Leu Val Val Val Val Val Ala Ile Val Ala Leu
            20                  25                  30
Glu Arg Arg Arg Ala Met Thr Val Leu Ala Ala Leu Met Ser Leu Ser
        35                  40                  45
Val Val Pro Arg Arg Ile Arg Pro Arg Trp Gly Val Thr Leu Ala Arg
    50                  55                  60
Ala Ile Thr Arg Thr Ala Lys Ser Tyr Phe Pro Cys Ala Leu Thr Phe
65                  70                  75                  80
Glu Asn Glu Glu Ala Tyr Leu Lys Gly Ala Arg Lys Gly Val Gly Arg
                85                  90                  95
Leu Val Gly Leu Glu Pro His Gly Ala Leu Pro Leu Ser Val Ile Ala
            100                 105                 110
Phe Ala Asp Tyr Phe Met Phe Asp Glu Asp Gly Ile Glu Ala Arg Gly
        115                 120                 125
Met Asn His Ala Ala Ser Met Asn Ser Arg Ala Leu Ala Ser Gly Ala
    130                 135                 140
Ile Phe His Val Pro Leu Val Arg His Leu Trp Thr Trp Leu Gly Leu
145                 150                 155                 160
Glu Pro Ile Ser Arg Arg Met Thr Ser Met Leu Ser Asp Gly Ser
                165                 170                 175
Thr Cys Val Ile Val Pro Gly Gly Val Ala Glu Cys Met Ala Met Glu
```

```
              180                 185                 190
Arg Gly Val Glu Thr Leu Tyr Leu Lys Arg Arg Tyr Gly Phe Val Lys
            195                 200                 205

Ile Ala Ile Gln Thr Gly Ala Ala Leu Val Pro Ala Tyr Thr Phe Gly
            210                 215                 220

Gln Thr Arg Ala Tyr Lys Tyr Trp Arg Leu Gly Pro Pro Leu Val Pro
225                 230                 235                 240

Thr Ser Val Ala Asn Trp Phe Ser Lys Thr Phe Ser Phe Ala Pro Met
                245                 250                 255

Val Phe Trp Gly Lys Trp Phe Thr Pro Ile Pro Tyr Ala Thr Pro Leu
                260                 265                 270

His Thr Val Val Gly Glu Leu Ile Glu Thr Thr Gln Asn Asp Asn Pro
            275                 280                 285

Ser Arg Glu Glu Val Gln Ala Lys Leu Asp Glu Phe Ile Val Ala Met
            290                 295                 300

Arg Ser Leu Tyr Asp Arg His Lys Ser Ala His Gly Tyr Ala Asp Val
305                 310                 315                 320

Asp Leu Val Val Cys
            325

<210> SEQ ID NO 52
<211> LENGTH: 978
<212> TYPE: DNA
<213> ORGANISM: Ostreococcus tauri

<400> SEQUENCE: 52
atgtcgcgct cgatcgtcga tcacggcgtg ctgctcgtgt ggttggggtt gttccacgcc      60
ctggtcgtcg tcgtcgtcgt cgcgatcgtc gcgctcgagc gacgacgcgc gatgacggtg     120
ctcgccgcgt tgatgtcttt gagcgtcgtc ccgcggcgca tccgaccgcg ctggggcgtg     180
acgctggcgc gcgcgatcac gcgcacggcg aagtcgtatt tcccgtgcgc gttgacgttt     240
gagaacgagg aggcgtacct gaagggtgct cggaagggtg tcgggcggtt ggtgggtttg     300
gagccgcacg gagcgctgcc gctctcggtg atcgcgttcg cggattactt catgttcgat     360
gaagatggga tcgaggcgag ggggatgaat acgctgcgt cgatgaattc gcgagcgttg      420
gcgtcggggg cgatatttca cgtcccgttg gtgcgacacc tgtggacgtg gttgggattg     480
gaaccgatat ctcgaaggcg gatgacgagt atgttaagcg acggttcgac gtgcgtgatc     540
gtgccgggtg ggtggcgga gtgcatggcg atggagagag gggttgagac gctgtatctc      600
aagcgaaggt acgggttcgt gaagattgcg atacagacgg cgcggcact cgtgccggcg      660 tacacgtttg gcagacgcg ggcgtacaag tactggcgac tcggtccgcc gttggtgccg      720
acgtccgttg caaattggtt ctcgaaaacg ttttctttcg cacccatggt tttttgggga     780
aagtggttca cgcccattcc gtacgctacc cctctgcaca cggtggttgg cgagctcatc     840
gagaccacgc aaaacgacaa tccgagtcgc gaggaggtgc aggcaaagct tgacgagttc     900
atcgtcgcta tgcgttcgct gtacgaccga cacaaatctg cacacgggta tgccgacgtc     960
gacctcgtcg tgtgctga                                                   978

<210> SEQ ID NO 53
<211> LENGTH: 314
<212> TYPE: PRT
<213> ORGANISM: Ostreococcus tauri

<400> SEQUENCE: 53
```

Met Arg Asn Ala Phe Leu Gly Tyr Ile Gly Trp Tyr Val Leu Leu Asp
1               5                   10                  15

Arg Arg Ser Asp Ser Ser Gly Thr Arg Phe Val Ala Trp Ser Arg Arg
            20                  25                  30

Leu Pro Phe Trp Arg Ile Leu Ala Asp Tyr Phe Pro Val Arg Leu Tyr
                35                  40                  45

Lys Ser Gly Glu Leu Asp Pro Lys Gly Asn Tyr Leu Phe Gly Tyr His
50                  55                  60

Pro His Gly Val Ile Gly Val Gly Ala Leu Met Thr Phe Ala Thr Glu
65                  70                  75                  80

Ala Thr Gly Phe Tyr Glu Ala Phe Pro Gly Leu Asp Leu Arg Leu Leu
                85                  90                  95

Thr Leu Ser Val Asn Phe Lys Phe Pro Phe Thr Arg Glu Val Leu Met
                100                 105                 110

Ala Leu Gly Ile Asn Ser Val Thr Lys Ala Ser Val Met Thr Asn Leu
                115                 120                 125

Thr Arg Ala Pro Gly Ala Ser Val Ala Ile Val Ile Gly Gly Ala Ala
            130                 135                 140

Glu Ala Leu Asp Ala Arg Pro Gly Ser Ala Thr Leu Thr Leu Ala Arg
145                 150                 155                 160

Arg Lys Gly Phe Val Lys Met Ala Leu Arg Thr Gly Ala Ser Leu Val
                165                 170                 175

Pro Val Phe Ala Phe Gly Glu Asn Asp Ile Phe Glu Gln Val Glu Asn
                180                 185                 190

Pro Asp Gly Gly Arg Leu Arg Lys Phe Gln Thr Tyr Ile Lys Gln Leu
            195                 200                 205

Ile Gly Ile Ser Pro Pro Ala Phe Tyr Gly Arg Ser Leu Ser Arg Gly
210                 215                 220

Val Trp Arg Arg Ile Phe Gly Arg Lys Gly Val Leu Pro Lys Arg Glu
225                 230                 235                 240

Pro Ile Glu Val Ile Ile Gly Asn Pro Ile His Val Pro Gln Val Asp
                245                 250                 255

Asp Pro Ser Pro Asp Val Ile Asp Lys Tyr His Gln Leu Tyr Thr Val
            260                 265                 270

Gly Leu Lys Glu Leu Tyr Glu Leu His Arg Arg Gln Phe His Gln Leu
275                 280                 285

Asn Arg Gly Gly Ser Ser Asp Asp Leu Leu Ser Asp Leu Ile Lys Arg
            290                 295                 300

Lys Asn Asn Leu Gln Ala Met Thr Phe Lys
305                 310

<210> SEQ ID NO 54
<211> LENGTH: 945
<212> TYPE: DNA
<213> ORGANISM: Ostreococcus tauri

<400> SEQUENCE: 54
atgcggaacg cgttcttggg atacattggt tggtacgtgc tgttggaccg gcgctcggat      60
agctcgggca ctagattcgt ggcgtggtcg agacgtctac cttttttggcg catcctggct    120 gattacttcc cagttcgatt atacaagagc ggcgagctcg atccaaaagg gaattacttg    180
ttcgggtatc atccgcacgg cgtcatcggc gtcgggcgt tgatgacgtt tgccaccgaa     240
gcgacgggat tttacgaagc atttccagga ttggatttac ggctcttgac gttatcggtg    300
aacttcaagt ttccatttac gcgagaggtg ttgatggcgc tcggattaa ctccgtcact     360

```
aaggcgagcg tcatgaccaa tcttacccgc gcaccaggcg cgagcgtcgc catcgtcatc    420
ggcggcgccg cagaggcgtt ggacgctcgt ccgggatcgg ccacgctcac gctggcgaga    480
cgtaaagggt tcgtgaaaat ggctctgcgc acgggtgcat cgctcgtgcc tgtttttgcc    540
ttcggggaga acgatatttt cgagcaagtc gagaatcccg acggcgggcg cctgcgcaag    600
tttcagacgt acatcaagca actcatcgga atctcaccgc cggcttttta cggccgctcg    660
ctcagtcggg gggtgtggcg tcgcattttt gggcgtaagg gagtgctgcc gaagcgtgaa    720
ccgatcgaag tgatcatcgg taatcccata cacgtccctc aggtggacga tccgtcgccc    780
gacgtcatcg acaagtatca tcaattgtac accgtgggac tcaaggaact ttacgagctg    840
catcgcagac aatttcacca gttgaatcgc ggaggttctt ccgacgatct gctaagcgat    900
ctgatcaagc gtaagaacaa cctccaagcc atgacattca aatag                    945
```

<210> SEQ ID NO 55
<211> LENGTH: 354
<212> TYPE: PRT
<213> ORGANISM: Ostreococcus tauri

<400> SEQUENCE: 55

```
Met Arg Thr Ser Ser Gly Ala Gly Gly Thr Arg Ala Arg Arg His Cys
1               5                   10                  15

Ala Thr Thr Asp Val Ala Arg Ser Phe Asp Ala Val Arg Arg Glu Met
            20                  25                  30

Arg Glu Ala Arg Gly Ile Ala Asp Val Pro Trp Ser Ser Leu Lys Arg
        35                  40                  45

Leu Leu Gly Val Ser Cys Val Ser Ala Ile Tyr Thr Ser Trp Ile Leu
    50                  55                  60

Ser Pro Val Met Ser Ala Leu Ala Val Trp Arg Tyr Glu Trp Leu Arg
65                  70                  75                  80

Ala Tyr Val Ala Cys Tyr Leu Phe Ala Ser Tyr Ala Leu Gly Val Ala
                85                  90                  95

Met Pro Met Asn Ala Leu His Arg Phe Phe Cys Trp Leu Glu Thr Gly
            100                 105                 110

Glu Glu Asn Gly Trp Gln Leu Val Glu Asp Asp Cys Asp Val Asp
        115                 120                 125

Cys Ser Lys Arg Ala Tyr Leu Phe Thr Ala His Pro His Gly Leu Phe
    130                 135                 140

Ala Ser Gly Cys Val Gly Asn Val Val Leu Ser Gly Arg Ala Leu Lys
145                 150                 155                 160

Arg Phe Arg Ala Arg Arg Ile Trp Phe Phe Ile Asn Glu Leu Leu Ile
                165                 170                 175

Arg Val Phe Pro Ile Ile Lys Asp Val Leu Ser Met Leu Gly Phe Val
            180                 185                 190

Pro Cys Thr Ala Lys Met Met Lys Lys Val Leu Gly Arg Gly Glu Thr
        195                 200                 205

Gly Leu Ile Val Val Gly Gly Val Gln Glu Val Leu Thr Gly Asn
    210                 215                 220

Val Asp Glu Glu Glu Leu Tyr Leu Lys Asn Cys Phe Gly Phe Val Lys
225                 230                 235                 240

Val Ala Met Gln Ala Gly Thr Pro Leu Val Pro Val Tyr Thr Phe Gly
                245                 250                 255

Glu Ser Leu Ala Thr Gly Pro Asp Trp Val Pro Phe Arg Glu Leu Arg
            260                 265                 270
```

```
Lys Arg Leu Ser Tyr Lys Phe Val Phe Pro Phe Arg Ser Leu Gly Ile
            275                 280                 285

Ile His Arg Trp Gly Leu Cys Phe Pro Lys Ala Lys Leu Thr Thr Val
        290                 295                 300

Val Gly Ala Pro Ile Glu Val Lys Gln Asn Pro Asn Pro Thr Arg Glu
305                 310                 315                 320

Glu Val Ala Ala Val His Gln Gln Tyr Cys Asp Ala Leu Leu Ala Met
                325                 330                 335

Ile Glu Arg Asn Lys Ala Arg Ala Gly Tyr Pro Thr Gln Arg Thr Lys
            340                 345                 350

Leu Val

<210> SEQ ID NO 56
<211> LENGTH: 1065
<212> TYPE: DNA
<213> ORGANISM: Ostreococcus tauri

<400> SEQUENCE: 56
atgcgaacct cctcgggcgc gggaggaacg cgcgcgcgtc gtcactgtgc gacgacggac      60
gtcgcgcgat cgttcgacgc cgttcgcagg gagatgcgag aggcgcgagg gatcgcggac     120
gtccccctgga gctcgctcaa gcgcttgctc ggtgtctcgt gcgtgagcgc gatttacacg     180
tcgtggatcc tctccccggt gatgagcgcg ctcgcggtgt ggcggtacga gtggttgaga     240
gcgtacgtcg cgtgctatct cttcgcgtcc tacgcgctcg cgtggcgat gccgatgaac      300
gcgctgcatc ggttcttctg ttggctcgag acgggagagg aaaacgggtg gcagctcgtc     360
gtcgaggacg actgcgatgt ggactgctcg aagagggcgt acttgttcac ggcgcatccg     420
cacgggttgt tcgcgtcggg atgcgtcggg aacgtcgttt tgagcggacg cgcgctcaag     480
aggttccggg cgagacggat ttggttcttc atcaacgagc tgttaatccg agtgtttccg     540
atcatcaagg acgtgttgtc gatgctggga ttcgtgccgt gcacggcgaa aatgatgaag     600
aaggtgttgg aagggcga gaccggattg atcgtcgtcg gtggggttca ggaggttgtg     660
ttgactggta acgtcgacga agaggaactt tatctaaaaa attgtttcgg ctttgtcaaa     720
gtggccatgc aggccgggac gccgctcgtg cccgtataca cattcggcga atcgctagcc     780
accggcccgg actgggtacc gttcagagag ctgcgtaaac ggctgagcta caagtttgtg     840
ttcccgtttc gctcgcttgg cataatccat cgctggggc tctgctttcc caaggcaaag     900
ctcacgaccg tggtaggcgc gccgattgag gtgaaacaaa acccaaatcc cacgcgcgag     960
gaagttgcgg cggtgcatca gcagtattgc gacgcactgc tggcgatgat tgagcgaaac    1020
aaggcccgcg cggggtatcc gacgcaacgc acaaagttgg tgtaa                  1065

<210> SEQ ID NO 57
<211> LENGTH: 359
<212> TYPE: PRT
<213> ORGANISM: Phaeodactylum tricornutum

<400> SEQUENCE: 57

Met Lys Glu Arg Arg Ser Gly Leu Asn Pro Ser Gly Ser Ser Val Tyr
1               5                   10                  15

Pro Leu His Pro Pro Asp Ser Arg Val Leu Val Arg Val Pro Ser Asp
                20                  25                  30

Ile Ser Phe Leu Asp Arg Leu Ile Val Ala Gly Ser Ser Ile Phe Ile
            35                  40                  45
```

```
Val Gly Ser Leu Val Trp Val Pro Leu Thr Ala Arg Trp Val Tyr Arg
 50                  55                  60

Arg Trp Lys Gln Ala Lys Asp Lys Arg Lys Ala Leu Tyr Ala Ser
 65                  70                  75                  80

Leu Leu Val Ile Leu Ala Val Leu Val Ile Gly Gly Pro His Arg Ser
                 85                  90                  95

Pro Arg Val Gly Lys Trp Leu Gln Val Arg Lys Trp Ser Leu Phe Gln
                100                 105                 110

Ala Trp Val Lys Phe Ile Ala Met Glu Val Ile Leu Asp Gln Pro Lys
                115                 120                 125

Gly Ile Thr Met Asp Val Gln Gln Asp Lys Ala Ile Phe Ala Phe Ala
130                 135                 140

Pro His Gly Ile Phe Pro Phe Ala Phe Ala Phe Gly Val Leu Pro Asp
145                 150                 155                 160

Ile Ala Thr Gln Ser Phe Gly Tyr Val Arg Pro Val Val Ala Thr Ala
                165                 170                 175

Thr Arg Leu Phe Pro Val Val Arg Asp Phe Ile Ser Trp Ala Asn Pro
                180                 185                 190

Val Asp Ala Ser Lys Asp Ser Val Glu Arg Ala Leu Ala Leu Gly Asp
                195                 200                 205

Arg Ile Ala Val Ile Pro Gly Gly Ile Ala Glu Ile Phe Glu Gly Tyr
210                 215                 220

Pro Lys Pro Asn Thr His Pro Asp Glu Glu Tyr Ala Ile Val Arg Ser
225                 230                 235                 240

Gly Phe Leu Arg Leu Ala Ile Lys His Gly Ile Pro Val Ile Pro Val
                245                 250                 255

Tyr Cys Phe Gly Ala Thr Lys Met Leu Lys Arg Leu Glu Leu Pro Gly
                260                 265                 270

Leu Glu Gln Leu Ser Leu Phe Leu Arg Val Ser Ile Cys Leu Phe Phe
                275                 280                 285

Gly Val Gly Gly Leu Pro Ile Pro Phe Arg Gln Arg Leu Ser Tyr Val
                290                 295                 300

Met Gly Gln Pro Ile Leu Pro Pro Val Arg Thr Thr Gly Ser Asp Ile
305                 310                 315                 320

Ser Asp Ala His Val Lys Glu Met Gln Asp Arg Phe Cys Ala Glu Val
                325                 330                 335

Gln Arg Leu Phe Asp Arg His Lys Glu Ala Tyr Gly Trp Ser His Lys
                340                 345                 350

Thr Leu Lys Leu Leu Glu Gln
                355

<210> SEQ ID NO 58
<211> LENGTH: 1080
<212> TYPE: DNA
<213> ORGANISM: Phaeodactylum tricornutum

<400> SEQUENCE: 58
atgaaagaaa gaagatctgg cctaaatccg tcaggatcct ccgtgtatcc attgcaccct      60
cctgacagtc gcgttctcgt tcgagtcccc tccgatattt cctttcttga tcgtctcatc     120
gtcgctggca gcagtatctt tattgtcggt tcgctagtat gggttccatt gaccgcaaga     180
tgggtctaca gcggtggaa gcaagctaaa gataaacgaa agcgggcttt gtatgcctct     240
ctactcgtga ttctggcagt tctcgttatt ggcggacccc accgatctcc tcgtgtcggc     300
aaatggctcc aagtacgaaa gtggtccctc ttccaagcgt gggtaaagtt tattgctatg     360
```

```
gaagtgattt tggatcaacc gaaaggcatt actatggacg tccaacaaga caaggcgatt    420
tttgcattcg cgccacatgg aatctttccg tttgcgttcg cctttggagt gcttcccgat    480
attgccacac aatcgtttgg ctacgttcgt ccggtcgtgg caaccgccac aaggttgttt    540
cctgtagtcc gggatttcat ctcttgggcg aatccggtag acgcttccaa agattccgtt    600
gaacgtgctt tagcatttgg cgatcgcatt gctgtaatac ctggaggaat tgcagaaatt    660
ttcgaaggat atccgaaacc gaacacgcat ccggatgaag agtacgctat cgtacggagt    720 ggattttttgc gtttggcaat aaaacacggt atcccagtga ttcccgtata ctgtttcggc    780
gctaccaaaa tgttgaagcg tctggagctt cctggcctgg agcaactgtc cctgtttcta    840
cgcgtgagca tttgcctctt ttttggagtc ggcgggttgc ccatcccttt ccgacaacga    900
ttgtcgtacg taatgggaca accaattttg ccacccgtaa ggacaacggg cagcgatatt    960
tcggacgcac acgtcaaaga aatgcaagat cgcttttgtg ctgaggtcca gcggctcttt   1020
gatcgacata aggaagctta tggttggtcc cacaaaacgc tgaaactatt ggaacagtga   1080
```

<210> SEQ ID NO 59
<211> LENGTH: 392
<212> TYPE: PRT
<213> ORGANISM: Phaeodactylum tricornutum

<400> SEQUENCE: 59

```
Met Arg Glu Arg Ser Cys Ala Asn Ala Ser Asp Asp Ser Ile His
1               5                   10                  15

Lys Gln Ser Pro Glu Leu Glu Ala Glu Phe Leu His Thr Ser Lys Leu
            20                  25                  30

Thr Leu Ala Asp Met Arg Arg Leu Ala His Asp Pro Lys Asp Arg Arg
        35                  40                  45

Leu Ala Thr Lys Pro Ala Ala Gln Ala Thr Lys Glu Asp Val Leu Thr
    50                  55                  60

Val Gln Pro Met Ser Phe Val Glu His Thr Ala Cys Cys Leu Phe Leu
65                  70                  75                  80

Ala Phe Gly Val Pro Asn Gly Ala Leu Thr Ile Pro Ile Ala Thr Trp
                85                  90                  95

Leu Ile Gly Lys Phe Val Val Arg Asn Val Phe Leu Ala Phe Leu Leu
            100                 105                 110

Ala Gly Cys Ile Leu Leu Pro Leu Ala Ile Leu Pro Gln Glu Tyr Val
        115                 120                 125

Pro Ala Arg Leu Gln Ser Trp Leu Ala Leu Gln Ile Leu Lys Tyr Phe
    130                 135                 140

Ser Phe Ser Leu Val Met Glu Glu Arg Pro Pro Thr Met Cys Thr Gly
145                 150                 155                 160

Lys Gln Leu Ile Glu Gln Pro Ala Arg Pro Arg Ile Val Thr Ala Tyr
                165                 170                 175

Pro His Gly Val Phe Pro Tyr Gly Asn Ala Leu Thr Val Thr Trp
            180                 185                 190

Pro Leu Leu Thr Gly His His Ile Val Gly Leu Ala Ala Asn Ala Ala
        195                 200                 205

Leu Arg Thr Pro Ile Phe Lys Gln Ile Leu Arg Ser Ile Gly Val Lys
    210                 215                 220

Asp Ala Ser Arg Ala Ser Val Arg Asn Ala Leu Glu Thr Trp Pro Phe
225                 230                 235                 240

Thr Val Gly Ile Ser Pro Gly Gly Val Ala Glu Val Phe Glu Thr Asn
```

```
                245                 250                 255
His Phe Asn Glu His Ile Leu Leu Lys Glu Arg Ile Gly Val Ile Lys
            260                 265                 270

Met Ala Ile Arg Thr Gly Ala Asp Leu Val Pro Gly Tyr Met Tyr Gly
            275                 280                 285

Asn Thr Asn Leu Tyr Trp Cys Trp Thr Gly Glu Gly Ile Pro Gly Ala
            290                 295                 300

Arg Trp Leu Leu Glu Tyr Val Ser Arg Lys Ile Leu Gly Phe Ala Leu
305                 310                 315                 320

Val Pro Ile Ala Gly Arg Trp Gly Leu Pro Ile Pro Tyr Arg Thr Pro
                325                 330                 335

Ile Leu Cys Val Val Gly Lys Pro Ile Pro Thr Ile His Leu Gln Thr
            340                 345                 350

Glu Glu Pro Ser Met Glu Gln Ile Val Asp Ile Gln Glu Gln Leu Ser
            355                 360                 365

Thr Glu Leu Lys Ser Met Phe Asp Arg Tyr Lys His Leu Tyr Gly Trp
            370                 375                 380

Glu Asp Arg Met Leu Val Ile Thr
385                 390

<210> SEQ ID NO 60
<211> LENGTH: 1179
<212> TYPE: DNA
<213> ORGANISM: Phaeodactylum tricornutum

<400> SEQUENCE: 60
atgcgtgagc gaagctgcgc caacgcttct gacgatgaca gcattcacaa gcagtcgcca      60
gaattggagg ctgagtttct tcataccagc aagttgacct tagccgacat gcgacgattg     120
gcgcacgatc cgaaggatcg gaggttggca acaaaacctg cggcgcaagc tacgaaagaa     180
gacgtcttga cggtacaacc catgagtttc gtagaacaca ctgcttgctg tctgtttctc     240
gcgtttggag tgcccaatgg cgctctgacg attcccatag caacgtggct gatcggaaaa     300
ttcgtggtac gcaacgtttt cttggcgttt ctgttagcag gctgtatact tctaccgctt     360
gcgatactgc cgcaagaata tgtgcccgcc cgattgcaat cgtggcttgc tttgcagata     420
ctgaaatatt tttctttctc tttggtcatg gaggaacgcc ctccgacaat gtgtactggc     480
aagcagctga tcgagcagcc cgctcggcca cgaatcgtca cagcctatcc gcacggagtt     540
ttcccatacg gaaacgcgtt gactgtagtc acatggccgt tgttgacggg acaccatatt     600
gtgggtttgg cagcaaatgc cgctttgcgg acaccgatct ttaaacaaat cttgcggagc     660
attggcgtca aggacgcctc tcgagcgtcg gtacggaatg cgctggaaac atggcctttc     720
accgtcggga tttcgccagg tggcgtggcg gaagttttg aaacaaacca cttcaatgag     780
cacattctgt tgaaagaacg tattggtgtc atcaagatgg ccattcgcac cggtgcggat     840
cttgtaccag gctatatgta tggtaatact aatctgtact ggtgctggac aggggaaggt     900
attcctggag ctcggtggct attggagtat gtttcgcgta aaatcctagg ttttgccctc     960
gtgcctatag cgggtagatg gggactacca ataccgtaca ggactccgat attgtgtgtc    1020
gtgggcaagc caataccaac cattcatttg caaaccgaag aaccatcaat ggagcaaatc    1080
gtggacattc aggaacaatt gtcaacagaa ttgaaatcaa tgttcgaccg ctataagcac    1140
ctgtacggat gggaagatcg aatgctagtg atcacataa                           1179

<210> SEQ ID NO 61
```

<211> LENGTH: 329
<212> TYPE: PRT
<213> ORGANISM: Phaeodactylum tricornutum

<400> SEQUENCE: 61

```
Met Glu Arg Thr Lys Ile Gln Asp Glu His Lys Ser Pro Pro Asn Pro
1               5                   10                  15

Ser Thr Phe Arg Trp Phe Leu Gly Leu Leu Val Ala Ser Thr Phe Ser
            20                  25                  30

Met Val Tyr Phe Val Ala Pro Phe Tyr Met Leu Thr Val Phe Ala
        35                  40                  45

Leu Val Phe Lys Tyr Pro Ser Val Glu Ile Ala Trp Met Tyr Ala Ile
    50                  55                  60

Pro Met Ile Val Ser Ala Ile Leu Pro Pro Met Ala Ser Pro Leu Ala
65                  70                  75                  80

Leu Arg Leu Ile Ser Pro Leu Ile Asp Tyr Phe Asp Tyr Glu Glu Ile
                85                  90                  95

His Glu Thr Ser Pro Val Asp Val Gln Lys Glu Ile Leu Ser Asn Asn
            100                 105                 110

Lys Asn Tyr Leu Leu Val Phe Gln Pro His Gly Ala Leu Ser Phe Thr
        115                 120                 125

Gly Ile Thr Ser Met Val Thr Ala Pro Gln Ala Met Lys Gly Lys Leu
    130                 135                 140

Pro Thr Ala Val Ala Asp Ala Leu Leu Tyr Thr Pro Ile Leu Lys His
145                 150                 155                 160

Val Leu Gly Ile Phe Gly Leu Ile Ser Ala Ser Lys Ser Ser Met Ile
                165                 170                 175

Arg Thr Leu Lys Lys Lys Gly Val Glu Gly Thr Ile Val Leu Tyr Val
            180                 185                 190

Gly Gly Ile Ala Glu Leu Phe Leu Thr Asp Glu Thr Asp Glu Arg Leu
        195                 200                 205

Tyr Leu Arg Lys Arg Lys Gly Phe Ile Lys Leu Ala Leu Gln Gln Gly
    210                 215                 220

Val Asp Val Val Pro Val Tyr Leu Phe Gly Asn Thr Asn Ala Leu Ser
225                 230                 235                 240

Val Leu Lys Thr Gly Phe Leu Ala Ala Ile Ser Arg Lys Leu Gln Ile
                245                 250                 255

Ser Leu Thr Tyr Ile Trp Gly Lys Trp Tyr Leu Pro Ile Pro Arg Asp
            260                 265                 270

Cys Lys Leu Leu Tyr Ala Ser Gly Gln Pro Leu Gly Met Pro His Ile
        275                 280                 285

Leu Asp Pro Ser Gln Ala Asp Ile Asp Lys Trp His Glu Lys Tyr Cys
    290                 295                 300

Ser Glu Val Met Arg Ile Phe Glu Lys Tyr Lys Glu Lys Val Pro Glu
305                 310                 315                 320

Tyr Lys His Lys Lys Leu Glu Ile Ile
                325
```

<210> SEQ ID NO 62
<211> LENGTH: 990
<212> TYPE: DNA
<213> ORGANISM: Phaeodactylum tricornutum

<400> SEQUENCE: 62
atggagagaa caaagataca agacgagcac aaaagtcccc ctaatccgtc gacatttcga    60

```
tggttcctcg gccttctagt ggcgtcgacg ttttccatgg tctattttgt ggctcccttt    120
tacatgctta cagtcgtgtt tgcactagtt ttcaaatatc cttcggtaga aattgcatgg    180
atgtacgcta ttccgatgat tgtctcggcc attttgccac caatggcttc tccacttgcc    240
ttgcgactca tctccccgct cattgactac ttcgattacg aagagatcca cgaaacctca    300
ccggtggacg tccagaagga aatactaagc aacaacaaaa actatttgct agtctttcaa    360
ccgcatggag cactgtcgtt tacaggaatc acttcaatgg tgacagctcc acaagcaatg    420
aaaggcaaat tgccaacagc tgtggctgac gcactcttgt acacacctat actgaaacat    480
gtcttaggaa ttttcgggct gattagtgcc tccaaaagca gcatgatccg aactttaaaa    540
aagaagggtg tggaaggaac cattgttttg tacgttggtg ggattgccga gctcttttg    600 accgacgaga cggacgagcg cctctatctg cgaaagcgaa aagggtttat caaattagct    660
ctacaacagg gtgtcgatgt tgtacctgtg tatctatttg ggaacacaaa cgcgctgtcg    720
gtactaaaga cgggatttct cgcggcaatt tcgcgaaaat tacagatatc tctgacgtac    780
atttggggaa agtggtatct tccgattccc cgtgattgca aattgctgta tgcttccggt    840
cagccattag gaatgcctca tattttagac ccaagccaag ccgacattga taaatggcac    900
gaaaagtact gctccgaggt catgcggatc ttcgaaaaat acaaggaaaa ggttccggaa    960
tacaagcaca gaaaattaga aattatttga                                     990
```

```
<210> SEQ ID NO 63
<211> LENGTH: 320
<212> TYPE: PRT
<213> ORGANISM: Phaeodactylum tricornutum

<400> SEQUENCE: 63
```

Met Thr Arg Ser Lys Phe Ile Gly Ser Ala Gly Ala Ile Gly Leu Phe
1               5                   10                  15

Cys Leu Met Ile Ile Pro Asn Val Gly Ile Leu Ile Ala Thr Phe Leu
            20                  25                  30

Tyr Pro Lys Val Leu Gly Phe Tyr Phe Leu Ile Pro Tyr Tyr Ala Tyr
        35                  40                  45

Asn Leu Ser Ile Gly Lys His Glu Ala Arg Asp Gly Asn Gly Trp Asn
    50                  55                  60

Trp Phe Ser Glu Asn Phe Phe Val Phe Asn Ile Val Arg Gly Tyr Leu
65                  70                  75                  80

Asn Leu Lys Ile Glu Ala Asp Ser Glu Leu Lys Glu Ala Glu Ala Lys
                85                  90                  95

Glu Gly Ala Gln Phe Val Phe Ala Val Ser Pro His Gly Thr Asn Ala
            100                 105                 110

Asp Tyr Arg Val Phe Ile Asp Gly Met Leu His Glu Ala Leu Pro Gln
        115                 120                 125

Thr Ala Ser Lys Ile Arg Thr Leu Ala Ala Thr Val Leu Phe His Ile
    130                 135                 140

Pro Leu Val Arg Glu Ile Ala Leu Trp Thr Gly Cys Val Asp Ala Ser
145                 150                 155                 160

Arg Ala Val Ala Val Glu Arg Leu Lys Glu Glu Gly Gly Ser Leu Leu
                165                 170                 175

Val Ile Pro Gly Gly Gln Ala Glu Gln Met Tyr Thr Gln Tyr Gly Arg
            180                 185                 190

Glu Arg Val Tyr Leu Lys Arg Arg Lys Gly Phe Leu Lys Leu Cys Leu
        195                 200                 205

```
Lys Tyr Glu Ile Pro Val Val Pro Ala Tyr Val Phe Gly Val Ser Asp
    210                 215                 220
Tyr Tyr Phe Thr Ser Ala Lys Leu Phe Gly Leu Arg Met Trp Leu Val
225                 230                 235                 240
Gln Asn Leu Gly Ile Ala Leu Pro Leu Cys Trp Gly Arg Tyr Gly Leu
            245                 250                 255
Pro Ile Cys Pro Arg Pro Val Asp Thr Thr Leu Val Phe Asp Lys Pro
            260                 265                 270
Leu Tyr Leu Ser Cys Gln Asn Pro Ser Asn Pro Ser Glu Asp Glu Val
        275                 280                 285
Asp Lys Ala His Leu Gln Phe Cys Gln Ala Leu Glu Lys Leu Phe Asp
    290                 295                 300
Thr His Lys Glu Arg Leu Gly Tyr Gly Asp Arg Lys Leu Glu Ile Ile
305                 310                 315                 320

<210> SEQ ID NO 64
<211> LENGTH: 963
<212> TYPE: DNA
<213> ORGANISM: Phaeodactylum tricornutum

<400> SEQUENCE: 64
atgaccagat cgaagtttat aggaagtgct ggagctattg gcttattttg tttgatgatc      60
ataccgaatg tgggaattct gatcgcaaca tttctttatc ccaaagtact tgggttctac     120
tttctgattc cgtactacgc atacaacttg tccattggca aacacgaagc tcgagacggc     180
aacggctgga attggttcag cgagaatttc tttgtcttta acattgtgag gggatatcta     240
aatcttaaga ttgaagctga ctccgagctc aaggaagccg aagcgaaaga aggcgcccaa     300
tttgtgttcg ccgttagccc tcacggaacg aacgcagact atcgagtttt tattgacggt     360
atgctacatg aggcactccc acagactgca agcaagatca gaacactagc ggcgacagta     420
ctgttccaca ttcccttggt tcgtgaaatc gcactttgga caggatgtgt cgatgccagc     480
cgcgcagttg ctgtcgagag attaaaagaa gaaggtggtt cactgcttgt gattcccggt     540
ggccaagcag aacaaatgta cacccaatat ggacgtgaaa gagtatatct gaaacggcgc     600
aaaggatttt tgaagctttg cttgaagtac gagattccgg tcgtcccagc ttatgttttt     660
ggcgtatctg actattactt cacgtccgca aagctctttg gtctgcgaat gtggctcgtt     720
cagaatcttg gcattgctct tccactgtgc tggggaagat atggtctacc aatctgtcct     780
agaccagtcg ataccaccct tgtctttgac aaacctttat acctatcctg ccagaatccg     840
tcgaatccct cggaagacga ggttgacaag gctcatctgc aattttgcca agccctcgag     900
aagctgtttg atacacacaa agagaggctt gggtacggcg atcgaaagct ggaaataatt     960
tag                                                                    963
```